United States Patent
Bekalu et al.

(10) Patent No.: US 11,549,124 B2
(45) Date of Patent: Jan. 10, 2023

(54) NEPENTHESIN-1 DERIVED RESISTANCE TO FUNGAL PATHOGENS IN MAJOR CROP PLANTS

(71) Applicant: AARHUS UNIVERSITET, Aarhus C (DK)

(72) Inventors: Zelalem Eshetu Bekalu, Aarhus V (DK); Giuseppe Dionisio, Slagelse (DK); Claus Krogh Madsen, Ringsted (DK); Inger Bæksted Holme, København V (DK); Thomas Povl Etzerodt, Hvidovre (DK); Inge Fomsgaard, København V (DK); Lise Nistrup Jørgensen, Slagelse (DK); Henrik Brinch-Pedersen, Skælskør (DK)

(73) Assignee: AARHUS UNIVERSITET, Aarhus C (DK)

( * ) Notice: Subject to any disclaimer, the term of this patent is extended or adjusted under 35 U.S.C. 154(b) by 81 days.

(21) Appl. No.: 16/648,122

(22) PCT Filed: Sep. 20, 2018

(86) PCT No.: PCT/EP2018/075527
§ 371 (c)(1),
(2) Date: Mar. 17, 2020

(87) PCT Pub. No.: WO2019/057845
PCT Pub. Date: Mar. 28, 2019

(65) Prior Publication Data
US 2020/0325490 A1   Oct. 15, 2020

(30) Foreign Application Priority Data
Sep. 20, 2017   (EP) .................................. 17192155

(51) Int. Cl.
| C12N 15/82 | (2006.01) |
| A23K 10/30 | (2016.01) |
| C12Q 1/68 | (2018.01) |
| C12N 9/50 | (2006.01) |
| C12Q 1/6895 | (2018.01) |

(52) U.S. Cl.
CPC .......... *C12N 15/8282* (2013.01); *A23K 10/30* (2016.05); *C12N 9/63* (2013.01); *C12N 15/8234* (2013.01); *C12Q 1/6895* (2013.01); *C12Y 304/23* (2013.01); *C12Y 304/23012* (2013.01)

(58) Field of Classification Search
None
See application file for complete search history.

(56) References Cited

U.S. PATENT DOCUMENTS

| 6,642,437 B1 * | 11/2003 | Lemaux ............. C12N 15/8201 435/420 |
| 9,005,610 B2 | 4/2015 | Schreiner et al. |
| 2012/0005773 A1 | 1/2012 | Aasen et al. |
| 2017/0067040 A1 * | 3/2017 | Schriemer ............. A23L 33/105 |

FOREIGN PATENT DOCUMENTS

WO   WO 2000/004040   1/2020

OTHER PUBLICATIONS

Timotijevic et al . Ubiquitous aspartic proteinase as an actor in the stress response in buckwheat. (2010) Journal of Plant Physiology; vol. 167; pp. 61-68 (Year: 2010).*
Xia et al. An extracellular aspartic protease functions in *Arabidopsis* disease resistance signaling. (2004) The EMBO Journal; vol. 23; pp. 980-988 (Year: 2004).*
Mendieta et al. Antimicrobial activity of potato aspartic proteases (StAPs) involves membrane permeabilization. (2006) Microbiology; vol. 152; pp. 2039-2047. (Year: 2006).*
Fang et al. Isolation and characterization of a novel seed-specific promoter from Malaytea Scurfpea. (2015) Plant Mol. Biol. Rep.; vol. 33; pp. 1171-1179 (Year: 2015).*
NCBI Aspartic proteinase nepenthesin-1-like [*Aegilops tauschii* subsp. *tauschii*] (2017) GenPept. Accession No. XP_020183092; pp. 1-2 (Year: 2017).*
Wang et al. Protein secretion in plants: conventional and unconventional pathways and new techniques. (2018) J. or Experimental Botany; vol. 69; pp. 21-37 (published in advance on Aug. 3, 2017) (Year: 2018).*
Andersen, "Healthycrop.world—Fusarium resistant GM Soybean, Maize, Rapeseed and Cotton", Mar. 19, 2018, retrieved from internet, HTTP://dipfair.sdu.dk/Dipfair2018/EE02.pdf [retrieved on Oct. 26, 2018].

(Continued)

*Primary Examiner* — Cathy Kingdom Worley
(74) *Attorney, Agent, or Firm* — Casimir Jones SC; Lisa Mueller

(57) ABSTRACT

The invention relates to a genetically modified cereal plant having a recombinant DNA construct comprising a gene encoding a polypeptide having aspartyl protease activity (EC 3.4.23.12) whose expression, particularly in grain, confers enhanced fungal disease resistance as compared to a parent cereal plant from which said genetically modified cereal plant was derived. The invention further relates to a method for producing a genetically modified cereal plant of the invention comprising transforming one or more cells of a parent cereal plant with the recombinant DNA construct; as well as a method for manufacturing the genetically modified grain for production of a crop of genetically modified cereal plants which exhibit increased resistance to a fungal disease due to expression of the recombinant DNA construct. Furthermore, use of grain produced by a genetically modified cereal plant of the invention includes the manufacture of a composition, comprising a milled grain composition, an animal fodder, or steam-pelleted animal fodder.

15 Claims, 11 Drawing Sheets

Figure 1:
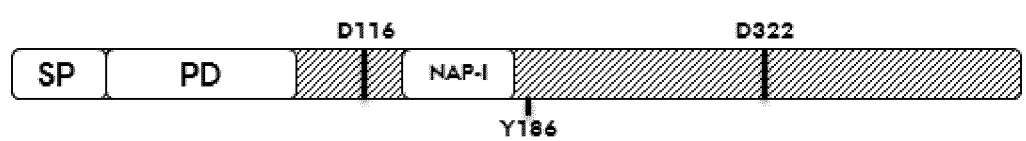
Figure 1:

Specification includes a Sequence Listing.

(56) References Cited

OTHER PUBLICATIONS

Athauda, et al. "Enzymic and structural characterization of nepenthesin, a unique member of a novel subfamily of aspartic proteinases" Biochemical Journal 2004, 381:295-306.
Bartlett, et al. 2008 "High-throughput Agrobacterium-mediated barley transformation" Plant Methods 2008, 4:22, 12 pages.
Bekalu, et al. "Aspergillus ficuum phytase activity is inhibited by cereal grain components" PLOS ONE, May 4, 2017, 13 pages.
Boue, et al. "Effect of soybean lipoxygenase on volatile generation and inhibition of aspergillus flavus mycellial growth" Journal of Agricultural and Food Chemistry 2005, 53(12): 4778-4783.
Chomczynski et al. "The single-step method of RNA isolation by acid guanidinium thiocyanate-phenol-chloroform extraction: twenty-something years ago" Nature Protocols 2006, 1(2): 581-585.
Dionosio, et al. "Cloning and Characterization of Purple Acid Phosphatase Phytases from Wheat, Barley, Maize, and Rice" Plant Physiology 2011, 156: 1087-1100.
Doan & Davis, "Efficacy of seed treatments on viability of *Fusarium oxysporum* f.sp *vasinfectum* race 4 in infected cotton seed" Crop Protection 2015, 78: 178-184.
Doyle et al. "DNA protocols for plants" in Molecular Techniques in Ta

| Samples used for analysis | | NEP02-01 | NEP02-02 | NEP04 | NEP05 | NEP06 | NEP16 | NEP18 | NEP19 | NEP20 | NEP20-02 | GP-1 | GP-2 | Mycotoxins (μg/kg DW) |
|---|---|---|---|---|---|---|---|---|---|---|---|---|---|---|
| FC+ | | 15938 | 794 | 1627 | 1231 | 9198 | 925 | 1257 | <50 | 25043 | 462 | 7264 | 77 | NIV |
|  | | <50 | <50 | <50 | <50 | 52 | <50 | <50 | <50 | 152 | <50 | 37091 | 2324 | DON |
|  | | <5 | <5 | <5 | 55 | <5 | <5 | <5 | <5 | <5 | <5 | 186 | 55 | ZEA |
| FC- | | 77 | <50 | <50 | <50 | <50 | <50 | <50 | <50 | <50 | <50 | <50 | <50 | NIV |
|  | | <50 | <50 | <50 | <50 | <50 | <50 | <50 | <50 | <50 | <50 | 142 | 855 | DON |
|  | | <5 | <5 | <5 | <5 | <5 | <5 | <5 | <5 | <5 | <5 | <5 | 15 | ZEA |
| FG+ | | 35510 | 6243 | 1543 | 16377 | 29727 | 597 | 97 | <50 | 53 | 2399 | 13050 | <50 | NIV |
|  | | 5295 | <50 | 56 | <50 | <50 | <50 | <50 | 8170 | 40073 | <50 | 6022 | 1664 | DON |
|  | | <5 | <5 | <5 | <5 | <5 | <5 | <5 | <5 | 256 | <5 | <5 | 38 | ZEA |
| FG- | | 124 | <50 | <50 | <50 | 171 | 163 | <50 | <50 | <50 | <50 | <50 | <50 | NIV |
|  | | <50 | <50 | <50 | <50 | <50 | <50 | <50 | <50 | <50 | <50 | 569 | 240 | DON |
|  | | <5 | <5 | <5 | <5 | <5 | <5 | <5 | <5 | <5 | <5 | <5 | <5 | ZEA |
| MQ | | <50 | <50 | <50 | <50 | <50 | <50 | <50 | <50 | <50 | <50 | <50 | <50 | NIV |
|  | | <50 | 52 | <50 | <50 | <50 | <50 | <50 | <50 | <50 | <50 | <50 | <50 | DON |
|  | | <5 | <5 | <5 | <5 | <5 | <5 | <5 | <5 | <5 | <5 | <5 | <5 | ZEA |

HvNEP-1 transgenic lines and GP controls

Figure 14

NEPENTHESIN-1 DERIVED RESISTANCE TO FUNGAL PATHOGENS IN MAJOR CROP PLANTS

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 144,452 Byte ASCII (Text) file named "2020-06-11_38324-251_SQL_ST25.txt," created on Jun. 11, 2020.

FIELD OF THE INVENTION

The invention provides a genetically modified crop plant having a recombinant DNA construct comprising a gene encoding a polypeptide having aspartyl protease activity (EC 3.4.23.12) whose enhanced expression, particularly in grain or seed, confers enhanced fungal disease resistance as compared to a parent crop plant from which said genetically modified crop plant was derived. The invention further provides a method for producing a genetically modified crop plant of the invention comprising transforming one or more cells of a parent plant with a recombinant DNA construct. Further provided is a method for manufacturing the genetically modified grain or seed for production of a crop of genetically modified plants which exhibit increased resistance to a fungal disease due to expression of the recombinant DNA construct. Furthermore, use of grain or seed produced by a genetically modified crop plant of the invention includes it use in the manufacture of a composition, comprising a milled grain composition, an animal fodder, or steam-pelleted animal fodder.

BACKGROUND OF THE INVENTION

Fungal pathogens cause considerable yield and quality losses of economically important crops. *Fusarium* head blight (FHB) or scab is one of the major fungal diseases of the Triticeae family in temperate, and warm humid regions of the world. The disease is linked to several *Fusarium* species, where *F. graminearum* and *F. culmorum* are economically the most relevant. FHB infection causes a significant reduction in crop yield and quality due to shrivelled grains and their contamination with mycotoxins. In the 1990s, FHB epidemics caused an estimated economic loss of 2.7 billion USD in the US alone. *Fusarium* species, causing FHB, produce toxins that belong to the trichothecenes such as Deoxynivalenol (DON), nivalenol (NIV) and their derivatives including 3-acetyldeoxynivalenol (3-ADON), 15-ADON and 4-acetylnivalenol. They also produce mycotoxins such as zearalenone (ZEA), moniliformin, fumonisins and butenolide. Most of these mycotoxins are associated with fungal virulence and cause toxicosis in humans and animals.

FHB management based on the use of resistant cultivars with good agronomic traits would potentially provide a simple and effective control strategy. However, to date, few wheat and barley accessions, or other major crop plants with moderate resistance to FHB have been reported. Resistance to FHB is a quantitative trait, governed by the combined effects of several quantitative trait loci (QTL), epistasis and the environment. A major QTL (Fhb1) on chromosome 3BS and other minor QTL derived from the Chinese cultivar Sumai are the main sources of genetic resistance to FHB in wheat. In contrast, sources of FHB resistance in barley are limited and only provide a modest level of resistance. Due to the polygenic nature of FHB resistance, development of resistant cultivars with suitable agronomic traits is still a challenge. The discovery of antifungal or antitoxin genes provides a potential strategy for the development of FHB resistant cultivars; which may additionally confer resistance to other fungal diseases. Accordingly, the present invention addresses the problem of providing antifungal genes of plant origin that are capable of conferring resistance to FHB caused by *Fusarium*; and other fungal diseases (e.g. *Aspergillus*) when expressed in cereal cultivars, as well as in other crop plants such as legumes and cotton.

SUMMARY OF THE INVENTION

According to a first embodiment, the invention provides a genetically modified crop plant having a recombinant DNA construct stably-integrated into the genome of the crop plant; said construct comprising a gene operably linked to a promoter of heterologous or homologous origin, wherein
  said promoter directs expression of said operably linked gene at least in grain or seed of said plant, and
  said gene comprises a coding sequence encoding a signal peptide N-terminally fused to a polypeptide having aspartic endoprotease activity (EC 3.4.23.12), and wherein the amino acid sequence of said polypeptide has at least 88% identity to a sequence selected from the group consisting of: SEQ ID No.: 4; amino acid residues 30-451 of SEQ ID No: 6; amino acid residues 30-451 of SEQ ID No: 8; amino acid residues 30-451 of SEQ ID No: 10; amino acid residues 28-446 of SEQ ID No: 12, amino acid residues 27-453 of SEQ ID No.: 45; amino acid residues 32-453 of SEQ ID No.: 47 and amino acid residues 29-460 of SEQ ID No.: 49, and
  wherein said crop plant is selected from the group consisting of a cereal, legume and cotton plant, and
  wherein expression of said gene confers enhanced resistance to a fungal disease caused by a species of *Fusarium* and/or *Aspergillus* as compared to a parent crop plant from which said genetically modified crop plant was derived.

The invention further provides genetically modified grain or seed produced by genetically modified cereal plant of the invention.

In a second embodiment, the invention provides a method for producing a genetically modified crop plant of the invention comprising:
  a) transforming one or more cells of a parent crop plant selected from among a cereal, legume or cotton plant with a recombinant DNA construct comprising a gene operably linked to a promoter of heterologous or homologous origin, wherein:
    said promoter directs expression of said operably linked gene in at least grain or seed of said plant, and,
    said gene comprises a coding sequence encoding a signal peptide N-terminally fused to a polypeptide having aspartyl protease activity (EC 3.4.23.12), and wherein the amino acid sequence of said polypeptide has at least 89% identity to a sequence selected from the group consisting of: SEQ ID No.: 4; amino acid residues 30-451 of SEQ ID No: 6; amino acid residues 30-451 of SEQ ID No: 8; amino acid residues 30-451 of SEQ ID No: 10; amino acid residues 28-446 of SEQ ID No: 12, amino acid residues 27-453 of SEQ ID No.:45; amino acid residues 32-453 of SEQ ID No.:47 and amino acid residues 29-460 of SEQ ID No.:49, and b) selecting transformed crop plant cells, wherein the genome of said cells comprises a copy of said recombinant DNA construct; and c) regenerating a genetically modified crop plant from cells obtained in step (b).

In a third embodiment, the invention provides a method for manufacturing genetically modified grain or seed according to the invention for production of a crop of genetically modified plants which exhibit increased resistance to a fungal disease caused by a species of *Fusarium* and/or *Aspergillus*, said method comprising:

a) screening a population of genetically modified crop plants, according to the present invention, for said recombinant DNA construct, and b) collecting seed from selected plants from step (a).

In a fourth embodiment, the invention provides a method for producing a crop plant exhibiting increased resistance to a fungal disease caused by a species of *Fusarium* and/or *Aspergillus*, said method comprising:

a) obtaining a sample of nucleic acids from a genetically modified crop plant according to the invention, or portion thereof;

b) detecting in said sample the presence of said recombinant DNA construct;

c) breeding a crop plant comprising said recombinant DNA construct with a second crop plant of the same genus to obtain grains or seeds; and d) growing at least one crop plant from said grains or seeds, wherein said crop plant grown from said grains or seeds comprises said recombinant DNA construct; and wherein said recombinant DNA construct comprises a gene operably linked to a promoter of heterologous or homologous origin, wherein said promoter directs expression of said operably linked gene at least in grain of said plant, and said gene comprises a coding sequence encoding a signal peptide N-terminally fused to a polypeptide having aspartyl protease activity (EC 3.4.23.12), and wherein the amino acid sequence of said polypeptide has at least 85% identity to a sequence selected from the group consisting of: SEQ ID No.: 4; amino acid residues 30-451 of SEQ ID No: 6; amino acid residues 30-451 of SEQ ID No: 8; amino acid residues 30-451 of SEQ ID No: 10; amino acid residues 28-446 of SEQ ID No: 12; amino acid residues 27-453 of SEQ ID No.: 45; amino acid residues 32-453 of SEQ ID No.: 47 and amino acid residues 29-460 of SEQ ID No.: 49.

In a fifth embodiment, the invention provides for a use of genetically modified grain or seed produced by a genetically modified crop plant of the invention (for example cereal or legume), for the manufacture of a composition, wherein said composition is any one of:

a. a milled grain or seed composition, b. animal fodder, and c. steam-pelleted animal fodder.

In a sixth embodiment, the invention for use of a genetically modified species of *Gossypium* (for example *Gossypium hirsutum*) for the manufacture of cotton.

DESCRIPTION OF THE INVENTION

Figures

FIG. 1. Cartoon showing (a) the primary sequence annotation and (b) the predicted 3D structure of HvNEP-1 protein, identifying the signal peptide (SP) residues 1 to 29, prodomain (PD), nepenthesin specific insert sequence comprising amino acid residues 151 to 172 (NAP-I), and D116 and D322, the two catalytic aspartic residues within the catalytic pocket (DAS and DPG) and tyrosine flap (Y186) that holds the substrate within the pocket.

Figure 2A:
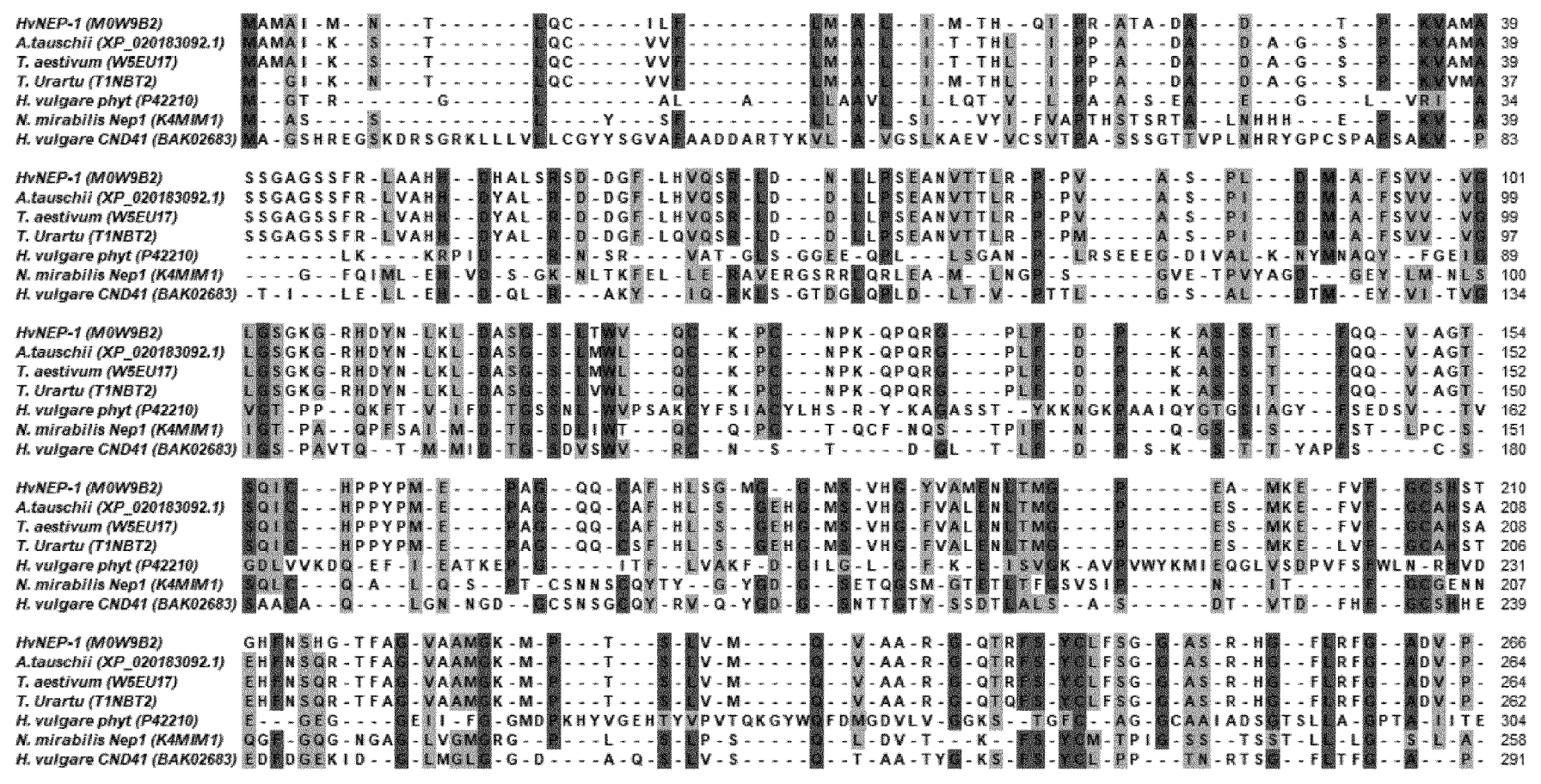
Figure 2B:
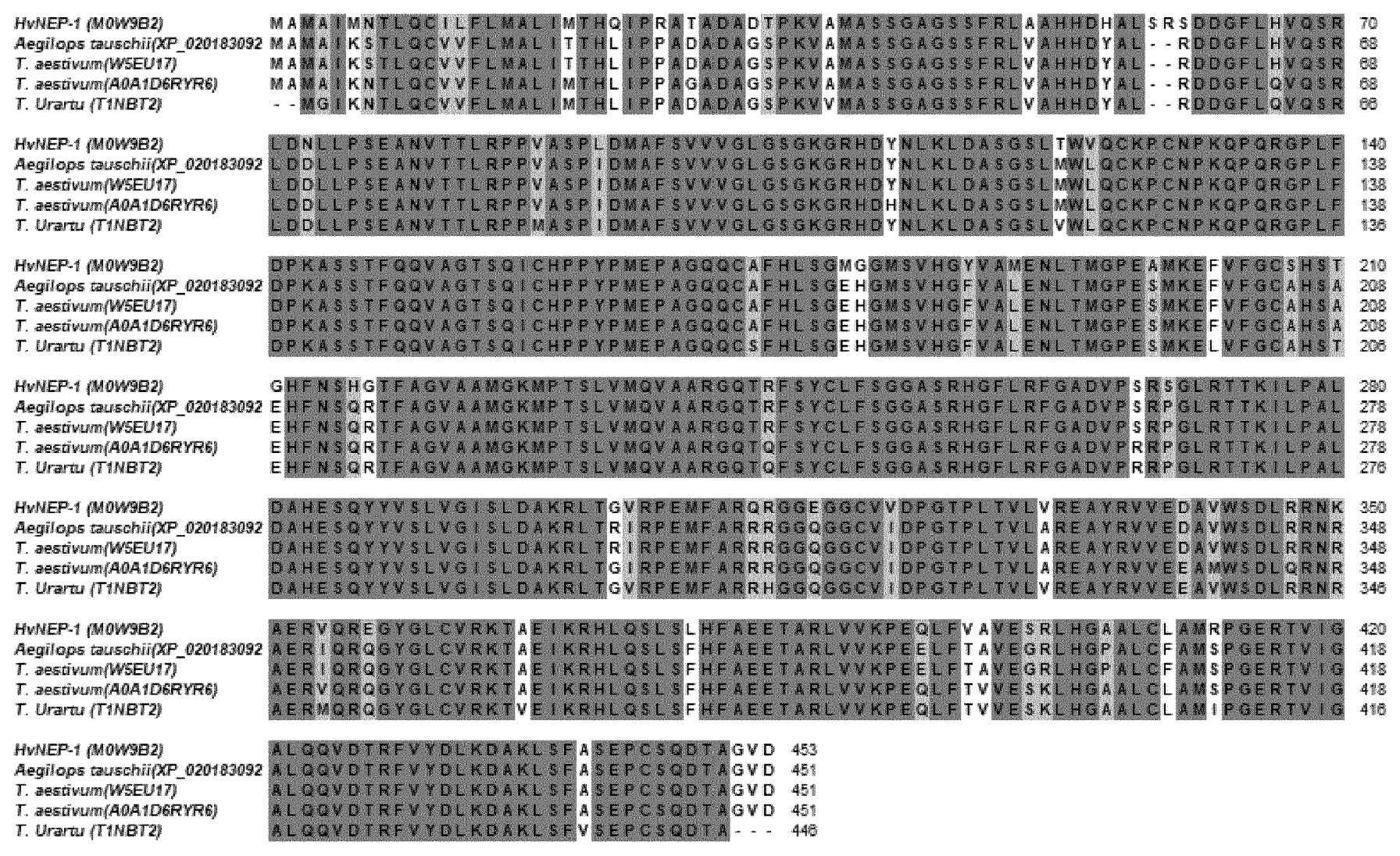

FIG. 2. Multiple sequence alignment of the HvNEP-1 protein and related plant aspartic endoprotease proteins. The sequences in FIG. 2A are: *Hordeum vulgare* nepenthesin 1 (HvNEP-1) (M0W9B2: SEQ ID No.: 2); *Aegilops tauschii* (XP-020183092.1); *Triticum aestivum* (W5EU17); *Triticum urartu* (T1NBT2); *Hordeum vulgare* phytepsin (P42210: SEQ ID No.: 36); *Nepenthes mirabilis* Nep1 (UNIPROT: K4MIM1: SEQ ID No.:37) and *Hordeum vulgare* UNIPROT: CND41 (BAK02683: SEQ ID No.:38). The sequences in FIG. 2B are: *Hordeum vulgare* nepenthesin 1 (HvNEP-1) (M0W9B2); *Aegilops tauschii* (XP-020183092.1); *Triticum aestivum* (W5EU17); *Triticum aestivum* (A0A1D6RYR6); and *Triticum urartu* (T1NBT2). Residues are shaded light gray or dark gray depending on the level of conservation among the sequences FIG. 3 Graphical presentation of HvNEP-1 inhibitory activity, shown as percent inhibition of phytase activity, over (i) a pH range and (ii) a temperature range. The assay comprised 5 µg of HvNEP-1, 2.5 U/ml of *A. ficuum* phytase and 2 mM of sodium phytate substrate, which was incubated for 1 h using the following buffers: pH 2.0 to 2.5, 100 mM formate; pH 3.0 to 5.5, 100 mM acetate; pH 6.0 to 7.0, 100 mM sodium phosphate; pH 8.0, 100 mM Tris-HCl at 37° C. The assay in (ii) was performed using 100 mM acetate buffer pH 5.0, incubated for 1 h. The activity of HvNEP-1 was calculated as percent phytase inhibition, compared to the corresponding sample without HvNEP-1, as controls. Values are mean of 3 independent technical replicates, and error bars represent means±sd of replicates.

Figure 3:
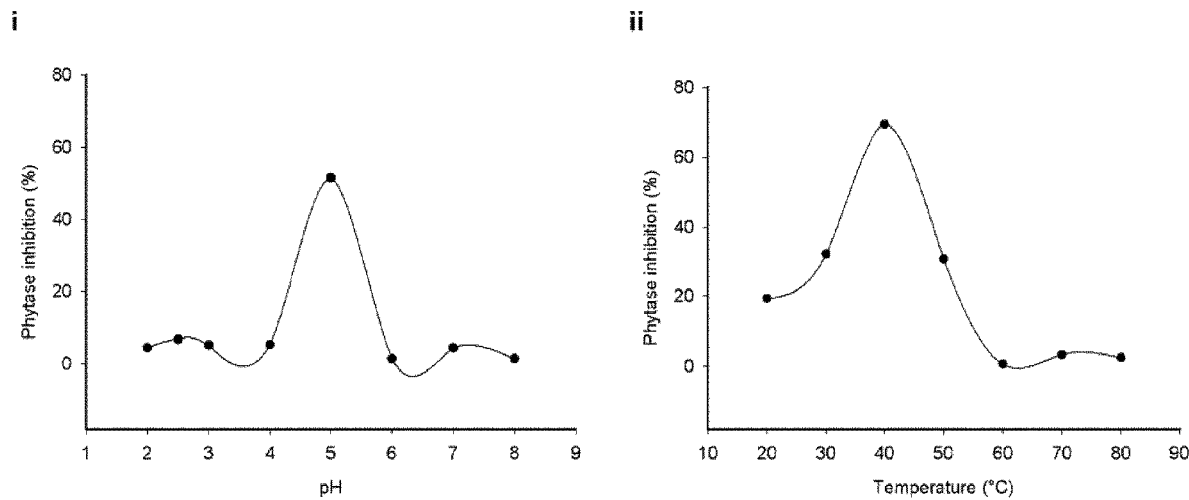
Figure 4:
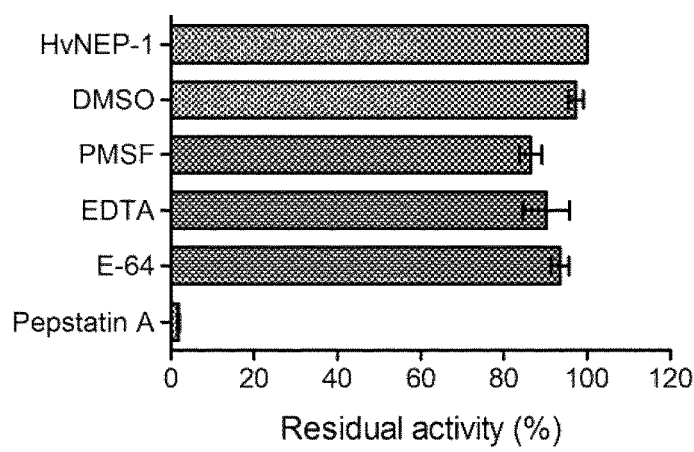

FIG. 4 Graphical presentation (histogram) of the residual inhibitory activity of HvNEP-1 following incubation for 1 h at 37° C. in the presence of the protease inhibitors: E-64 (50 µM), pepstatin A (100 µM), phenylmethylsulfonyl fluoride (PMSF, 1 mM), EDTA (5 mM) and DMSO (3%). Residual inhibitory activity was measured as described in FIG. 3, and percent residual activity was calculated relative to the corresponding sample without protease inhibitor, as control. Values are mean of 3 independent technical replicates, and error bars represent means±sd of replicates.

Figure 5:
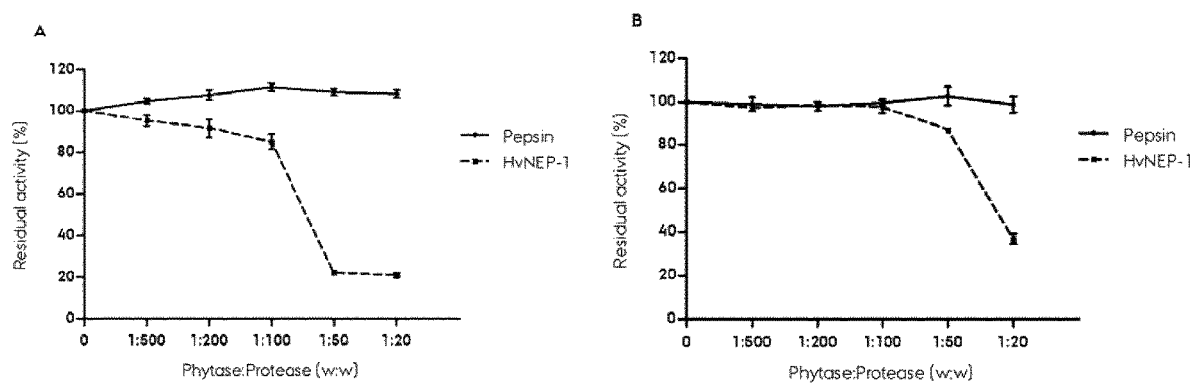

FIG. 5 Graphical presentation of residual phytase activity of *A. ficuum* (A) and TaPAPhy (B) phytases after treatment with the proteases HvNEP-1 or pepsin at different concentration ratios of phytase to protease (w:w). Values are mean of 3 independent technical replicates, and error bars represent means+±sd of replicates.

Figure 6:
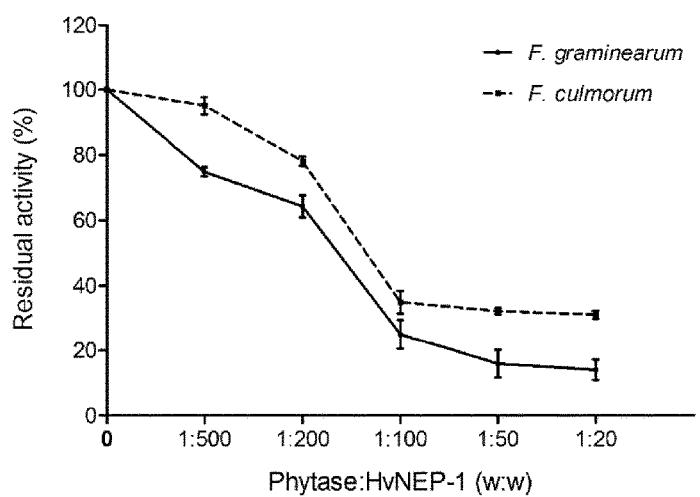

FIG. 6 Graphical presentation of residual phytase activity detected in crude phytase extracts (100 µg) from *F. graminearum* 7775 and *F. culmorum* 8984 measured in the presence of with increasing concentration ratios of HvNEP-1 protease (w:w), using sodium phytate as substrate. Values are mean of 3 independent technical replicates, and error bars represent means+±sd of replicates.

Figure 7:
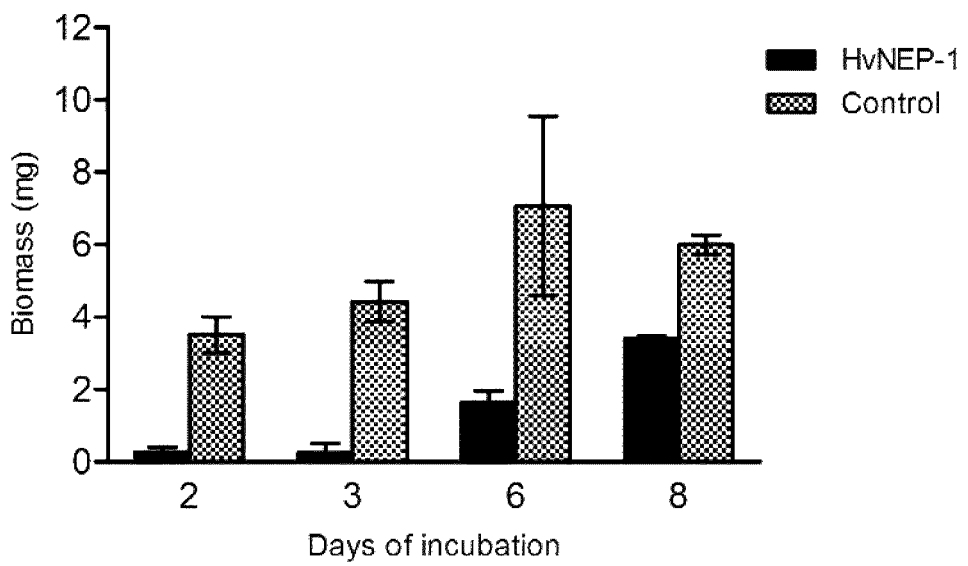

FIG. 7 Graphical presentation of biomass of *F. graminearum* strain JCM 9873 during growth over an 8 day period in the presence or absence of HvNEP-1 protease; values are mean of 3 independent technical replicates, and error bars represent means±sd of replicates.

Figure 8:
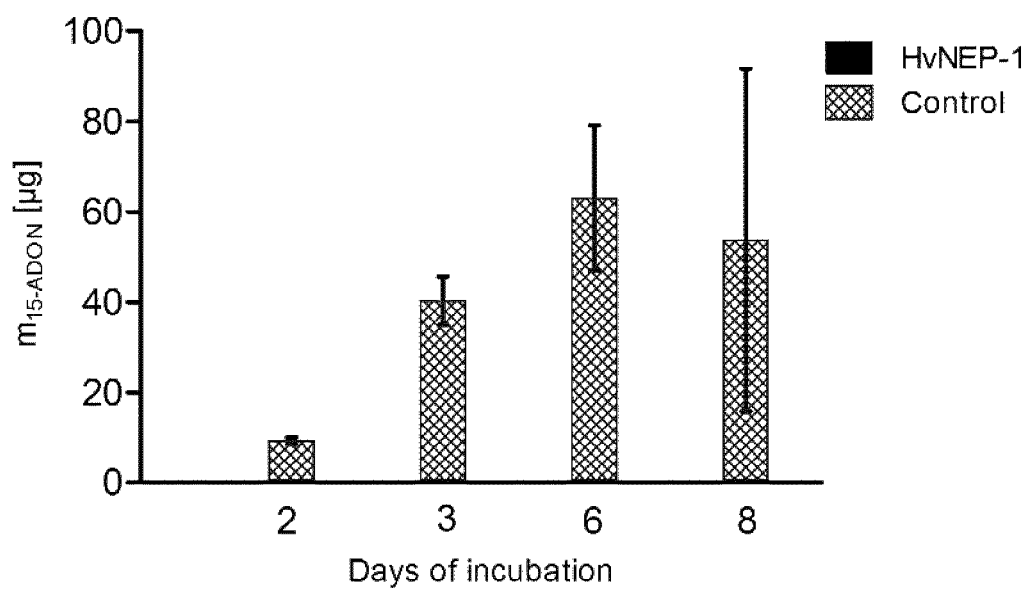

FIG. 8 Graphical presentation of 15-ADON production by *F. graminearum* JCM9873 strain during growth over an 8 day period in the presence or absence of HvNEP-1 protease. In the presence of HvNEP1, 15-ADON production by *F.

graminearum was not detectable. Values are mean of 3 independent technical replicates, and error bars represent means±sd of replicates.

Figure 9:
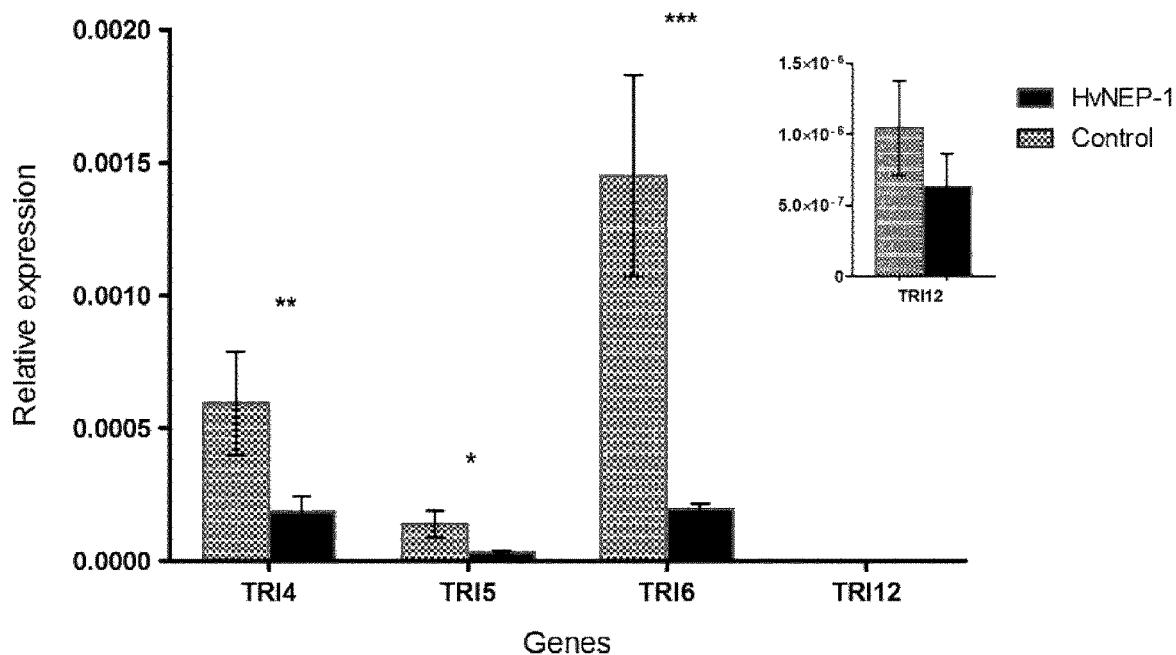

FIG. 9 Graphical presentation of the relative expression levels of TRI genes in *F. graminearum* JCM9873 strain following culture with and without and then detected by qPCR analysis. Gene expression of TRI4, TRI5, TRI6 and TRI12 were normalized using GADPH gene expression levels. The asterisks on the bars represent: significant (*), highly significant () and very highly significant (*) differences in TRI gene expression with and without HvNEP-1 protease.

Figure 10:
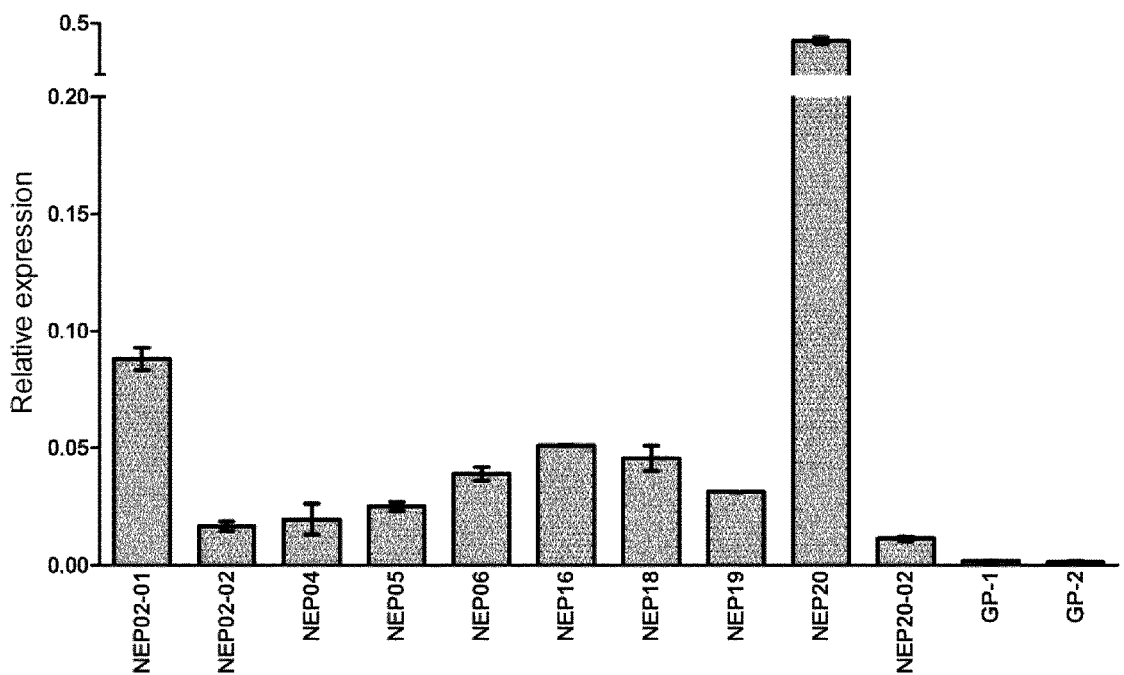

FIG. 10 Graphical presentation of the relative HvNEP-1 protease expression levels, in selected HvNEP-1 transgenic barley lines determined by RT-PCR analysis. The selected lines are transformed with a gene construct comprising a D-hordein promoter operably linked to a gene encoding a D-hordein signal peptide fused to ΔHvNEP-1 having an C-terminal KDEL sequence, operably linked to a NOS terminator. Values are mean of three independent technical replicates, and error bars represent means±sd.

Figure 11:
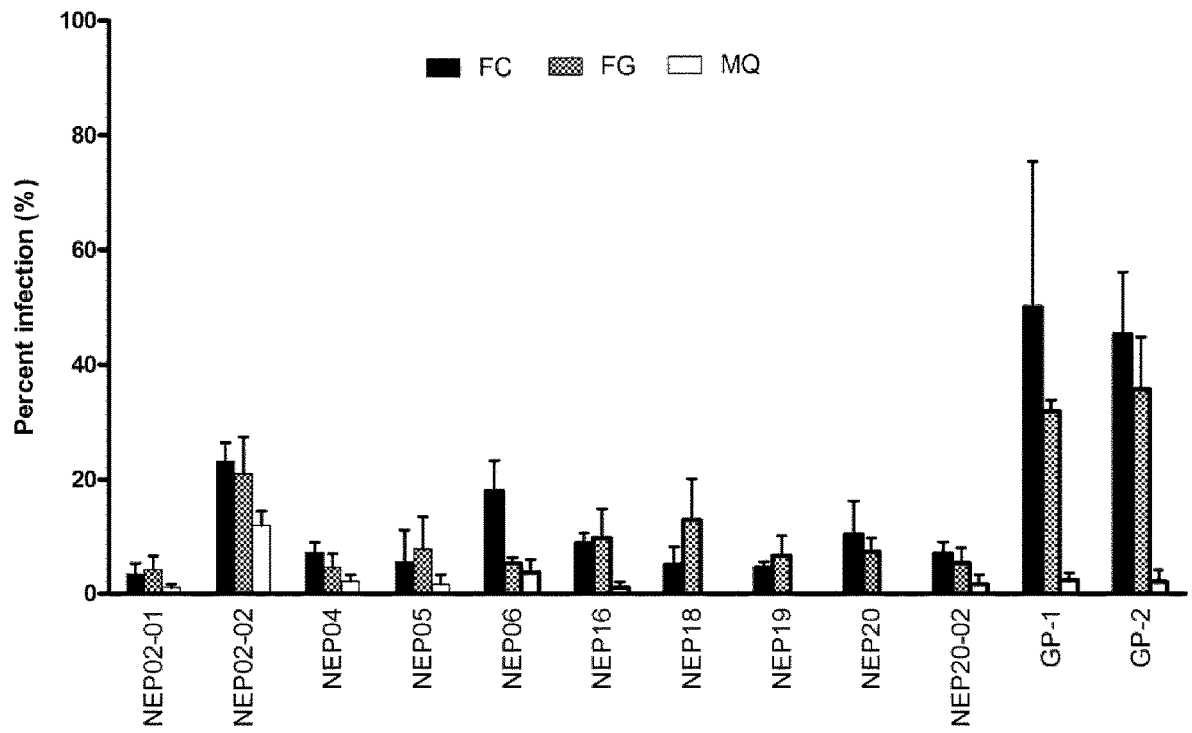

FIG. 11 Graphical presentation of the percent infection of selected HvNEP-1 transgenic barley lines scored 3 weeks after inoculation with either spores of *F. graminearum* (FG) or *F. culmorum* (FC) spores, or inoculated with water control (MQ). Values are mean of three independent technical replicates, and error bars represent means±sd.

Figure 12:
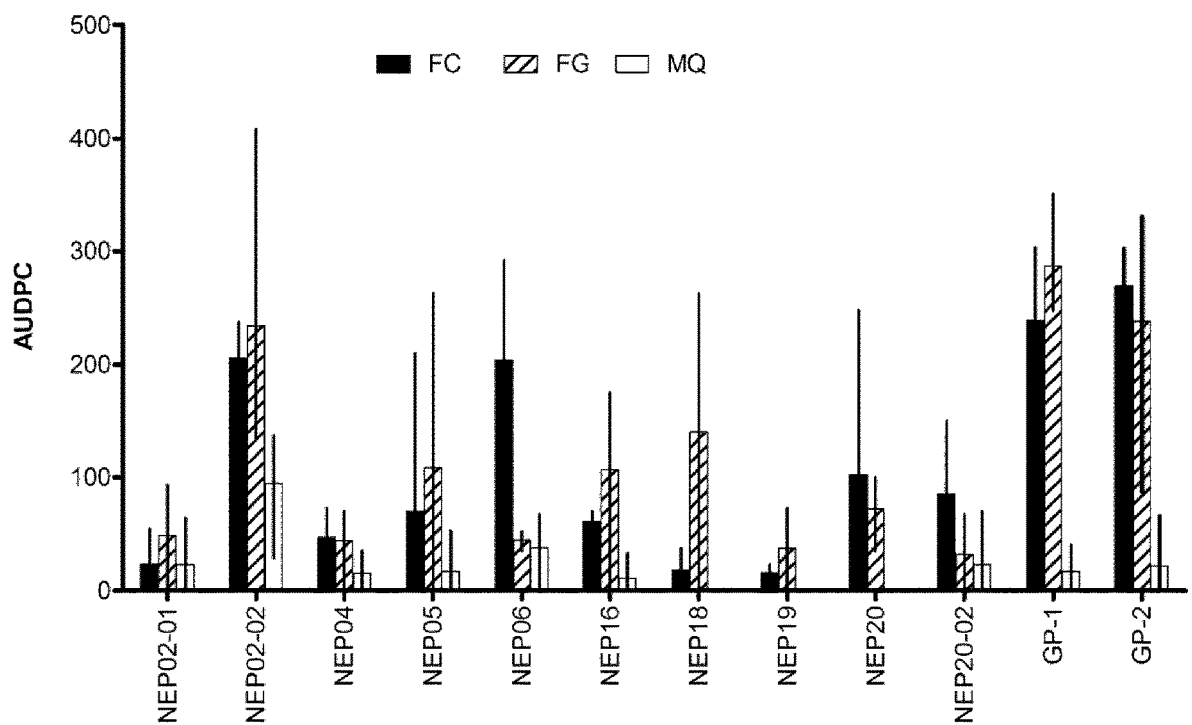

FIG. 12 Graphical presentation of the AUDPC (area under disease progress curve) analysis of selected HvNEP-1 transgenic barley lines scored 3 weeks after inoculation with either spores of selected HvNEP-1 transgenic barley lines scored 3 weeks after inoculation with either spores of *F. graminearum* (FG) or *F. culmorum* (FC) spores, or inoculated with water control (MQ). (FG) or *F. culmorum* (FC) spores, or inoculated with water control (MQ). The minimum and maximum AUDPC per treatment are indicated with error bars.

FIG. 13 tabulates the levels of deoxynivalenol (DON), nivalenol (NIV) and zearalenone (ZON) mycotoxins detected in selected HvNEP-1 transgenic barley lines scored 3 weeks after inoculation with either spores of *F. graminearum* (FG) or *F. culmorum* (FC) spores, or inoculated with water control (MQ). FC+ and FG+ denotes grains showing FHB symptoms, whereas FC− and FG− denotes grains without FHB symptoms with *F. culmorum* (FC) and *F. graminearum* (FG). Detection limits for DON, NIV and ZEA are >50 µg, >50 µg and >5 µg per kg of DW, respectively.

Figure 14:
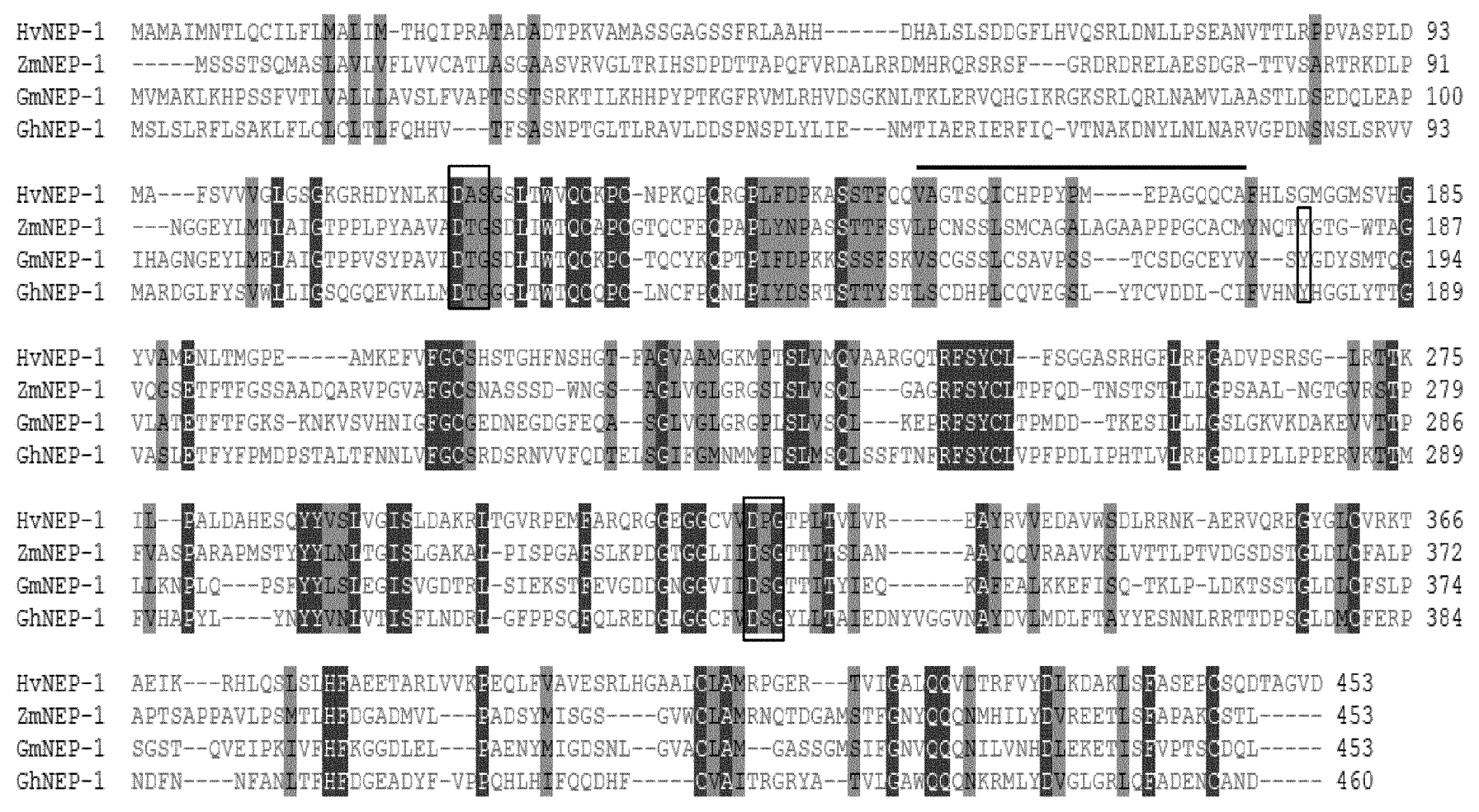

FIG. 14. Multiple sequence alignment of the *H. vulgare* nepenthesin-1 protein (HvNEP-1) from *Hordeum vulgare* and NEP-1 proteins encoded by NEP-1 orthologues from *Zea mays, Glycine max* and *Gossypium hirsutum*. The aligned sequences are: HvNEP-1 (UNIPROT: M0W9B2; SEQ ID No.: 2); ZmNEP-1 (protein ID: XP_008668084.1; SEQ ID No.:45); GmNEP-1 (protein ID: XP_003523200.1; SEQ ID No.:47); and GhNEP-1 (protein ID: XP_016704203.1; SEQ ID No.:49). Residues of the catalytic triads (D[A/T][S/G]) and (D[P/S]G) are boxed, the tyrosine flap (Y) is boxed; the position of the NEP-I "insert" sequence, ([V/L] . . . [A/M/V/I]) characterised by 4 cysteine residues in the orthologue-encoded NEP-1s, is indicated by a solid line.

ABBREVIATIONS AND TERMS gi number: (genInfo identifier) is a unique integer which identifies a particular sequence, independent of the database source, which is assigned by NCBI to all sequences processed into Entrez, including nucleotide sequences from DDBJ/EMBL/GenBank, protein sequences from SWISS-PROT, PIR and many others Amino acid sequence identity: The term "sequence identity" as used herein, indicates a quantitative measure of the degree of homology between two amino acid sequences of substantially equal length. The two sequences to be compared must be aligned to give a best possible fit, by means of the insertion of gaps or alternatively, truncation at the ends of the protein sequences. The sequence identity can be calculated as ((Nref−Ndif)100)/(Nref), wherein Ndif is the total number of non-identical residues in the two sequences when aligned and wherein Nref is the number of residues in one of the sequences. Sequence identity can alternatively be calculated by the BLAST program e.g. the BLASTP program (Pearson W. R. and D. J. Lipman (1988) (ncbi.nlm.nih.gov/cgi-bin/BLAST). In one embodiment of the invention, alignment is performed with the sequence alignment method ClustalW with default parameters as described by Thompson J., et al 1994, available at ebi.ac.uk/clustalw/.

Preferably, the numbers of substitutions, insertions, additions or deletions of one or more amino acid residues in the polypeptide as compared to its comparator polypeptide is limited, i.e. no more than 1, 2, 3, 4, 5, 6, 7, 8, 9, or 10 substitutions, no more than 1, 2, 3, 4, 5, 6, 7, 8, 9, or 10 insertions, no more than 1, 2, 3, 4, 5, 6, 7, 8, 9, or 10 additions, and no more than 1, 2, 3, 4, 5, 6, 7, 8, 9, or 10 deletions. Preferably the substitutions are conservative amino acid substitutions: limited to exchanges within members of group 1: Glycine, Alanine, Valine, Leucine, Isoleucine; group 2: Serine, Cysteine, Selenocysteine, Threonine, Methionine; group 3: proline; group 4: Phenylalanine, Tyrosine, Tryptophan; Group 5: Aspartate, Glutamate, Asparagine, Glutamine.

Cereal plant: is a member of the Family Poaceae; this family encompassing the tribe Triticeae, as well as other members include the genus *Oryza* (e.g. *Oryza sativa*), *Zea* (e.g. *Zea mays*) and *Sorghum* (e.g. *Sorghum bicolor*). The tribe Triticeae encompasses the genus *Triticum* (e.g. *Triticum aestivum*) and *Hordeum* (e.g. *Hordeum vulgare*).

Heterologous promoter: a promoter is a region of DNA that initiates transcription of an operatively-linked gene. A heterologous promoter is a promoter of heterologous origin with respect to the gene to which it is operatively-linked, which is a promoter having a nucleic acid sequence and function that is different (heterologous in origin) from the promoter that is operatively-linked to the respective gene in nature.

A heterologous promoter and the gene to which it is operably-linked may originate from the genome of a common plant of origin. In this case, when an individual member of the plant of origin is transformed with a DNA fragment comprising said heterologous promoter operably-linked to said gene, the resulting transformed plant is defined as an intragenic plant.

Homologous promoter: is a promoter that is homologous in origin to the gene to which it is operatively-linked; such that a contiguous nucleic acid sequence comprising said promoter and its operatively-linked gene is present at a locus within the genome of a plant of origin. When an individual member of the plant of origin is transformed with a DNA fragment comprising said promoter operably-linked to said gene, the resulting transformed plant is defined as a cisgenic plant.

Native gene: is an endogenous gene present in the genome of a plant found in nature.

Recombinant DNA construct: is a non-natural polynucleotide comprising nucleic acid fragments derived from polynucleotides of different origin that are combined by the use of recombinant DNA technology and whose nucleic acid sequence is not present in the genomes of plants found in nature. The recombinant DNA construct is suitable for insertion into the genome of an organism (e.g. cereal plant genome) by means of transformation. Genes that are stably-integrated into the genome of a host plant are inherited in the progeny produced in subsequent plant generations of the transformed plant.

Spike: is the grain-bearing organ of a cereal plant, which develops on one or more shoots (tillers) that grow after the initial parent shoot grows from a germinating cereal seed.

DETAILED DESCRIPTION OF THE INVENTION

Fungal pathogens of the major crop plants, such as cereals, legumes (e.g. soybean) and cotton, require a source of phosphorous. A key source of phosphorous for such pathogens is phosphorous stored as phytate in the grain or seeds of these crop plants. In cereal grains, phosphorous is also found in a bound form, predominantly (~70%) as phytate stored in the aleurone layer of the grain. In order to access phytate-bound phosphorous in such seeds and cereal grains and successfully establish an infection, a pathogen needs phytase activity. Phytases are often among the palette of secreted enzymes produced by fungal pathogens of the major crop plants, including cereals, legumes and cotton.

Plants have evolved inhibitors of pathogenic microbial enzymes as defence components. The present invention addresses the problem of developing genetically improved crop plants (in particular cereal, legume and cotton plants having enhanced resistance to fungal pathogens, in particular species of *Fusarium* and *Aspergillus*, which is the cause of the major fungal diseases, including *Fusarium* head blight (FHB) or scab in cereals.

I A Genetically Modified Crop Plant of the Invention

The invention provides a genetically modified crop plant, in particular a plant selected from amongst a cereal; a legume (being a member of the family Fabaceae; in particular *Glycine* spp; such as *G. max*, also known as soybean); or a plant of the *Gossypium* (cotton) family (for example the *Gossypium* spp., *G. hirsutum*) plant. In one embodiment the genetically modified crop plant is a cereal belonging to the family Poaceae, in particular a member of the tribe Triticeae or the tribe Andropogoneae.

The genome of the crop plant is genetically modified by introduction of a gene encoding a polypeptide having nepenthesin-1-type aspartic proteinase activity. This polypeptide belongs to a new family of nepenthesin-1-type aspartic endoproteases identified herein that are native to cereal plants (Triticeae and Andropogoneae), as well as legume and cotton plants. Identification is based on structural homology between the polypeptide and the nepenthesin-1 and nepenthesin-2 found in the pitcher fluid of carnivorous plants, in particular the presence of catalytic pocket formed by the catalytic triads (DAS and DPG) and possession of a nepenthesin-specific insert sequence (NAP-I), as detailed in Example 1.3 (FIG. 2, 14). Those members of this new family found in Triticeae share a high degree of structural homology, distinguishing them from other aspartic proteases found in cereals. The polypeptide members of this new family further exhibit some functional properties in common with nepenthesins (EC 3.4.23.12), based on the properties exhibited by one polypeptide member (obtained by recombinant expression in yeast), as detailed in Example 2.3. Accordingly, the catalytic activity of the polypeptide may be classified as belonging to EC 3.4.23.12.

One native member of the nepenthesin-1-type aspartic endoproteases found in the cereal plant, *Hordeum vulgare*, is HvNEP-1. The native *H. vulgare* gene encoding HvNEP-1 (having nucleic acid sequence SEQ ID No: 1), encodes a polypeptide having 453 amino acids (SEQ ID No: 2). The primary amino acid sequence encoded by the native HvNEP-1 gene includes a putative N-terminal signal peptide (amino acid residues 1-29) and a predicted prodomain (amino acid residues 30-80) and a mature protein domain. The primary amino acid sequence of additional members of the new family of nepenthesin-1-type aspartic endoprotease that are native to cereal plants (in particular Triticeae), as well as the crop plants *Glycine max* and *Gossypium hirsutum*, are aligned with the sequence of HvNEP-1 in FIGS. 2B and 14, respectively.

The primary amino acid sequence of a polypeptide having nepenthesin-1-type aspartic endoprotease activity expressed in a genetically modified cereal plant comprises an N-terminal signal peptide that co-translationally targets the expressed polypeptide for transport into the endoplasmic reticulum. The signal peptide is fused to the transported polypeptide comprising a pro-domain and mature domain. The amino acid sequence of the transported polypeptide, having nepenthesin-1-type aspartic proteinase activity, has at least 85, 86, 87, 88, 89, 90, 91, 92, 93, 94, 95, 96, 97, 98, 99 or 100% amino acid sequence identity to amino acid residues 30-451 of SEQ ID No: 2 [HvNEP-1; UNIPROT: M0W9B2] or residues 1-425 of SEQ ID No.: 4. Alternatively, the amino acid sequence of the transported polypeptide, having nepenthesin-1-type aspartic proteinase activity, has at least 85, 86, 87, 88, 89, 90, 91, 92, 93, 94, 95, 96, 97, 98, 99 or 100% amino acid sequence identity to: amino acid residues 30-451 of SEQ ID No: 6 [Ae.tNEP-1; NCBI: XP_020183092.1]; amino acid residues 30-451 of SEQ ID No: 8 [TaNEP-1; UNIPROT: W5EU17_WHEAT]; amino acid residues 30-451 of SEQ ID No: 10 [TaNEP-1; UNIPROT: A0A1D6RYR6_WHEAT); amino acid residues 28-446 of SEQ ID No: 12 [TuNEP-1; UNIPROT: T1NBT2_TRIUA]; and amino acid residues 27-453 of SEQ ID No: 45 [ZmNEP-1; protein ID: XP_008668084.1].

In one embodiment, the N-terminal signal peptide fused to the transported polypeptide is a signal peptide derived from a native cereal grain storage protein. Suitable signal peptides include a D hordein signal peptide having SEQ ID No: 14 (derived from UNIPROT:I6TRS8); C hordein signal peptide having SEQ ID No:16 (derived from UNIPROT: Q41210); a B hordein signal peptide having SEQ ID No:18 (derived from UNIPROT: Q0PIV6), a glutenin signal peptide having SEQ ID No: 20 (derived from UNIPROT: P08488), and a gliadin signal peptide having SEQ ID No:22 (derived from UNIPROT: Q41529). Additionally, a suitable signal peptide include the native signal peptide corresponding to the selected NEP-1 polypeptide; for example the HvNEP-1 signal peptide having SEQ ID No:24; amino acid residues 1-29 of SEQ ID No: 6 [Ae.tNEP-1]; amino acid residues 1-29 of SEQ ID No: 8 [TaNEP-1]; amino acid residues 1-29 of SEQ ID No: 10 [TaNEP-1); amino acid residues 1-27 of SEQ ID No: 12 [TuNEP-1]; and amino acid residues 1-26 of SEQ ID No: 45 [ZmNEP-1; protein ID: XP_008668084.1].

In a further embodiment, the primary amino acid sequence of a polypeptide having nepenthesin-1-type aspartic proteinase activity expressed in a genetically modified cereal plant may include an endoplasmic reticulum (ER)- retention signal fused to the C-terminal of the encoded and expressed polypeptide. Suitable ER-retention signals maybe selected from among a KDEL, SEKDEL and HDEL tag.

In wild-type cereal plants, nepenthesin-1-type aspartic proteinase activity was initially detected in the cereal grain (Example 1). Transformation of wild-type cereal plants with a gene encoding a polypeptide of the invention serves to enhance the level of expression of this gene in the plant and correspondingly to enhance the level of nepenthesin-1-type aspartic proteinase activity. The gene encoding the polypeptide having nepenthesin-1-type aspartic proteinase activity in a genetically modified cereal plant, may be tissue-specifically expressed in a tissue of the cereal grain during grain development or it may be expressed constitutively in both tissues of the cereal grain and other plant parts. In order to obtain grain-specific gene expression, a cereal grain-specific promoter of heterologous origin is cognately fused to the gene encoding the polypeptide. For example, the heterologous promoter may be used to direct tissue-specific expression of the cognate gene of the invention in either the endosperm storage tissue, lemma or aleurone of the grain. Heterologous promoters suitable for directing endosperm-specific expression during development of a cereal grain include a promoter that in nature directs expression of a D hordein gene having SEQ ID No: 25; a C hordein gene having SEQ ID No: 26, B hordein gene having SEQ ID No: 27; a glutenin gene having SEQ ID No: 28, an α-gliadin gene having SEQ ID No: 29, an α-zein gene having SEQ ID No: 50, and a glutelin GluB-1 gene having SEQ ID No: 51. Heterologous promoters suitable for directing aleurone-specific expression during development of a cereal grain include a promoter that in nature directs expression of a LTP1 gene having SEQ ID No: 41. Constitutive promoters include the CaMV35S and ubiquitin promoters [NCBI accession no.: AR287190]. Alternatively, the homologous promoter of the gene encoding a polypeptide of the invention may be used to drive its expression; for example the promoter that in nature directs expression of the HvNEP1 gene having SEQ ID No.: 40.

The genetically modified cereal plant of the invention belongs to the family Poaceae; and may for example be selected from among the genus of Triticum, Hordeum, Secale, Triticale, Sorghum, Zea and Oryza. In particular cereal plant may be a species selected from among Triticum aestivum, Hordeum vulgare, Secale cereale, Oryza sativa, Zea mays and a Triticale hybrid. More particularly, the genetically modified cereal plant of the invention is a species of Triticum or Hordeum.

In one embodiment, the invention provides an intragenic genetically modified cereal plant comprising a recombinant DNA construct integrated into the genome of the cereal plant, where the construct comprises a heterologous promoter operably-linked to a gene encoding a polypeptide having aspartic endoprotease activity (EC 3.4.23.12), and where the heterologous promoter and its operably-linked gene are both derived from the genome of the parent of the genetically modified cereal plant.

In a further embodiment, the invention provides a cis-genic genetically modified cereal plant comprising a recombinant DNA construct integrated into the genome of the cereal plant, where the construct comprises a homologous promoter operably-linked to a gene encoding a polypeptide having aspartic endoprotease activity (EC 3.4.23.12), where the homologous promoter is the native promoter for its operably-linked gene and both are derived from the genome of the parent of the genetically modified cereal plant.

A preferred embodiment of the invention provides a genetically modified species of Hordeum, comprising a recombinant DNA construct, said construct comprising a gene encoding a signal peptide fused to a HvNEP-1 having SEQ ID No: 4; wherein the gene is operably linked to a heterologous promoter having a sequence selected from among SEQ ID No: 25, 26 or 27. Preferably the signal peptide has an amino acid sequence selected from among SEQ ID No: 14, 16 and 18.

A preferred embodiment of the invention provides a genetically modified species of Triticum, comprising a recombinant DNA construct, said construct comprising a gene encoding a signal peptide fused to NEP-1 protein having a sequence selected from among the group: amino acid residues 30-451 of SEQ ID No: 6 [Ae.tNEP-1; NCBI: XP_020183092.1]; amino acid residues 30-451 of SEQ ID No: 8 [TaNEP-1; UNIPROT: W5EU17_WHEAT]; amino acid residues 30-451 of SEQ ID No: 10 [TaNEP-1; UNIPROT: A0A1D6RYR6_WHEAT); amino acid residues 28-446 of SEQ ID No: 12 [TuNEP-1; UNIPROT: T1NBT2_TRIUA]; wherein the gene is operably linked to a heterologous promoter having a sequence of SEQ ID No: 28 or 29. Preferably the signal peptide has an amino acid sequence selected from amino acid residues 1-29 of SEQ ID No: 6 [Ae.tNEP-1]; amino acid residues 1-29 of SEQ ID No: 8 [TaNEP-1]; amino acid residues 1-29 of SEQ ID No: 10 [TaNEP-1); amino acid residues 1-27 of SEQ ID No: 12 [TuNEP-1].

Another preferred embodiment of the invention provides a genetically modified Zea mays, comprising a recombinant DNA construct, said construct comprising a gene encoding a signal peptide fused to a HvNEP-1 having SEQ ID No: 4 or to ZmNEP-1 having amino acid residues 27-453 of SEQ ID No: 45; wherein the gene is operably linked to a heterologous promoter having a sequence selected from among SEQ ID No: 50 or 51. Preferably the signal peptide has an amino acid sequence selected from among SEQ ID No: 14, 16 and 18 or amino acid residues 1-26 of SEQ ID No: 45.

When the genetically modified crop plant is a legume; in particular a spp., of Glycine (such as G. max); the plant is modified to comprise a gene encoding a polypeptide having nepenthesin-1-type aspartic proteinase activity (EC 3.4.23.12). In one embodiment, the amino acid sequence of the polypeptide, having nepenthesin-1-type aspartic proteinase activity, has at least 85, 86, 87, 88, 89, 90, 91, 92, 93, 94, 95, 96, 97, 98, 99 or 100% amino acid sequence identity to amino acid residues 30-451 of SEQ ID No: 2 [HvNEP-1; UNIPROT: M0W9B2] fused to the N-terminal D hordein signal peptide (SEQ ID No.:14). Alternatively, the amino acid sequence of the polypeptide having nepenthesin-1-type aspartic proteinase activity, has at least 85, 86, 87, 88, 89, 90, 91, 92, 93, 94, 95, 96, 97, 98, 99 or 100% amino acid sequence identity to: amino acid residues 1-453 (where the native signal peptide is fused to the mature protein) or 32-453 of SEQ ID No: 47, corresponding to the mature protein [GmNEP-1; protein ID: XP_003523200.1] and fused to a preferred heterologous signal peptide.

When the genetically modified crop plant is a member of the Gossypium family, in particular a spp., of Gossypium (such as G. hirsutum); the plant is modified to comprise a gene encoding a polypeptide having nepenthesin-1-type aspartic proteinase activity (EC 3.4.23.12). In one embodiment, the amino acid sequence of the polypeptide, having nepenthesin-1-type aspartic proteinase activity, has at least 85, 86, 87, 88, 89, 90, 91, 92, 93, 94, 95, 96, 97, 98, 99 or 100% amino acid sequence identity to amino acid residues 30-451 of SEQ ID No: 2 [HvNEP-1; UNIPROT: M0W9B2] fused to the N-terminal D hordein signal peptide (SEQ ID No.:14). Alternatively, the amino acid sequence of the polypeptide having nepenthesin-1-type aspartic proteinase activity, has at least 85, 86, 87, 88, 89, 90, 91, 92, 93, 94, 95, 96, 97, 98, 99 or 100% amino acid sequence identity to: amino acid residues 1-460 (where the native signal peptide is fused to the mature protein) or 29-460 of SEQ ID No: 49 corresponding to the mature protein [GhNEP-1; protein ID: XP_016704203.1] and fused to a preferred heterologous signal peptide. The gene encoding the polypeptide having nepenthesin-1-type aspartic proteinase activity in said genetically modified legume or member of the Gossypium family, may be tissue-specifically expressed in seed tissue during development; or it may be expressed constitutively in both seed tissues and other plant parts. In order to obtain seed-specific gene expression, a seed-specific promoter is cognately fused to the gene encoding the polypeptide.

Suitable promoters for directing seed-specific expression in said genetically modified legume include a promoter having SEQ ID No.: 52 that in nature directs expression of a β-conglycinin; or a promoter having SEQ ID No.: 53 that in nature directs expression of a soyAP1 gene.

Suitable promoters for directing seed-specific expression in said genetically modified member of the Gossypium family (in particular G. hirsutum) include a promoter having SEQ ID No.: 54 that in nature directs expression of a G. hirsutum α-globin A gene; or a promoter having SEQ ID No.: 55 that in nature directs expression of a G. hirsutum storage protein (Gh-sp) gene.

II Fungal Resistance of a Genetically Modified Cereal Plant of the Invention

A genetically modified crop plant (in particular a cereal, legume or cotton plant) comprising a gene that directs enhanced expression of a polypeptide having nepenthesin-1-type aspartic proteinase activity in developing grain or seed of the plant is more resistant to fungal disease than the parent plant from which it was derived by genetic modification.

In particular, the genetically modified crop plant of the invention, exhibits enhanced resistance to infection by Fusarium and preferably both Fusarium and Aspergillus pathogens. Enhanced resistance to pathogen attack by isolates of F. graminearum and F. culmorum is illustrated in respect of genetically modified cereal plants according to the invention in Example 5. In this example, mean percent of infection of developing spikes ranged from 3.41 to 23.08% in genetically modified Hordeum vulgare plants, whereas mean percent infection in spikes of control parent plants ranged from 31.88 to 50% for both F. graminearum and F. culmorum strains. The progression of FHB in the infected spikes over a period of weeks was also reduced in the genetically modified Hordeum vulgare plants as compared to the control plants.

Indications as to the underlying mechanism whereby expression of the nepenthesin-1-type aspartic proteinase in a genetically modified crop plant of the invention enhances fungal resistance are seen from the effect of recombinantly-expressed HvNEP-1 on the growth and toxin production by Fusarium cultivated on controlled growth media. Growth of Fusarium cultures was significantly inhibited when cultured in the presence of HvNEP-1, which mirrors the inhibitory effect on infection by Fusarium and progression of the fungal disease on genetically modified cereal plants expressing HvNEP-1. Importantly, both toxin production and the expression of genes (TRI4, TRI5 and TRI6) required for fungal trichothecene synthesis was inhibited in Fusarium cultures by the presence of HvNEP-1 (as show in Example 3.3). More specifically, the phytase enzymes produced by Fusarium cultures, that play an essential role in releasing phosphate required for Fusarium growth on cereal grains, are strongly inhibited by HvNEP-1 (a shown in Example 3.1). Surprisingly, fungal phytases are more sensitive to inhibition by nepenthesin-1-type aspartic endoprotease of the invention as compared to phytases native to cereal grains (see Example 2). Furthermore, the ability of nepenthesin-1-type aspartic proteinases of the invention to inhibit fungal phytases is not shared by other known aspartic proteases (pepsin) indicating that the nepenthesin-1-type aspartic endoprotease form a distinct and unique class of enzymes, whose substrate selective properties confer resistance to fungal attack.

III Methods for Producing and Detecting a Genetically Modified Crop Plant of the Invention A nucleic acid molecule having a nucleic acid sequence encoding a polypeptide having nepenthesin-1-type aspartic proteinase activity, to be expressed in crop plant of the invention (see section I), may be derived by sequence specific amplification of the corresponding sequence of the native NEP-1 gene from genomic DNA extracted from the respective plant. The nucleic acid molecule can also be produced synthetically, to comprise a coding sequence for the respective polypeptide; and whose nucleotide sequence is preferably optimised for expression in the respective plant. Examples of suitable nucleic acid molecules encoding polypeptides having nepenthesin-1-type aspartic proteinase activity for expression in a crop plant according to the invention is provided in the sequence listing. The nucleic acid molecule, encoding a polypeptide for use in the invention, is operably linked (fused) to cis-regulatory regions comprising a promoter nucleic acid molecule of heterologous origin and preferable also a terminator nucleic acid molecule. The promoter may be constitutive; or preferably a tissue-specific promoter that directs tissue-specific expression in developing grain or seed of the crop plant. When the crop plant is a cereal, preferably the promoter is an endosperm-specific promoter, for example a promoter that drives expression of a storage protein gene native to the cereal plant to be genetically modified. The terminator nucleic acid molecule may similarly be derived from a terminator that terminates expression of a storage protein gene native to the crop plant to be genetically modified; or the terminator can be a CaMV 35S terminator (SEQ ID No.: 30) or a terminator derived from the nopaline synthase gene (SEQ ID No.: 31), isolated from Agrobacterium tumefaciens.

A nucleic acid molecule, encoding a polypeptide for use in the invention, operably linked to cis-regulatory regions, is introduced into a nucleic acid construct (pWBVec8 vector; Gynheung et al., 1988) ensure efficient cloning in E. coli and subsequently Agrobacterium strains, and which make it possible to stably transform the crop plants of the invention. Such vectors include various binary and co-integrated vector systems, which are suitable for the T-DNA-mediated transformation. The vector systems are generally characterized by having at least the vir genes, which are required for Agrobacterium-mediated transformation, and T-DNA border sequences.

Agrobacterium transformation typically involves the transfer of the binary vector carrying the foreign DNA of interest (e.g., pWBVec8 vector) to an appropriate Agrobacterium strain, and may be performed as described by Gynheung et al., (1988). For example, transformation of a parent cereal plant species by recombinant Agrobacterium may be performed by co-cultivation of a suspension of transformed *Agrobacterium* cells with isolated immature cereal grain embryos on a solid selective growth medium following the procedure described by Bartlett et al., (2008) and Holme, et al. (2012). Transformed tissue is regenerated on selectable medium carrying an antibiotic or herbicide resistance marker present between the T-DNA borders of the binary vector.

Positive transformants can be identified by PCR using a 5' primer with binding a site located in the promoter region upstream of the NEP-1 coding sequence and a 3' primer located inside the coding sequence for the nepenthesin-1-type aspartic proteinase; such as to distinguish the inserted gene from a native gene encoding an aspartic proteinase.

Cisgenes in cisgenic plants can be identified using standard southern blot analysis or by means of iPCR (Triglia et al., 1988), where one or more copies of a gene and their respective flanking regions in the genome are amplified, and then compared. In this manner iPCR can be used to distinguish and identify a gene inserted into the genome of a cisgenic genetically modified cereal plant of the invention by transformation and a native copy of the gene in the genome.

III Use of Genetically Modified Crop Plants of the Invention

Genetically modified grain and seeds produced by genetically modified crop plants of the invention have a lower risk of contamination with toxins and mycotoxins due to their enhanced resistance to infection by fungal diseases, in particular *Fusarium* infections. Infection by these fungal diseases is accompanied by the production of toxins belonging to the trichothecenes (e.g. Deoxynivalenol (DON), nivalenol (NIV) and their derivatives including 3-acetyldeoxynivalenol (3-ADON), 15-ADON and 4-acetylnivalenol) and mycotoxins (e.g. zearalenone, moniliformin, fumonisins and butenolide) Since both toxins and mycotoxins carry a health risk when used as feed for animals or for human consumption, there is an advantage in using grain derived from genetically modified cereal plants of the invention. Accordingly, grain or seeds produced by genetically modified crop plants of the invention can be used in the production of animal fodder; processed for human consumption or used for fibre/thread manufacture.

Traditional processing steps performed when using genetically modified cereal grain of the invention include one or more of the following steps:

i. Cleaning/conditioning cereal grain: First the genetically modified grain is cleaned. For example the grain may be passed through magnets and/or metal detectors to remove any metal contamination. Machines can be used to separate any other seeds, stones or dust that may have got mixed with the wheat.

ii. Gristing grain: The cleaned and conditioned grain is blended with other types of grain in different proportions to make different kinds of flour.

The gristed grain passes through special rollers called break rolls. They break each grain into its three parts: cereal grain germ, bran and endosperm. Sieves sift the three separated parts into different streams.

iii Mixing: The bran, germ and endosperm fractions, having been separated out, can optionally be blended, and can be milled to make different types of milled cereal grain composition, such as Wholemeal flour using all parts of the grain; Brown flour contains about 85% of the original grain, but with some bran and germ removed; and White flour is made from the endosperm only.

iv. Steam pelleting: Milled cereal grain composition may be combined with other fodder ingredients in a steam-pelleting machine, where the components are exposed to steam at a temperature of about 80° C.-90° C. for a period of time sufficient to reduce the microbial population to levels safe for animal consumption, and the product is converted to dried pellets.

EXAMPLES

Example 1

Detection, Isolation and Identification of a Fungal Phytase Inhibitor from *Hordeum Vulgare*

Crude protein extract (CPE) was extracted from the grains of barley cv. Invictus, fractionated and analyzed for the ability to inhibit *A. ficuum* phytase, as follows:

1.1 Phytase extraction: The grains (5 g) were ground to a fine powder using a rotary mill (IKA Tube mill control), and grain proteins were extracted in 1:10 (w/v) 25 mM sodium acetate buffer (pH 5.5) containing 0.1 mM $CaCl_2$, by constant shaking (300 rpm) at 25° C. for 1 h. The extract supernatant was collected by centrifugation (3392×g, for 30 minutes at 4° C.), to which ammonium sulfate was added to 60% saturation, and the precipitated proteins were collected by centrifugation (7000×g, 15 min, 259 4° C.). The protein pellet was re-suspended in 50 ml of 25 mM acetate buffer (pH 4.5) and dialyzed against 50 mM Tris-HCl buffer (pH 7.5) overnight. The supernatant was collected by centrifugation (7000×g, 30 min, 4° C.), and concentrated (Vivaspin Turbo 30 kDa cut off). Proteins (>30 kDa) were loaded onto an ÄKTA Fast Protein Liquid Chromatography (FPLC) device equipped with a Superdex G200 column, and the collected FPLC fractions were assessed for *Aspergillus ficuum* phytase inhibition employing the phytase assay described below. Fractions having phytase inhibitory activity were analyzed by Mass Spectrometry (MS) according to Dionisio, G. et al. (2011), to identify the phytase inhibitor amongst the detected proteins.

1.2 Phytase assay: Phytase activity and its inhibition was measured according to an ammonium-molybdate method (Engelen A J, et al., 1994). In brief, 100 µl of FPLC fraction (0±1 mg $ml^{-1}$) was incubated with 10 µl (2.5 U $ml^{-1}$) of *A. ficuum* phytase, 1 mM sodium phytate and 400 µl of 25 mM sodium acetate buffer (pH 5.5) containing 0.1 mM $CaCl_2$, at 37° C. for 1 hour. The reaction was terminated by adding 800 µl of stop solution (20 mM ammonium heptamolybdate, 5 mM ammonium vanadate and 6% nitric acid to the final concentration) to the reaction mixture. After centrifugation (4226×g, 5 min), the absorbance of the supernatant was measured at 415 nm using 96 well plate reader (Epoch, Bio-Tek, USA). The residual phytase activity was determined relative to a blank sample.

1.3 Identity of the candidate phytase inhibitor: MS analysis of the most inhibitory fraction identified peptides from 30 different proteins; of which 4 peptides corresponded to an uncharacterized protein annotated to have aspartyl protease activity (Uniprot: M0W9B2). This candidate inhibitor was estimated by MS to have a molecular weight 48.915 kDa.

A candidate barley gene was predicted from the identified Uniprot accession number (M0W9B2) and tblastN against the barley genomic sequence in the NCBI database and the IPK Barley BLAST server. The candidate gene had an open reading frame (ORF) of 1362 bp encoding a protein of 453 amino acids with a predicted molecular weight of 48.9 kDa. The deduced protein encoded a preproenzyme with a putative signal peptide, a prodomain and a long polypeptide interrupted by the nepenthesin-specific insert sequence (NAP-I) (FIG. 1a). The NAP-I sequence is predicted based on NAP-I sequences described for nepenthesins and homologues (Athauda et al., 2004). Based on the characteristic Nepenthesin aspartic endoprotease (NPAP)-type primary structure organization of the deduced protein it was identified as an HvNEP-1 (i.e. a barley nepenthesin-1-type aspartic endoprotease). The predicted 3D structure of the mature protein displays a catalytic pocket formed by the two catalytic triads (DAS and DPG) supported by Tyr residue (Y186) as a flap (FIG. 1b). Multiple sequence alignment of HvNEP-1 and related aspartic proteases revealed that catalytic Asp residues are conserved but not the flap Tyr. Residues forming the catalytic triads with Asp differ from the characteristic aspartic proteases (DTG/DSG and DTG). Besides, the NAP-I sequence contains two Cys residues rather than four described for most of NPAPs proteins (FIG. 2). The protein showed <20% homology to the nepenthesins from *Nepenthes* species.

Example 2

Cloning, Expression and Properties of the HvNEP-1

2.1 Cloning HvNEP-1 gene: A candidate gene was predicted from the sequence of Uniprot: M0W9B2, and tblastN against the barley genomic sequence in the NCBI database and the IPK Barley BLAST server. Genomic DNA (gDNA) was extracted from the leaves of 6-day old barley cv. Invictus seedlings as described by Doyle et al., 1991. The HvNEP-1 coding sequence, corresponding to encoded amino acid residues 30-453 (minus signal peptide coding sequence; ΔHvNEP-1) was PCR amplified using gDNA as template and gene-specific primers, and Herculase II DNA polymerase, according to the manufacturer's instructions (Invitrogen). The amplified 1.5 kbp DNA fragment was gel purified and cloned into pCRII-TOPO Blunt vector according to the manufacturer's instructions (Invitrogen). Selected clones were evaluated for the insert by restriction digestion, and sequencing (Eurofins Genomics).

2.2 HvNEP-1 gene expression: The ΔHvNEP-1 sequence, further comprising 3' sequence encoding a C-terminal His6 tag, was cloned into the pGAPZaA vector downstream of an alpha mating factor secretion signal coding sequence, using In-fusion (Zhu et al., 2007), under control of the glyceraldehyde-3-phosphate dehydrogenase (GAP) promoter (FIG. 3); and transformed into *Pichia pastoris* strain KM71H. HvNEP-1 protein expression in *Pichia* was confirmed by matrix-assisted laser-desorption ionization time of flight (MALDI-TOF)-mass spectrometry (MS), SDS-PAGE and Western blotting. The levels of HvNEP-1 in the growth media was 1.2 mg/ml. Western blot analysis, using anti His6 mouse monoclonal antibodies (Roche) and and goat anti-mouse IgG alkaline phosphatase conjugate (BioRad, Hercules, Calif.), identified a protein with an approximate size of 92 kDa. The predicted theoretical mass of the truncated HvNEP-1 is 47 kDa, indicating that *Pichia* expressed HvNEP-1 forms a homodimer.

2.3 Properties of HvNEP-1: The enzymatic activity of HvNEP-1 (expressed in *Pichia*), was measured indirectly, by incubating the enzyme in the presence of *Aspergillus ficuum* phytase, as substrate, and then detecting percent inhibition of the phytase activity measured according to Engelen (1994). HvNEP-1 exhibited peak activity for inhibiting *A. ficuum* phytase at pH 5.0 and at temperature 40° C. (FIG. 3).

The sensitivity of HvNEP-1 to protease inhibitors was characteristic of a nepenthesin-1 type aspartic endoprotease. HvNEP-1 was strongly inhibited the protease inhibitor, Pepstatin A (98.2% loss of activity), while PMSF, E-64, EDTA and DMSO inhibited the enzyme activity by 13.5%, 6.4%, 9.7% and 2.7% respectively (FIG. 4).

The substrate selectivity of HvNEP-1 was compared with pepsin (aspartic acid protease on the activity of *A. ficuum* (EC 3.1.3.8) and wheat TaPAPhy phytase (EC 3.1.3.26). Although both fungal and wheat phytases were highly sensitive to HvNEP-1 inhibition (FIG. 5); the sensitivity of fungal phytase was clearly stronger, since residual phytase activity of *A. ficuum* was reduced at phytase: protease ratios of 1:500 (FIG. 5i), while residual TaPAPhy phytase activity was first reduced at phytase: protease ratios of 1:100 (FIG. 5ii). In contrast, both phytases were resistant to pepsin, as phytase activity was unaffected after exposure to pepsin even at phytase: protease ratio of 1:20.

Example 3

HvNEP-1 is an Inhibitor of *Fusarium* Phytases and the Growth and Toxin Production of *Fusarium* Species 3.1 HvNEP-1 inhibits *Fusarium* phytase: HvNEP-1 strongly inhibited phytases in crude extracts derived from *F. graminearum* 7775 and *F. culmorum* 8984. Incubation with HvNEP-1 in a ratio of only 1:500 phytase: HvNEP-1 protease (w/w), at room temperature for 1 h was sufficient to cause inhibition (FIG. 6).

3.3 HvNEP-1 inhibits *Fusarium* growth and toxins production: Antifungal activity of recombinantly-expressed HvNEP-1 against *Fusarium* was analyzed using fungal cultures prepared according to Etzerodt, T. et al. (2015). A composition comprising either HvNEP-1 (3.47 mg) or Ronozyme ProAct serine protease (L) EC 3.4.21.-(supplied by Novozymes) as a control, in 100 µl of 100 mM acetate buffer pH 5.5 were added to 1 ml fungal culture ($10^7$ spores/ml) on day 1 and again on 2 day of incubation with shaking (22° C., 130 rpm) for 2, 3, 6 and 8 days. On the respective days, mycelial mass was collected by centrifugation (max speed for 20 min), freeze dried and weighed. Toxin profiles were analyzed according to Etzerodt, T. et al. (2015). Expression of genes involved in fungal trichothecene synthesis were analysed by extracting total RNA from mycelial mass, harvested after 10 days culture (Chomczynski et al. 2006). RNA samples were treated with DNase (Roche) and reverse transcribed using Superscript III-RT (Invitrogen) and oligo (dT) 21T-anchor containing primer. Reverse transcripts of the coding sequences TRI4 [XM_011323872.1; SEQ ID No.:32], TRI5 [XM_011323870.1; SEQ ID No.: 33], TRI6 [encoding GenBank: CEF78358.1] and TRI12 [encoding GenBank: ANO39668.1] were quantified by qPCR (6 µl Power SYBR Green master mix (Applied Biosystems), 1 µl diluted cDNA, 2.4 µl of µM primer mix and 2.6 µl sterile Milli Q water), in a final volume of 12 µL; and products detected in an AB7900HT sequence detection system (Applied Biosystems).

HvNEP-1 strongly inhibited both growth and toxin production, as seen by the reduction in biomass accumulation in the fungal cultures over a period of 8 days incubation (FIGS. 7 and 8). The expression of TRI4, TRI5 and TRI6 genes were suppressed by HvNEP-1, (FIG. 9), in particular TRI6, whose suppression was highly significant.

Example 4

HvNEP-1 Overexpressing *Hordeum Vulgare* Lines

Transgenic *Hordeum vulgare* lines expressing an HvNEP-1 gene were obtained by *Agrobacterium*-mediated transformation, as follows:

4.1 HvNEP-1 gene transformation vector construction: The HvNEP-1 coding sequence [SEQ ID No.:3] encoding ΔHvNEP-1 (lacking the native HvNEP-1 signal peptide) was PCR amplified from *Hordeum vulgare* gDNA. PCR amplification was used engineer a nucleic acid sequence encoding a fusion protein comprising an N-terminal HordD signal peptide [SEQ ID No.: 14] and a C-terminal SEKDEL [SEQ ID No.: 39] serving as an endoplasmic reticulum (ER) sorting sequence. The nucleic acid sequence encoding this HvNEP-1 fusion protein was fused downstream of a HordD promoter [SEQ ID No.:25] and inserted upstream of the *Agrobacterium tumefaciens*-derived NOS terminator [SEQ ID No.: 31] in the transformation vector pWBVec8 (Gynheung et al., 1988).

4.2 Generation of HvNEP-1 transgenic *Hordeum vulgare* lines: The HvNEP-1 transformation vector construct was introduced into competent *Agrobacterium* strain AGL0, as described Gynheung et al., (1988). Transformants were selected by growth on LB plates containing 100 μg/ml spectinomycin and 25 μg/ml Rifampicin for 72 h at 28° C.; and positive colonies were identified by PCR. Positive clones were cultured in MG/L medium ((5 g/l Mannitol, 1 g/l L-glutamic acid, 0.25 g/l $KH_2PO_4$, 0.1 g/l NaCl, 0.1 g/l $MgSO_4*7H_2O$, 1 ng/l Biotin, 5 g/l Tryptone, 2.5 g/l Yeast extract) containing 100 μg/ml spectinomycin and 25 μg/ml Rifampicin and then used for immature barley embryo transformation following the procedure described by Bartlett et al., (2008) and Holme, et al. (2012).

Following transformation, selection and regeneration of T0 plants, gDNA was isolated from young leaves (according to Doyle et al., 1991); and selection of positive transformants was confirmed by PCR using forward and reverse primers [SEQ ID No.: 34 and 35] with binding sites inside the HordD promoter and the HvNEP-1 gene yielding a PCR fragment of 759 bp.

Twenty HvNEP-1 transgenic lines (T0 generation) showed detectable HvNEP-1 expression, the highest expression was seen in line NEP20 (0.4166), the lowest in line NEP20-02(0.0114) (FIG. 10) relative to un-transformed lines (GP).

Example 5

Transgenic HvNEP-1 *Hordeum vulgare* Lines Exhibit *Fusarium* Resistance

*Fusarium*-infected HvNEP-1 transgenic lines were assessed for *Fusarium* Head Blight (FHB) resistance and mycotoxin accumulation at the 85-87 growth stage (according to Zadoks scale (Zadoks, et al., 1974)).

5.1 *Fusarium* infection: Spore suspensions of *F. graminearum* 7775 and *F. culmorum* 8984 isolates, having a DON chemotype, were prepared according to Etzerodt, T. et al. (2015). Each spore suspension ($1\times10^5$ spores per ml in water, containing 0.04% tween 20) was used to spray-inoculate spikes of T0 HvNEP-1 transgenic lines 8 weeks of germination (Zadoks stages 60). Control spikes were sprayed with MQ water. Untransformed golden promise (GP) plants at the same stage of development were treated similarly with the *Fusarium* spore suspensions and MQ water. The inoculated and mock-inoculated plants were covered with plastic bags and cultivated in a controlled environment (18-21° C. and relative humidity 70-75%). FHB disease severity of 10 T0 transgenic lines was compared to untransformed *Hordeum vulgure* cv Golden Promise (GP) plants, and scored as percentage of infected seeds in the first 3 matured spikes in each plant at 1, 2 and 3 weeks after inoculation.

5.2 Disease severity: Disease scoring showed a substantial reduction in FHB severity in HvNEP-1 transgenic lines (FIG. 11) whose mean percent of infection ranged from 3.41 to 23.08%, whereas mean percent infection in the control GP plants were ranging from 31.88 to 50% for both *F. graminearum* and *F. culmorum* strains. The progression of FHB in the spikes of transgenic lines and control GP plants was assessed for the first three weeks after inoculation, and AUDPC (area under disease progress curve) calculated (FIG. 12). The mean AUDPC of FHB progress was higher in the control GP barley plants than in the HvNEP-1 transgenic lines.

5.3 Mycotoxin production: Mycotoxin levels detected following inoculation with spores of *F. graminearum* or *F. culmorum* strains showed a general reduction in mycotoxin production in HvNEP-1 transgenic lines as compared to control GP barley plants (FIG. 13).

Example 6 Cloning and transgenic expression of HvNEP-1 and its orthologue genes in maize (*Zea mays*), soybean (*Glycine max*) and cotton (*Gossypium hirsutum*)

2.1 Cloning *Zea mays*, ZmNEP-1 cDNA: mRNA is extracted from leaves of *Zea mays* seedlings and used to generate cDNA as described by Yockteng et al (2013). The ZmNEP-1 cDNA has NCBI Ref sequence number: XM_008669862.2, and comprises a coding sequence for the ZmNEP-1 protein having protein ID: XP_008668084.1. A DNA sequence comprising the coding sequence for ZmNEP-1 having amino acid residues 1-453 [SEQ ID No.: 45]; and the mature protein having amino residues 27-453 [SEQ ID No.:45], are PCR amplified using cDNA as template and gene-specific primers, and Herculase II DNA polymerase, according to the manufacturer's instructions (Invitrogen). The amplified DNA fragment is gel purified and cloned into pCRII-TOPO Blunt vector according to the manufacturer's instructions (Invitrogen). Selected clones are evaluated for the insert by restriction digestion, and sequencing (Eurofins Genomics).

2.2 Cloning *Glycine Max* GmNEP-1 Gene

Genomic DNA (gDNA) was extracted from the leaves of *G. max* seedlings as described by Doyle et al., 1991. The GmNEP-1 gene has Gene ID: 100811294 in NCBI Ref sequence number: NC_016091.3, and comprises a coding sequence for the GmNEP-1 protein having NCBI Reference Sequence: XP_003523200.1. A DNA sequence comprising the coding sequence for GmNEP-1 having amino acid residues 1-453 [SEQ ID No.: 47]; and the mature protein having amino residues 32-453 [SEQ ID No.:47], are PCR amplified using gDNA as template and gene-specific primers, and Herculase II DNA polymerase, according to the manufacturer's instructions (Invitrogen). The amplified DNA fragments are gel purified and cloned into pCRII-TOPO Blunt vector according to the manufacturer's instructions (Invitrogen). Selected clones are evaluated for the insert by restriction digestion, and sequencing (Eurofins Genomics).

2.3 Cloning *Gossypium Hirsutum* GhNEP-1

Genomic DNA (gDNA) was extracted from the leaves of *G. hirsutum* seedlings as described by Doyle et al., 1991. The GhNEP-1 gene has Gene ID: 107919204 in NCBI Ref sequence number: NC_030097.1, and comprises a coding sequence for the GhNEP-1 protein having NCBI Reference Sequence: XP_016704203.1. A DNA sequence comprising the coding sequence for GhNEP-1 having amino acid residues 1-460 [SEQ ID No.:49]; and the mature protein having amino residues 29-460 [SEQ ID No.:49], are PCR amplified using gDNA as template and gene-specific primers, and Herculase II DNA polymerase, according to the manufacturer's instructions (Invitrogen). The amplified DNA fragments are gel purified and cloned into pCRII-TOPO Blunt vector according to the manufacturer's instructions (Invitrogen). Selected clones are evaluated for the insert by restriction digestion, and sequencing (Eurofins Genomics).

2.4 Transgenic Constructs and Their Transformation and Expression in *Zea Mays, Glycine Max* and *Gossypium Hirsutum*

The nucleic acid sequences encoding each of the proteins: ZmNEP-1, GmNEP-1 and GhNEP-1 are each fused downstream of a seed-specific promoter and inserted upstream of the *Agrobacterium tumefaciens*-derived NOS terminator [SEQ ID No.: 31] in the transformation vector pWBVec8 (Gynheung et al., 1988). The seed-specific promoters used are as follows:

α-zein gene promoter [SEQ ID No.:50] for expression in *Z. mays;*

β-conglycinin gene promoter [SEQ ID No.:52] for expression in *G. max;*

α-globin A gene promoter [SEQ ID No.:54] for expression in *G. hirsutum.*

For *Z. mays* transformation, the vector, comprising the respective ZmNEP-1 expression construct, is transformed into competent *Agrobacterium* strain AH101, which is introduced into *Z. mays* embryos as described Ishida Y et al., (2007).

For *G. max* transformation, the vector, comprising the respective GmNEP-1 expression construct, is transformed into competent *Agrobacterium* strain AH101, which is introduced into *G. max* embryos as described Li et al., (2007).

For *G. hirsutum* transformation, the vector, comprising the respective GhNEP-1 expression construct, is transformed into competent *Agrobacterium* strain LBA4404, which is introduced into *G. hirsutum* hypocotyl segments as described Firoozabady E et al., (1987).

Positive transformants are detected by PCR using gene specific primers; and selected transformants are cultured to regenerate plants.

2.5 Screening Transformants for Fungal Disease Resistance

For *Z. mays*, ears are selected and inoculated at early silking stage with an inoculum of *Fusarium graminearum* and *Aspergillus niger* spores ($5\times10^5$ spores/ml), and disease severity is evaluated after 3-4 weeks of humid growth conditions using a 7-class rating scale as described by Reid L M et al., (2002).

For *G. max*, seeds from positive $T_0$ transformants are inoculated with spores of *F. graminearum* and assessed for disease severity as described in Ellis M L, et al., (2011). In addition transgenic seeds are examined for the seed-borne pathogens, among *Aspergillus* species, as described in Boue et al. (2005). For *G. hirsutum*, transgenic plants are inoculated with spores from *Aspergillus* and *Fusarium* species and then assessed for resistance according to Doan H K et al (2015).

REFERENCES

Athauda, S. B. P. et al., (2004) Enzymic and structural characterization of nepenthesin, a unique member of a novel subfamily of aspartic proteinases. Biochemical Journal 381, 295-306.

Bartlett, J. G., Alves, S. C., Smedley, M., Snape, J. W. & Harwood, W. A. (2008) High-throughput *Agrobacterium*-mediated barley transformation. Plant Methods 4.

Boue S A, Shih B Y, Carter-Wientjes C H, Cleveland T E (2005): Effect of soybean lipoxygenase on volatile generation and inhibition of *Aspergillus flavus* mycelial growth. Journal of Agricultural and Food Chemistry, 53(12):4778-4783.

Chomczynski, P. & Sacchi, N. (2006) The single-step method of RNA isolation by acid guanidinium thiocyanate-phenol-chloroform extraction: twenty-something years on. Nature Protocols 1, 581-585.

Dionisio, G. et al., (2011) Cloning and Characterization of Purple Acid Phosphatase Phytases from Wheat, Barley, Maize, and Rice. Plant Physiology 156, 1087-1100.

Doan H K, Davis R M (2015): Efficacy of seed treatments on viability of *Fusarium oxysporum f.* sp vasinfectum race 4 in infected cotton seed. Crop Protection, 78:178-184.

Doyle et al., (1991) DNA protocols for plants in "Molecular Techniques in Taxonomy" part to of NATO ASI Series volume 57: 283-293

Ellis M L, Broders K D, Paul P A, Dorrance A E (2011): Infection of Soybean Seed by *Fusarium graminearum* and Effect of Seed Treatments on Disease Under Controlled Conditions. Plant Disease, 95(4):401-407.

Engelen A J, Vanderheeft F C, Randsdorp P H G, Smit E L C (1994) Simple and rapid-determination of phytase activity. Journal of Aoac International 77: 760±764. PMID: 8012231

Etzerodt, T. et al. (2015) 2,4-Dihydroxy-7-methoxy-2H-1,4-benzoxazin-3(4H)-one (DIMBOA) inhibits trichothecene production by *Fusarium graminearum* through suppression of Tri6 expression. International Journal of Food Microbiology 214, 123-128.

Firoozabady E, Deboer D L, Murray E E, Merlo D J, Adang M J, Halk E L (1987): Transformation of cotton (*Gossypium-hirsutum*-L) by *agrobacterium*-tumefaciens and regeneration of transgenic plants. In Vitro Cellular & Developmental Biology, 23(3):A67-A67

Gynheung An, P. R. E., Amitava Mitra and Sam B. Ha Binary vectors. (1988) Plant molecular biology manual, Vol. 1.

Holme, I. B. et al. (2012) Cisgenic barley with improved phytase activity. Plant Biotechnology Journal 10, 237-247.

Ishida Y, Hiei Y, Komari T (2007): *Agrobacterium*-mediated transformation of maize. Nature Protocols, 2(7):1614-1621

Jia Y Y, Yao X D, Zhao M Z, Zhao Q, Du Y L, Yu C M, Xie F T (2015): Comparison of Soybean Transformation Efficiency and Plant Factors Affecting Transformation during the *Agrobacterium* Infection Process. International Journal of Molecular Sciences, 16(8):18522-18543

Reid L M, Woldemariam T, Zhu X, Stewart D W, Schaafsma A W (2002): Effect of inoculation time and point of entry on disease severity in *Fusarium graminearum, Fusarium verticillioides*, or *Fusarium subglutinans* inoculated maize ears. Canadian Journal of Plant Pathology-Revue Canadienne De Phytopathologie, 24(2):162-167.

Triglia, T, Peterson M. G., and Kemp D J, (1988) A procedure for in vitro amplification of DNA segments that lie outside the boundaries of known sequences. Nucleic Acids Research 16(16): 8186.

Yockteng, R., A method for extracting high-quality RNA from diverse plants for next-generation sequencing and gene expression analyses. Appl Plant Sci. 2013 December; 1(12): apps.1300070.

Zadoks, J. C., Changi, T. T. & Konzak, C. F. (1974) A decimal code for the growth stages of cereals Weed Research 14, 415-421.

Zhu, B., Cai, G., Hall, E. O. & Freeman, G. J. In-fusion assembly: seamless engineering of multidomain fusion proteins, modular vectors, and mutations. BioTechniques 43, 354-359 (2007).

The invention claimed is:

1. A genetically modified crop plant having a recombinant DNA construct integrated into the genome of the crop plant; said construct comprising a polynucleotide operably linked to a heterologous promoter, wherein:
   i. said heterologous promoter directs developing seed-specific or developing grain-specific expression of said operably linked polynucleotide, and
   ii. said polynucleotide comprises a coding sequence encoding a signal peptide N-terminally fused to a polypeptide having aspartic endoprotease activity (EC 3.4.23.12), and wherein the amino acid sequence of said polypeptide has at least 88% sequence identity to a sequence selected from the group consisting of: SEQ ID No.: 4; amino acid residues 30-451 of SEQ ID No: 6; amino acid residues 30-451 of SEQ ID No: 8; amino acid residues 30-451 of SEQ ID No: 10; amino acid residues 28-446 of SEQ ID No: 12; amino acid residues 27-453 of SEQ ID No.: 45; amino acid residues 32-453 of SEQ ID No.: 47 and amino acid residues 29-460 of SEQ ID No.: 49,
wherein expression of said polynucleotide confers enhanced resistance to a fungal disease caused by a species of *Fusarium* and/or *Aspergillus* as compared to a parent plant lacking said construct from which said genetically modified crop plant was derived.

2. The genetically modified crop plant of claim 1, wherein the plant is a cereal; and
   wherein the nucleotide sequence of said heterologous promoter is selected from the group consisting of: SEQ ID No: 25; SEQ ID No: 26; SEQ ID No: 27; SEQ ID No: 28, SEQ ID No: 29, SEQ ID No: 50 and SEQ ID No: 51; and
   wherein the amino acid sequence of said polypeptide having aspartic endoprotease activity (EC 3.4.23.12) has at least 88% sequence identity to a sequence selected from the group consisting of: SEQ ID No.: 4; amino acid residues 30-451 of SEQ ID No: 6; amino acid residues 30-451 of SEQ ID No: 8; amino acid residues 30-451 of SEQ ID No: 10; amino acid residues 28-446 of SEQ ID No: 12; and amino acid residues 27-453 of SEQ ID No.: 45, and
   wherein said promoter directs endosperm-specific expression of said polynucleotide.

3. The genetically modified crop plant of claim 1, wherein the plant is a soybean plant; and
   wherein the nucleotide sequence of said heterologous promoter is SEQ ID No: 52; and
   wherein the amino acid sequence of said polypeptide having aspartic endoprotease activity (EC 3.4.23.12) has at least 88% sequence identity to SEQ ID No.: 4; or amino acid residues 32-453 of SEQ ID No.: 47.

4. The genetically modified crop plant of claim 1, wherein the plant is a cotton plant, and
   wherein the nucleotide sequence of said heterologous promoter is SEQ ID No: 54 or SEQ ID No: 55; and
   wherein the amino acid sequence of said polypeptide having aspartic endoprotease activity (EC 3.4.23.12) has at least 88% sequence identity to SEQ ID No.: 4; or amino acid residues 29-460 of SEQ ID No.:49.

5. The genetically modified crop plant of claim 1, where the amino acid sequence of said signal peptide is selected from the group consisting of: SEQ ID No: 14, 16, 18, 20, 22, 24 and amino acid residues 1-26 of SEQ ID No.: 45.

6. The genetically modified crop plant of claim 3, wherein the amino acid sequence of said signal peptide is amino acid residues 1-31 of SEQ ID No.:47.

7. The genetically modified crop plant of claim 4, wherein the amino acid sequence of said signal peptide is amino acid residues 1-28 of SEQ ID No.: 49.

8. The genetically modified crop plant of claim 1, wherein said crop plant is a species of *Triticum* or *Hordeum* or *Zea*.

9. A genetically modified grain or seed produced by the genetically modified crop plant of claim 1; wherein the grain or the seed comprises the construct.

10. A method for producing the genetically modified crop plant of claim 1; the method comprising:
    a. transforming one or more cells of a parent crop plant with the recombinant DNA construct, and
    b. selecting transformed cells of said plant, wherein the genome of said cells comprises a copy of said recombinant DNA construct; and
    c. regenerating a genetically modified crop plant from cells obtained in step (b);
    whereby the genetically modified crop plant exhibits enchanted resistance to a fungal disease compared to a control plant lacking the construct.

11. A method for manufacturing the genetically modified grain or seed according to claim 9 for production of a crop of genetically modified crop plants which exhibit increased resistance to a fungal disease caused by a species of *Fusarium* and/or *Aspergillus*, said method comprising:
    a. screening a population of plants for said recombinant DNA construct,
    b. selecting plants identified in step (a) as comprising said recombinant DNA construct and
    c. growing and collecting grain or seed from plants selected in step (b).

12. A method for producing a crop plant exhibiting increased resistance to a fungal disease caused by a species of *Fusarium* and/or *Aspergillus*, said method comprising:
    a. obtaining a sample of genomic DNA from a crop plant according to claim 1 or a part thereof;
    b. detecting in said sample the presence of said recombinant DNA construct;
    c. breeding a crop plant comprising said recombinant DNA construct with a second cereal plant of the same genus to obtain grains or seeds; and
    d. growing at least one crop plant from said grains or seeds,
    wherein said crop plant grown from said grains or seeds comprises said recombinant DNA construct.

13. The method of claim 12, where said recombinant DNA construct is detected by amplification of a region of the nucleic acid sequence of said construct, wherein said region has a 5' end within the promoter and a 3' end within the polynucleotide.

14. The method of claim 10, wherein said crop plant is a species of *Triticum* or *Hordeum* or *Zea*.

15. A composition comprising the genetically modified grain or seed of claim 9, wherein the composition is any one of:
    a. a milled grain or seed composition,
    b. animal fodder, and
    c. steam-pelleted animal fodder.

* * * * *

SEQUENCE LISTING

```
<160> NUMBER OF SEQ ID NOS: 55

<210> SEQ ID NO 1
<211> LENGTH: 1359
<212> TYPE: DNA
<213> ORGANISM: Hordeum vulgare
<220> FEATURE:
<221> NAME/KEY: CDS
<222> LOCATION: (1)..(1359)
<223> OTHER INFORMATION: HvNep-1 gene encoding HvNEP1 aspartic protease

<400> SEQUENCE: 1 atg gcc atg gcc atc atg aac acc ctc cag tgc atc ctc ttc ctc atg      48
Met Ala Met Ala Ile Met Asn Thr Leu Gln Cys Ile Leu Phe Leu Met
1               5                   10                  15 gcc ctc atc atg acc cac cag atc ccg cgc gcc acc gcc gat gcg gac      96
Ala Leu Ile Met Thr His Gln Ile Pro Arg Ala Thr Ala Asp Ala Asp
                20                  25                  30 acc cca aaa gtc gcc atg gct agc tcg ggc gcc ggt tcg agc ttc cgg     144
Thr Pro Lys Val Ala Met Ala Ser Ser Gly Ala Gly Ser Ser Phe Arg
            35                  40                  45 ctg gcg gcc cat cat gac cac gcg ctg agc cgg agc gac gac ggc ttc     192
Leu Ala Ala His His Asp His Ala Leu Ser Arg Ser Asp Asp Gly Phe
        50                  55                  60 ctc cat gtc cag agc cgg ctg gac aac ctt ctt cca tcg gag gcg aac     240
Leu His Val Gln Ser Arg Leu Asp Asn Leu Leu Pro Ser Glu Ala Asn
65                  70                  75                  80 gtc acc acc ctc cgc cca cca gtg gcc tcg ccg ctc gat atg gcc ttc     288
Val Thr Thr Leu Arg Pro Pro Val Ala Ser Pro Leu Asp Met Ala Phe
                85                  90                  95 agc gtg gtc gtt ggc ttg ggc tcg ggc aaa ggc cgg cat gac tac aac     336
Ser Val Val Val Gly Leu Gly Ser Gly Lys Gly Arg His Asp Tyr Asn
                100                 105                 110 ctc aag ctc gac gcc tct ggt agc ctg aca tgg gtg caa tgc aag ccc     384
Leu Lys Leu Asp Ala Ser Gly Ser Leu Thr Trp Val Gln Cys Lys Pro
            115                 120                 125 tgc aat ccc aag cag cca cag cgc ggc ccc ctg ttc gat ccc aag gcc     432
Cys Asn Pro Lys Gln Pro Gln Arg Gly Pro Leu Phe Asp Pro Lys Ala
        130                 135                 140 tcg tcc acc ttc cag caa gtg gcc ggc acg agc cag att tgc cac ccg     480
Ser Ser Thr Phe Gln Gln Val Ala Gly Thr Ser Gln Ile Cys His Pro
145                 150                 155                 160 ccg tac ccc atg gag ccc gcg ggg cag cag tgc gcc ttc cac ctg tcc     528
Pro Tyr Pro Met Glu Pro Ala Gly Gln Gln Cys Ala Phe His Leu Ser
                165                 170                 175 ggc atg ggc ggc atg tcg gtg cat ggc tac gtg gcc atg gag aac ctc     576
Gly Met Gly Gly Met Ser Val His Gly Tyr Val Ala Met Glu Asn Leu
                180                 185                 190 acc atg ggg cca gag gca atg aag gag ttc gtc ttc ggg tgc tcg cac     624
Thr Met Gly Pro Glu Ala Met Lys Glu Phe Val Phe Gly Cys Ser His
            195                 200                 205 tcg acg ggg cac ttc aac agc cac ggc acc ttc gcg ggc gtc gcc gcc     672
Ser Thr Gly His Phe Asn Ser His Gly Thr Phe Ala Gly Val Ala Ala
```

-continued

```
                  210                 215                 220
atg ggc aag atg ccc acc tcg ctc gtc atg cag gtg gcg gcg cgc ggg      720
Met Gly Lys Met Pro Thr Ser Leu Val Met Gln Val Ala Ala Arg Gly
225                 230                 235                 240 cag acg cgg ttc tcg tac tgc ctc ttc tcc ggc ggg gcg agc cgg cat      768
Gln Thr Arg Phe Ser Tyr Cys Leu Phe Ser Gly Gly Ala Ser Arg His
                245                 250                 255 ggg ttc ctc cgg ttc ggc gcc gac gtg ccg agc cgg tcg ggc ctc cgg      816
Gly Phe Leu Arg Phe Gly Ala Asp Val Pro Ser Arg Ser Gly Leu Arg
            260                 265                 270 acg acc aag atc ctc ccg gcg ctg gac gcg cac gag tcg cag tac tac      864
Thr Thr Lys Ile Leu Pro Ala Leu Asp Ala His Glu Ser Gln Tyr Tyr
        275                 280                 285 gtg agc ctc gtg ggc atc agc ctg gac gcc aag agg ctg acg ggg gtc      912
Val Ser Leu Val Gly Ile Ser Leu Asp Ala Lys Arg Leu Thr Gly Val
    290                 295                 300 agg ccg gag atg ttc gcc cga cag cgc ggt ggg gag ggc ggg tgc gtg      960
Arg Pro Glu Met Phe Ala Arg Gln Arg Gly Gly Glu Gly Gly Cys Val
305                 310                 315                 320 gtc gac ccc ggc acg ccg ctg acg gtg ctg gtc cgg gag gcg tac cgc     1008
Val Asp Pro Gly Thr Pro Leu Thr Val Leu Val Arg Glu Ala Tyr Arg
                325                 330                 335 gtc gtg gag gac gcc gtc tgg agt gac cta cga cgg aac aag gcc gag     1056
Val Val Glu Asp Ala Val Trp Ser Asp Leu Arg Arg Asn Lys Ala Glu
            340                 345                 350 cgc gtg cag cgc gaa ggc tac ggg ctg tgc gtg cgc aaa acc gca gag     1104
Arg Val Gln Arg Glu Gly Tyr Gly Leu Cys Val Arg Lys Thr Ala Glu
        355                 360                 365 atc aag cgg cat ctg cag tcg ctg tcc ttg cac ttc gcg gag gag acg     1152
Ile Lys Arg His Leu Gln Ser Leu Ser Leu His Phe Ala Glu Glu Thr
    370                 375                 380 gcg agg ctg gtc gtg aag ccg gag cag ctg ttc gtg gcg gtg gag agc     1200
Ala Arg Leu Val Val Lys Pro Glu Gln Leu Phe Val Ala Val Glu Ser
385                 390                 395                 400 agg ctc cat ggg gcc gcc ctg tgc ctt gcc atg cgt ccg ggc gag cgg     1248
Arg Leu His Gly Ala Ala Leu Cys Leu Ala Met Arg Pro Gly Glu Arg
                405                 410                 415 acg gtc atc ggc gcg ctg cag cag gtg gac acg agg ttc gtg tac gac     1296
Thr Val Ile Gly Ala Leu Gln Gln Val Asp Thr Arg Phe Val Tyr Asp
            420                 425                 430 ctc aaa gac gcc aaa ctg tcc ttt gcg tcc gag ccg tgc tct cag gac     1344
Leu Lys Asp Ala Lys Leu Ser Phe Ala Ser Glu Pro Cys Ser Gln Asp
        435                 440                 445 acc gcc ggt gtg gat                                                  1359
Thr Ala Gly Val Asp
    450
```

<210> SEQ ID NO 2
<211> LENGTH: 453
<212> TYPE: PRT
<213> ORGANISM: Hordeum vulgare

<400> SEQUENCE: 2

```
Met Ala Met Ala Ile Met Asn Thr Leu Gln Cys Ile Leu Phe Leu Met
1               5                   10                  15

Ala Leu Ile Met Thr His Gln Ile Pro Arg Ala Thr Ala Asp Ala Asp
                20                  25                  30

Thr Pro Lys Val Ala Met Ala Ser Ser Gly Ala Gly Ser Ser Phe Arg
            35                  40                  45
```

```
Leu Ala Ala His His Asp His Ala Leu Ser Arg Ser Asp Asp Gly Phe
 50                  55                  60

Leu His Val Gln Ser Arg Leu Asp Asn Leu Leu Pro Ser Glu Ala Asn
 65                  70                  75                  80

Val Thr Thr Leu Arg Pro Pro Val Ala Ser Pro Leu Asp Met Ala Phe
                     85                  90                  95

Ser Val Val Val Gly Leu Gly Ser Gly Lys Gly Arg His Asp Tyr Asn
                 100                 105                 110

Leu Lys Leu Asp Ala Ser Gly Ser Leu Thr Trp Val Gln Cys Lys Pro
             115                 120                 125

Cys Asn Pro Lys Gln Pro Gln Arg Gly Pro Leu Phe Asp Pro Lys Ala
130                 135                 140

Ser Ser Thr Phe Gln Gln Val Ala Gly Thr Ser Gln Ile Cys His Pro
145                 150                 155                 160

Pro Tyr Pro Met Glu Pro Ala Gly Gln Gln Cys Ala Phe His Leu Ser
                 165                 170                 175

Gly Met Gly Gly Met Ser Val His Gly Tyr Val Ala Met Glu Asn Leu
             180                 185                 190

Thr Met Gly Pro Glu Ala Met Lys Glu Phe Val Phe Gly Cys Ser His
             195                 200                 205

Ser Thr Gly His Phe Asn Ser His Gly Thr Phe Ala Gly Val Ala Ala
210                 215                 220

Met Gly Lys Met Pro Thr Ser Leu Val Met Gln Val Ala Ala Arg Gly
225                 230                 235                 240

Gln Thr Arg Phe Ser Tyr Cys Leu Phe Ser Gly Gly Ala Ser Arg His
                 245                 250                 255

Gly Phe Leu Arg Phe Gly Ala Asp Val Pro Ser Arg Ser Gly Leu Arg
             260                 265                 270

Thr Thr Lys Ile Leu Pro Ala Leu Asp Ala His Glu Ser Gln Tyr Tyr
         275                 280                 285

Val Ser Leu Val Gly Ile Ser Leu Asp Ala Lys Arg Leu Thr Gly Val
     290                 295                 300

Arg Pro Glu Met Phe Ala Arg Gln Arg Gly Gly Glu Gly Gly Cys Val
305                 310                 315                 320

Val Asp Pro Gly Thr Pro Leu Thr Val Leu Arg Glu Ala Tyr Arg
                 325                 330                 335

Val Val Glu Asp Ala Val Trp Ser Asp Leu Arg Arg Asn Lys Ala Glu
             340                 345                 350

Arg Val Gln Arg Glu Gly Tyr Gly Leu Cys Val Arg Lys Thr Ala Glu
             355                 360                 365

Ile Lys Arg His Leu Gln Ser Leu Ser Leu His Phe Ala Glu Glu Thr
     370                 375                 380

Ala Arg Leu Val Val Lys Pro Glu Gln Leu Phe Val Ala Val Glu Ser
385                 390                 395                 400

Arg Leu His Gly Ala Ala Leu Cys Leu Ala Met Arg Pro Gly Glu Arg
                 405                 410                 415

Thr Val Ile Gly Ala Leu Gln Gln Val Asp Thr Arg Phe Val Tyr Asp
             420                 425                 430

Leu Lys Asp Ala Lys Leu Ser Phe Ala Ser Glu Pro Cys Ser Gln Asp
             435                 440                 445

Thr Ala Gly Val Asp
450
```

```
<210> SEQ ID NO 3
<211> LENGTH: 1272
<212> TYPE: DNA
<213> ORGANISM: Hordeum vulgare
<220> FEATURE:
<221> NAME/KEY: CDS
<222> LOCATION: (1)..(1272)
<223> OTHER INFORMATION: Nucleotide sequence encoding HvNEP (truncated
      to delete signal peptide)

<400> SEQUENCE: 3
```

| | | | | | | | | | | | | | | | | |
|---|---|---|---|---|---|---|---|---|---|---|---|---|---|---|---|---|
| gat | gcg | gac | acc | cca | aaa | gtc | gcc | atg | gct | agc | tcg | ggc | gcc | ggt | tcg | 48 |
| Asp | Ala | Asp | Thr | Pro | Lys | Val | Ala | Met | Ala | Ser | Ser | Gly | Ala | Gly | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agc | ttc | cgg | ctg | gcg | gcc | cat | cat | gac | cac | gcg | ctg | agc | cgg | agc | gac | 96 |
| Ser | Phe | Arg | Leu | Ala | Ala | His | His | Asp | His | Ala | Leu | Ser | Arg | Ser | Asp | |
| | | | 20 | | | | | 25 | | | | | 30 | | | |

| | | | | | | | | | | | | | | | | |
|---|---|---|---|---|---|---|---|---|---|---|---|---|---|---|---|---|
| gac | ggc | ttc | ctc | cat | gtc | cag | agc | cgg | ctg | gac | aac | ctt | ctt | cca | tcg | 144 |
| Asp | Gly | Phe | Leu | His | Val | Gln | Ser | Arg | Leu | Asp | Asn | Leu | Leu | Pro | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| gag | gcg | aac | gtc | acc | acc | ctc | cgc | cca | cca | gtg | gcc | tcg | ccg | ctc | gat | 192 |
| Glu | Ala | Asn | Val | Thr | Thr | Leu | Arg | Pro | Pro | Val | Ala | Ser | Pro | Leu | Asp | |
| | 50 | | | | | 55 | | | | | 60 | | | | | |

| | | | | | | | | | | | | | | | | |
|---|---|---|---|---|---|---|---|---|---|---|---|---|---|---|---|---|
| atg | gcc | ttc | agc | gtg | gtc | gtt | ggc | ttg | ggc | tcg | ggc | aaa | ggc | cgg | cat | 240 |
| Met | Ala | Phe | Ser | Val | Val | Val | Gly | Leu | Gly | Ser | Gly | Lys | Gly | Arg | His | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gac | tac | aac | ctc | aag | ctc | gac | gcc | tct | ggt | agc | ctg | aca | tgg | gtg | caa | 288 |
| Asp | Tyr | Asn | Leu | Lys | Leu | Asp | Ala | Ser | Gly | Ser | Leu | Thr | Trp | Val | Gln | |
| | | | | 85 | | | | | 90 | | | | | 95 | | |

| | | | | | | | | | | | | | | | | |
|---|---|---|---|---|---|---|---|---|---|---|---|---|---|---|---|---|
| tgc | aag | ccc | tgc | aat | ccc | aag | cag | cca | cag | cgc | ggc | ccc | ctg | ttc | gat | 336 |
| Cys | Lys | Pro | Cys | Asn | Pro | Lys | Gln | Pro | Gln | Arg | Gly | Pro | Leu | Phe | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| ccc | aag | gcc | tcg | tcc | acc | ttc | cag | caa | gtg | gcc | ggc | acg | agc | cag | att | 384 |
| Pro | Lys | Ala | Ser | Ser | Thr | Phe | Gln | Gln | Val | Ala | Gly | Thr | Ser | Gln | Ile | |
| | | | 115 | | | | | 120 | | | | | 125 | | | |

| | | | | | | | | | | | | | | | | |
|---|---|---|---|---|---|---|---|---|---|---|---|---|---|---|---|---|
| tgc | cac | ccg | ccg | tac | ccc | atg | gag | ccc | gcg | ggg | cag | cag | tgc | gcc | ttc | 432 |
| Cys | His | Pro | Pro | Tyr | Pro | Met | Glu | Pro | Ala | Gly | Gln | Gln | Cys | Ala | Phe | |
| | 130 | | | | | 135 | | | | | 140 | | | | | |

| | | | | | | | | | | | | | | | | |
|---|---|---|---|---|---|---|---|---|---|---|---|---|---|---|---|---|
| cac | ctg | tcc | ggc | atg | ggc | ggc | atg | tcg | gtg | cat | ggc | tac | gtg | gcc | atg | 480 |
| His | Leu | Ser | Gly | Met | Gly | Gly | Met | Ser | Val | His | Gly | Tyr | Val | Ala | Met | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gag | aac | ctc | acc | atg | ggg | cca | gag | gca | atg | aag | gag | ttc | gtc | ttc | ggg | 528 |
| Glu | Asn | Leu | Thr | Met | Gly | Pro | Glu | Ala | Met | Lys | Glu | Phe | Val | Phe | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| tgc | tcg | cac | tcg | acg | ggg | cac | ttc | aac | agc | cac | ggc | acc | ttc | gcg | ggc | 576 |
| Cys | Ser | His | Ser | Thr | Gly | His | Phe | Asn | Ser | His | Gly | Thr | Phe | Ala | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| gtc | gcc | gcc | atg | ggc | aag | atg | ccc | acc | tcg | ctc | gtc | atg | cag | gtg | gcg | 624 |
| Val | Ala | Ala | Met | Gly | Lys | Met | Pro | Thr | Ser | Leu | Val | Met | Gln | Val | Ala | |
| | | | 195 | | | | | 200 | | | | | 205 | | | |

| | | | | | | | | | | | | | | | | |
|---|---|---|---|---|---|---|---|---|---|---|---|---|---|---|---|---|
| gcg | cgc | ggg | cag | acg | cgg | ttc | tcg | tac | tgc | ctc | ttc | tcc | ggc | ggg | gcg | 672 |
| Ala | Arg | Gly | Gln | Thr | Arg | Phe | Ser | Tyr | Cys | Leu | Phe | Ser | Gly | Gly | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| agc | cgg | cat | ggg | ttc | ctc | cgg | ttc | ggc | gcc | gac | gtg | ccg | agc | cgg | tcg | 720 |
| Ser | Arg | His | Gly | Phe | Leu | Arg | Phe | Gly | Ala | Asp | Val | Pro | Ser | Arg | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ggc | ctc | cgg | acg | acc | aag | atc | ctc | ccg | gcg | ctg | gac | gcg | cac | gag | tcg | 768 |
| Gly | Leu | Arg | Thr | Thr | Lys | Ile | Leu | Pro | Ala | Leu | Asp | Ala | His | Glu | Ser | |
| | | | | 245 | | | | | 250 | | | | | 255 | | |

| | | | | | | | | | | | | | | | | |
|---|---|---|---|---|---|---|---|---|---|---|---|---|---|---|---|---|
| cag | tac | tac | gtg | agc | ctc | gtg | ggc | atc | agc | ctg | gac | gcc | aag | agg | ctg | 816 |
| Gln | Tyr | Tyr | Val | Ser | Leu | Val | Gly | Ile | Ser | Leu | Asp | Ala | Lys | Arg | Leu | |
| | | | 260 | | | | | 265 | | | | | 270 | | | |

```
acg ggg gtc agg ccg gag atg ttc gcc cga cag cgc ggt ggg gag ggc       864
Thr Gly Val Arg Pro Glu Met Phe Ala Arg Gln Arg Gly Gly Glu Gly
        275                 280                 285 ggg tgc gtg gtc gac ccc ggc acg ccg ctg acg gtg ctg gtc cgg gag       912
Gly Cys Val Val Asp Pro Gly Thr Pro Leu Thr Val Leu Val Arg Glu
    290                 295                 300 gcg tac cgc gtc gtg gag gac gcc gtc tgg agt gac cta cga cgg aac       960
Ala Tyr Arg Val Val Glu Asp Ala Val Trp Ser Asp Leu Arg Arg Asn
305                 310                 315                 320 aag gcc gag cgc gtg cag cgc gaa ggc tac ggg ctg tgc gtg cgc aaa      1008
Lys Ala Glu Arg Val Gln Arg Glu Gly Tyr Gly Leu Cys Val Arg Lys
                325                 330                 335 acc gca gag atc aag cgg cat ctg cag tcg ctg tcc ttg cac ttc gcg      1056
Thr Ala Glu Ile Lys Arg His Leu Gln Ser Leu Ser Leu His Phe Ala
            340                 345                 350 gag gag acg gcg agg ctg gtc gtg aag ccg gag cag ctg ttc gtg gcg      1104
Glu Glu Thr Ala Arg Leu Val Val Lys Pro Glu Gln Leu Phe Val Ala
        355                 360                 365 gtg gag agc agg ctc cat ggg gcc gcc ctg tgc ctt gcc atg cgt ccg      1152
Val Glu Ser Arg Leu His Gly Ala Ala Leu Cys Leu Ala Met Arg Pro
    370                 375                 380 ggc gag cgg acg gtc atc ggc gcg ctg cag cag gtg gac acg agg ttc      1200
Gly Glu Arg Thr Val Ile Gly Ala Leu Gln Gln Val Asp Thr Arg Phe
385                 390                 395                 400 gtg tac gac ctc aaa gac gcc aaa ctg tcc ttt gcg tcc gag ccg tgc      1248
Val Tyr Asp Leu Lys Asp Ala Lys Leu Ser Phe Ala Ser Glu Pro Cys
                405                 410                 415 tct cag gac acc gcc ggt gtg gat                                      1272
Ser Gln Asp Thr Ala Gly Val Asp
            420
```

<210> SEQ ID NO 4
<211> LENGTH: 424
<212> TYPE: PRT
<213> ORGANISM: Hordeum vulgare

<400> SEQUENCE: 4

```
Asp Ala Asp Thr Pro Lys Val Ala Met Ala Ser Ser Gly Ala Gly Ser
1               5                   10                  15

Ser Phe Arg Leu Ala Ala His His Asp His Ala Leu Ser Arg Ser Asp
            20                  25                  30

Asp Gly Phe Leu His Val Gln Ser Arg Leu Asp Asn Leu Leu Pro Ser
        35                  40                  45

Glu Ala Asn Val Thr Thr Leu Arg Pro Pro Val Ala Ser Pro Leu Asp
    50                  55                  60

Met Ala Phe Ser Val Val Gly Leu Gly Ser Gly Lys Gly Arg His
65                  70                  75                  80

Asp Tyr Asn Leu Lys Leu Asp Ala Ser Gly Ser Leu Thr Trp Val Gln
                85                  90                  95

Cys Lys Pro Cys Asn Pro Lys Gln Pro Gln Arg Gly Pro Leu Phe Asp
            100                 105                 110

Pro Lys Ala Ser Ser Thr Phe Gln Gln Val Ala Gly Thr Ser Gln Ile
        115                 120                 125

Cys His Pro Pro Tyr Pro Met Glu Pro Ala Gly Gln Gln Cys Ala Phe
    130                 135                 140

His Leu Ser Gly Met Gly Gly Met Ser Val His Gly Tyr Val Ala Met
145                 150                 155                 160
```

```
Glu Asn Leu Thr Met Gly Pro Glu Ala Met Lys Glu Phe Val Phe Gly
                165                 170                 175

Cys Ser His Ser Thr Gly His Phe Asn Ser His Gly Thr Phe Ala Gly
            180                 185                 190

Val Ala Ala Met Gly Lys Met Pro Thr Ser Leu Val Met Gln Val Ala
        195                 200                 205

Ala Arg Gly Gln Thr Arg Phe Ser Tyr Cys Leu Phe Ser Gly Gly Ala
    210                 215                 220

Ser Arg His Gly Phe Leu Arg Phe Gly Ala Asp Val Pro Ser Arg Ser
225                 230                 235                 240

Gly Leu Arg Thr Thr Lys Ile Leu Pro Ala Leu Asp Ala His Glu Ser
                245                 250                 255

Gln Tyr Tyr Val Ser Leu Val Gly Ile Ser Leu Asp Ala Lys Arg Leu
            260                 265                 270

Thr Gly Val Arg Pro Glu Met Phe Ala Arg Gln Arg Gly Gly Glu Gly
        275                 280                 285

Gly Cys Val Val Asp Pro Gly Thr Pro Leu Thr Val Leu Val Arg Glu
    290                 295                 300

Ala Tyr Arg Val Glu Asp Ala Val Trp Ser Asp Leu Arg Arg Asn
305                 310                 315                 320

Lys Ala Glu Arg Val Gln Arg Glu Gly Tyr Gly Leu Cys Val Arg Lys
                325                 330                 335

Thr Ala Glu Ile Lys Arg His Leu Gln Ser Leu Ser Leu His Phe Ala
            340                 345                 350

Glu Glu Thr Ala Arg Leu Val Val Lys Pro Glu Gln Leu Phe Val Ala
        355                 360                 365

Val Glu Ser Arg Leu His Gly Ala Ala Leu Cys Leu Ala Met Arg Pro
    370                 375                 380

Gly Glu Arg Thr Val Ile Gly Ala Leu Gln Gln Val Asp Thr Arg Phe
385                 390                 395                 400

Val Tyr Asp Leu Lys Asp Ala Lys Leu Ser Phe Ala Ser Glu Pro Cys
                405                 410                 415

Ser Gln Asp Thr Ala Gly Val Asp
            420

<210> SEQ ID NO 5
<211> LENGTH: 1356
<212> TYPE: DNA
<213> ORGANISM: Aegilops tauschii
<220> FEATURE:
<221> NAME/KEY: CDS
<222> LOCATION: (1)..(1356)
<223> OTHER INFORMATION: Nep-1 gene encoding NEP-1 aspartic endoprotease

<400> SEQUENCE: 5 atg gcc atg gcg atc aag agc act ctc caa tgc gta gtg ttc ctg atg      48
Met Ala Met Ala Ile Lys Ser Thr Leu Gln Cys Val Val Phe Leu Met
1               5                   10                  15 gcg ctc atc acg acc cac ctg ata ccg cct gcc gat gct gat gcg ggc      96
Ala Leu Ile Thr Thr His Leu Ile Pro Pro Ala Asp Ala Asp Ala Gly
            20                  25                  30 agc cca aaa gtt gcc atg gct agc tcg ggc gct ggt tca agc ttc cgg     144
Ser Pro Lys Val Ala Met Ala Ser Ser Gly Ala Gly Ser Ser Phe Arg
        35                  40                  45 ctg gta gcc cac cat gac tat gcg ctg cgc gac gac ggc ttc ctc cac     192
Leu Val Ala His His Asp Tyr Ala Leu Arg Asp Asp Gly Phe Leu His
    50                  55                  60
```

| | | |
|---|---|---|
| gtc cag agc cgg ctg gac gac ctt ctt cca tcg gag gcg aac gtc acc<br>Val Gln Ser Arg Leu Asp Asp Leu Leu Pro Ser Glu Ala Asn Val Thr<br>65                             70                     75                      80 | 240 |
| acc ctc cgc cca cca gtg gcc tcg ccg atc gat atg gcc ttc agc gtg<br>Thr Leu Arg Pro Pro Val Ala Ser Pro Ile Asp Met Ala Phe Ser Val<br>85                       90                   95 | 288 |
| gtc gtt ggc ttg ggc tcg ggc aaa ggc cgg cac gac tac aac ctc aag<br>Val Val Gly Leu Gly Ser Gly Lys Gly Arg His Asp Tyr Asn Leu Lys<br>100                   105                 110 | 336 |
| ctc gac gcc tcg ggt agc ctg atg tgg ctg cag tgc aag ccc tgc aat<br>Leu Asp Ala Ser Gly Ser Leu Met Trp Leu Gln Cys Lys Pro Cys Asn<br>115               120                 125 | 384 |
| ccg aag cag cca cag cgc ggc ccc ctg ttc gac ccc aag gcc tcg tcc<br>Pro Lys Gln Pro Gln Arg Gly Pro Leu Phe Asp Pro Lys Ala Ser Ser<br>130               135                 140 | 432 |
| acc ttc cag cag gtc gcc ggc acg agc cag atc tgc cac ccg ccg tac<br>Thr Phe Gln Gln Val Ala Gly Thr Ser Gln Ile Cys His Pro Pro Tyr<br>145               150                 155                 160 | 480 |
| ccc atg gag ccc gcg ggg cag cag tgc gcc ttc cac ctg tcc ggc gag<br>Pro Met Glu Pro Ala Gly Gln Gln Cys Ala Phe His Leu Ser Gly Glu<br>               165                 170                 175 | 528 |
| cac ggc atg tcg gtg cac ggc ttc gtg gcc ttg gag aac ctc acc atg<br>His Gly Met Ser Val His Gly Phe Val Ala Leu Glu Asn Leu Thr Met<br>180               185                 190 | 576 |
| ggg cca gag tcc atg aag gag ttc gtc ttc ggg tgc gcg cac tcg gcc<br>Gly Pro Glu Ser Met Lys Glu Phe Val Phe Gly Cys Ala His Ser Ala<br>195               200                 205 | 624 |
| gag cac ttc aac agc cag cgc acc ttc gcg ggc gtc gcc gcc atg ggt<br>Glu His Phe Asn Ser Gln Arg Thr Phe Ala Gly Val Ala Ala Met Gly<br>210               215                 220 | 672 |
| aag atg ccc acc tcc ctc gtc atg cag gtg gcg gcg cgt ggg cag acg<br>Lys Met Pro Thr Ser Leu Val Met Gln Val Ala Ala Arg Gly Gln Thr<br>225               230                 235                 240 | 720 |
| cgg ttc tcg tac tgc ctc ttc tcc ggc ggg gcg agc cgg cat ggc ttc<br>Arg Phe Ser Tyr Cys Leu Phe Ser Gly Gly Ala Ser Arg His Gly Phe<br>               245                 250                 255 | 768 |
| ctc cgg ttt ggc gcc gac gtg ccg agc cgg ccg ggc ctc cga acg acc<br>Leu Arg Phe Gly Ala Asp Val Pro Ser Arg Pro Gly Leu Arg Thr Thr<br>260               265                 270 | 816 |
| aag atc ctc ccg gcg ctg gac gcg cac gag tcg cag tac tac gtg agc<br>Lys Ile Leu Pro Ala Leu Asp Ala His Glu Ser Gln Tyr Tyr Val Ser<br>275               280                 285 | 864 |
| ctc gtg ggc atc agc ctg gac gct aag agg ctc acg cgg atc agg ccg<br>Leu Val Gly Ile Ser Leu Asp Ala Lys Arg Leu Thr Arg Ile Arg Pro<br>290               295                 300 | 912 |
| gag atg ttc gcc cgg cgg cgc ggc ggg cag ggc ggg tgc gtg atc gac<br>Glu Met Phe Ala Arg Arg Arg Gly Gly Gln Gly Gly Cys Val Ile Asp<br>305               310                 315                 320 | 960 |
| ccc ggc acg ccg ctg acg gtg ctg gcc cgg gag gcg tat cgc gtc gtg<br>Pro Gly Thr Pro Leu Thr Val Leu Ala Arg Glu Ala Tyr Arg Val Val<br>               325                 330                 335 | 1008 |
| gag gac gcc gtc tgg agt gac ctg cgg cgg aat agg gcc gag cgc atc<br>Glu Asp Ala Val Trp Ser Asp Leu Arg Arg Asn Arg Ala Glu Arg Ile<br>340               345                 350 | 1056 |
| cag cgg cag ggc tac ggg ttg tgc gtc cgc aag acc gcg gag atc aag<br>Gln Arg Gln Gly Tyr Gly Leu Cys Val Arg Lys Thr Ala Glu Ile Lys<br>355               360                 365 | 1104 |
| cgg cac ctc cag tcg ctg tcc ttc cac ttc gcg gag gag acg gcg agg<br>Arg His Leu Gln Ser Leu Ser Phe His Phe Ala Glu Glu Thr Ala Arg<br>370               375                 380 | 1152 |

```
ctg gtc gtc aag ccg gag gag ctg ttc acg gcg gtg gag ggc agg ctc    1200
Leu Val Val Lys Pro Glu Glu Leu Phe Thr Ala Val Glu Gly Arg Leu
385                 390                 395                 400 cac ggt ccc gcc ctg tgc ttt gcc atg agc ccg ggc gag cgg acg gtc    1248
His Gly Pro Ala Leu Cys Phe Ala Met Ser Pro Gly Glu Arg Thr Val
                405                 410                 415 atc ggc gcg ctg cag cag gtg gac aca agg ttc gtg tac gac cta aaa    1296
Ile Gly Ala Leu Gln Gln Val Asp Thr Arg Phe Val Tyr Asp Leu Lys
            420                 425                 430 gac gct aaa ctg tcc ttt gcg tcg gag ccg tgt tct cag gac acc gcc    1344
Asp Ala Lys Leu Ser Phe Ala Ser Glu Pro Cys Ser Gln Asp Thr Ala
        435                 440                 445 ggt gtg gat tga                                                    1356
Gly Val Asp
    450
```

<210> SEQ ID NO 6
<211> LENGTH: 451
<212> TYPE: PRT
<213> ORGANISM: Aegilops tauschii

<400> SEQUENCE: 6

```
Met Ala Met Ala Ile Lys Ser Thr Leu Gln Cys Val Val Phe Leu Met
1               5                   10                  15

Ala Leu Ile Thr Thr His Leu Ile Pro Pro Ala Asp Ala Asp Ala Gly
            20                  25                  30

Ser Pro Lys Val Ala Met Ala Ser Ser Gly Ala Gly Ser Ser Phe Arg
        35                  40                  45

Leu Val Ala His His Asp Tyr Ala Leu Arg Asp Asp Gly Phe Leu His
    50                  55                  60

Val Gln Ser Arg Leu Asp Asp Leu Leu Pro Ser Glu Ala Asn Val Thr
65                  70                  75                  80

Thr Leu Arg Pro Pro Val Ala Ser Pro Ile Asp Met Ala Phe Ser Val
                85                  90                  95

Val Val Gly Leu Gly Ser Gly Lys Gly Arg His Asp Tyr Asn Leu Lys
            100                 105                 110

Leu Asp Ala Ser Gly Ser Leu Met Trp Leu Gln Cys Lys Pro Cys Asn
        115                 120                 125

Pro Lys Gln Pro Gln Arg Gly Pro Leu Phe Asp Pro Lys Ala Ser Ser
    130                 135                 140

Thr Phe Gln Gln Val Ala Gly Thr Ser Gln Ile Cys His Pro Pro Tyr
145                 150                 155                 160

Pro Met Glu Pro Ala Gly Gln Gln Cys Ala Phe His Leu Ser Gly Glu
                165                 170                 175

His Gly Met Ser Val His Gly Phe Val Ala Leu Glu Asn Leu Thr Met
            180                 185                 190

Gly Pro Glu Ser Met Lys Glu Phe Val Phe Gly Cys Ala His Ser Ala
        195                 200                 205

Glu His Phe Asn Ser Gln Arg Thr Phe Ala Gly Val Ala Ala Met Gly
    210                 215                 220

Lys Met Pro Thr Ser Leu Val Met Gln Val Ala Ala Arg Gly Gln Thr
225                 230                 235                 240

Arg Phe Ser Tyr Cys Leu Phe Ser Gly Gly Ala Ser Arg His Gly Phe
                245                 250                 255

Leu Arg Phe Gly Ala Asp Val Pro Ser Arg Pro Gly Leu Arg Thr Thr
            260                 265                 270
```

-continued

```
Lys Ile Leu Pro Ala Leu Asp Ala His Glu Ser Gln Tyr Tyr Val Ser
        275                 280                 285

Leu Val Gly Ile Ser Leu Asp Ala Lys Arg Leu Thr Arg Ile Arg Pro
    290                 295                 300

Glu Met Phe Ala Arg Arg Arg Gly Gly Gln Gly Gly Cys Val Ile Asp
305                 310                 315                 320

Pro Gly Thr Pro Leu Thr Val Leu Ala Arg Glu Ala Tyr Arg Val Val
                325                 330                 335

Glu Asp Ala Val Trp Ser Asp Leu Arg Arg Asn Arg Ala Glu Arg Ile
            340                 345                 350

Gln Arg Gln Gly Tyr Gly Leu Cys Val Arg Lys Thr Ala Glu Ile Lys
        355                 360                 365

Arg His Leu Gln Ser Leu Ser Phe His Phe Ala Glu Glu Thr Ala Arg
    370                 375                 380

Leu Val Val Lys Pro Glu Glu Leu Phe Thr Ala Val Glu Gly Arg Leu
385                 390                 395                 400

His Gly Pro Ala Leu Cys Phe Ala Met Ser Pro Gly Glu Arg Thr Val
                405                 410                 415

Ile Gly Ala Leu Gln Gln Val Asp Thr Arg Phe Val Tyr Asp Leu Lys
            420                 425                 430

Asp Ala Lys Leu Ser Phe Ala Ser Glu Pro Cys Ser Gln Asp Thr Ala
        435                 440                 445

Gly Val Asp
    450

<210> SEQ ID NO 7
<211> LENGTH: 1353
<212> TYPE: DNA
<213> ORGANISM: Triticum aestivum
<220> FEATURE:
<221> NAME/KEY: CDS
<222> LOCATION: (1)..(1353)
<223> OTHER INFORMATION: TaNep-1 gene encoding TaNEP1 aspartic protease

<400> SEQUENCE: 7 atg gcc atg gcc atc aag tcc acc ctc caa tgc gtg gtg ttc ctc atg      48
Met Ala Met Ala Ile Lys Ser Thr Leu Gln Cys Val Val Phe Leu Met
1               5                   10                  15 gcc ctc atc acc acc cac ctc atc cca cca gcc gac gcc gac gcc ggc      96
Ala Leu Ile Thr Thr His Leu Ile Pro Pro Ala Asp Ala Asp Ala Gly
                20                  25                  30 tcc cca aag gtg gcc atg gcc tcc tcc ggc gcc ggc tcc tcc ttc agg     144
Ser Pro Lys Val Ala Met Ala Ser Ser Gly Ala Gly Ser Ser Phe Arg
            35                  40                  45 ctc gtg gcc cac cac gac tac gcc ctc agg gac gac ggc ttc ctc cac     192
Leu Val Ala His His Asp Tyr Ala Leu Arg Asp Asp Gly Phe Leu His
        50                  55                  60 gtg caa tcc agg ctc gac gac ctc ctc cca tcc gag gcc aac gtg acc     240
Val Gln Ser Arg Leu Asp Asp Leu Leu Pro Ser Glu Ala Asn Val Thr
65                  70                  75                  80 acc ctc agg cca cca gtg gcc tcc cca atc gac atg gcc ttc tcc gtg     288
Thr Leu Arg Pro Pro Val Ala Ser Pro Ile Asp Met Ala Phe Ser Val
                85                  90                  95 gtg gtg ggc ctc ggc tcc ggc aag ggc agg cac gac tac aac ctc aag     336
Val Val Gly Leu Gly Ser Gly Lys Gly Arg His Asp Tyr Asn Leu Lys
                100                 105                 110 ctc gac gcc tcc ggc tcc ctc atg tgg ctc caa tgc aag cca tgc aac     384
Leu Asp Ala Ser Gly Ser Leu Met Trp Leu Gln Cys Lys Pro Cys Asn
```

-continued

|     |     |     | 115 |     |     |     |     | 120 |     |     |     |     | 125 |     |     |      |
|-----|-----|-----|-----|-----|-----|-----|-----|-----|-----|-----|-----|-----|-----|-----|-----|------|

```
cca aag caa cca caa agg ggc cca ctc ttc gac cca aag gcc tcc tcc   432
Pro Lys Gln Pro Gln Arg Gly Pro Leu Phe Asp Pro Lys Ala Ser Ser
    130                 135                 140 acc ttc caa caa gtg gcc ggc acc tcc caa atc tgc cac cca cca tac   480
Thr Phe Gln Gln Val Ala Gly Thr Ser Gln Ile Cys His Pro Pro Tyr
145                 150                 155                 160 cca atg gag cca gcc ggc caa caa tgc gcc ttc cac ctc tcc ggc gag   528
Pro Met Glu Pro Ala Gly Gln Gln Cys Ala Phe His Leu Ser Gly Glu
                    165                 170                 175 cac ggc atg tcc gtg cac ggc ttc gtg gcc ctc gag aac ctc acc atg   576
His Gly Met Ser Val His Gly Phe Val Ala Leu Glu Asn Leu Thr Met
                180                 185                 190 ggc cca gag tcc atg aag gag ttc gtg ttc ggc tgc gcc cac tcc gcc   624
Gly Pro Glu Ser Met Lys Glu Phe Val Phe Gly Cys Ala His Ser Ala
            195                 200                 205 gag cac ttc aac tcc caa agg acc ttc gcc ggc gtg gcc gcc atg ggc   672
Glu His Phe Asn Ser Gln Arg Thr Phe Ala Gly Val Ala Ala Met Gly
        210                 215                 220 aag atg cca acc tcc ctc gtg atg caa gtg gcc gcc agg ggc caa acc   720
Lys Met Pro Thr Ser Leu Val Met Gln Val Ala Ala Arg Gly Gln Thr
225                 230                 235                 240 agg ttc tcc tac tgc ctc ttc tcc ggc ggc gcc tcc agg cac ggc ttc   768
Arg Phe Ser Tyr Cys Leu Phe Ser Gly Gly Ala Ser Arg His Gly Phe
                    245                 250                 255 ctc agg ttc ggc gcc gac gtg cca tcc agg cca ggc ctc agg acc acc   816
Leu Arg Phe Gly Ala Asp Val Pro Ser Arg Pro Gly Leu Arg Thr Thr
                260                 265                 270 aag atc ctc cca gcc ctc gac gcc cac gag tcc caa tac tac gtg tcc   864
Lys Ile Leu Pro Ala Leu Asp Ala His Glu Ser Gln Tyr Tyr Val Ser
            275                 280                 285 ctc gtg ggc atc tcc ctc gac gcc aag agg ctc acc agg atc agg cca   912
Leu Val Gly Ile Ser Leu Asp Ala Lys Arg Leu Thr Arg Ile Arg Pro
        290                 295                 300 gag atg ttc gcc agg agg agg ggc ggc caa ggc ggc tgc gtg atc gac   960
Glu Met Phe Ala Arg Arg Arg Gly Gly Gln Gly Gly Cys Val Ile Asp
305                 310                 315                 320 cca ggc acc cca ctc acc gtg ctc gcc agg gag gcc tac agg gtg gtg  1008
Pro Gly Thr Pro Leu Thr Val Leu Ala Arg Glu Ala Tyr Arg Val Val
                    325                 330                 335 gag gac gcc gtg tgg tcc gac ctc agg agg aac agg gcc gag agg atc  1056
Glu Asp Ala Val Trp Ser Asp Leu Arg Arg Asn Arg Ala Glu Arg Ile
                340                 345                 350 caa agg caa ggc tac ggc ctc tgc gtg agg aag acc gcc gag atc aag  1104
Gln Arg Gln Gly Tyr Gly Leu Cys Val Arg Lys Thr Ala Glu Ile Lys
            355                 360                 365 agg cac ctc caa tcc ctc tcc ttc cac ttc gcc gag gag acc gcc agg  1152
Arg His Leu Gln Ser Leu Ser Phe His Phe Ala Glu Glu Thr Ala Arg
        370                 375                 380 ctc gtg gtg aag cca gag gag ctc ttc acc gcc gtg gag ggc agg ctc  1200
Leu Val Val Lys Pro Glu Glu Leu Phe Thr Ala Val Glu Gly Arg Leu
385                 390                 395                 400 cac ggc cca gcc ctc tgc ttc gcc atg tcc cca ggc gag agg acc gtg  1248
His Gly Pro Ala Leu Cys Phe Ala Met Ser Pro Gly Glu Arg Thr Val
                    405                 410                 415 atc ggc gcc ctc caa caa gtg gac acc agg ttc gtg tac gac ctc aag  1296
Ile Gly Ala Leu Gln Gln Val Asp Thr Arg Phe Val Tyr Asp Leu Lys
                420                 425                 430 gac gcc aag ctc tcc ttc gcc tcc gag cca tgc tcc caa gac acc gcc  1344
Asp Ala Lys Leu Ser Phe Ala Ser Glu Pro Cys Ser Gln Asp Thr Ala
```

-continued

```
Asp Ala Lys Leu Ser Phe Ala Ser Glu Pro Cys Ser Gln Asp Thr Ala
        435                 440                 445
ggc gtg gac                                                          1353
Gly Val Asp
    450

<210> SEQ ID NO 8
<211> LENGTH: 451
<212> TYPE: PRT
<213> ORGANISM: Triticum aestivum

<400> SEQUENCE: 8

Met Ala Met Ala Ile Lys Ser Thr Leu Gln Cys Val Val Phe Leu Met
1               5                   10                  15

Ala Leu Ile Thr Thr His Leu Ile Pro Pro Ala Asp Ala Asp Ala Gly
            20                  25                  30

Ser Pro Lys Val Ala Met Ala Ser Ser Gly Ala Gly Ser Ser Phe Arg
        35                  40                  45

Leu Val Ala His His Asp Tyr Ala Leu Arg Asp Gly Phe Leu His
    50                  55                  60

Val Gln Ser Arg Leu Asp Asp Leu Leu Pro Ser Glu Ala Asn Val Thr
65                  70                  75                  80

Thr Leu Arg Pro Pro Val Ala Ser Pro Ile Asp Met Ala Phe Ser Val
                85                  90                  95

Val Val Gly Leu Gly Ser Gly Lys Gly Arg His Asp Tyr Asn Leu Lys
            100                 105                 110

Leu Asp Ala Ser Gly Ser Leu Met Trp Leu Gln Cys Lys Pro Cys Asn
        115                 120                 125

Pro Lys Gln Pro Gln Arg Gly Pro Leu Phe Asp Pro Lys Ala Ser Ser
    130                 135                 140

Thr Phe Gln Gln Val Ala Gly Thr Ser Gln Ile Cys His Pro Pro Tyr
145                 150                 155                 160

Pro Met Glu Pro Ala Gly Gln Gln Cys Ala Phe His Leu Ser Gly Glu
                165                 170                 175

His Gly Met Ser Val His Gly Phe Val Ala Leu Glu Asn Leu Thr Met
            180                 185                 190

Gly Pro Glu Ser Met Lys Glu Phe Val Phe Gly Cys Ala His Ser Ala
        195                 200                 205

Glu His Phe Asn Ser Gln Arg Thr Phe Ala Gly Val Ala Ala Met Gly
    210                 215                 220

Lys Met Pro Thr Ser Leu Val Met Gln Val Ala Ala Arg Gly Gln Thr
225                 230                 235                 240

Arg Phe Ser Tyr Cys Leu Phe Ser Gly Gly Ala Ser Arg His Gly Phe
                245                 250                 255

Leu Arg Phe Gly Ala Asp Val Pro Ser Arg Pro Gly Leu Arg Thr Thr
            260                 265                 270

Lys Ile Leu Pro Ala Leu Asp Ala His Glu Ser Gln Tyr Tyr Val Ser
        275                 280                 285

Leu Val Gly Ile Ser Leu Asp Ala Lys Arg Leu Thr Arg Ile Arg Pro
    290                 295                 300

Glu Met Phe Ala Arg Arg Arg Gly Gly Gln Gly Gly Cys Val Ile Asp
305                 310                 315                 320

Pro Gly Thr Pro Leu Thr Val Leu Ala Arg Glu Ala Tyr Arg Val Val
                325                 330                 335

Glu Asp Ala Val Trp Ser Asp Leu Arg Arg Asn Arg Ala Glu Arg Ile
```

340                 345                 350
Gln Arg Gln Gly Tyr Gly Leu Cys Val Arg Lys Thr Ala Glu Ile Lys
            355                 360                 365

Arg His Leu Gln Ser Leu Ser Phe His Phe Ala Glu Glu Thr Ala Arg
    370                 375                 380

Leu Val Val Lys Pro Glu Glu Leu Phe Thr Ala Val Glu Gly Arg Leu
385                 390                 395                 400

His Gly Pro Ala Leu Cys Phe Ala Met Ser Pro Gly Glu Arg Thr Val
                405                 410                 415

Ile Gly Ala Leu Gln Gln Val Asp Thr Arg Phe Val Tyr Asp Leu Lys
            420                 425                 430

Asp Ala Lys Leu Ser Phe Ala Ser Glu Pro Cys Ser Gln Asp Thr Ala
                435                 440                 445

Gly Val Asp
    450

<210> SEQ ID NO 9
<211> LENGTH: 1353
<212> TYPE: DNA
<213> ORGANISM: Triticum aestivum
<220> FEATURE:
<221> NAME/KEY: CDS
<222> LOCATION: (1)..(1353)
<223> OTHER INFORMATION: TaNep-1 gene encoding TaNEP1 aspartic protease

<400> SEQUENCE: 9 atg gcc atg gcc atc aag aac acc ctc caa tgc gtg gtg ttc ctc atg      48
Met Ala Met Ala Ile Lys Asn Thr Leu Gln Cys Val Val Phe Leu Met
1               5                   10                  15 gcc ctc atc atg acc cac ctc atc cca cca gcc ggc gcc gac gcc ggc      96
Ala Leu Ile Met Thr His Leu Ile Pro Pro Ala Gly Ala Asp Ala Gly
                20                  25                  30 tcc cca aag gtg gcc atg gcc tcc tcc ggc gcc ggc tcc tcc ttc agg     144
Ser Pro Lys Val Ala Met Ala Ser Ser Gly Ala Gly Ser Ser Phe Arg
            35                  40                  45 ctc gtg gcc cac cac gac tac gcc ctc agg gac gac ggc ttc ctc caa     192
Leu Val Ala His His Asp Tyr Ala Leu Arg Asp Asp Gly Phe Leu Gln
        50                  55                  60 gtg caa tcc agg ctc gac gac ctc ctc cca tcc gag gcc aac gtg acc     240
Val Gln Ser Arg Leu Asp Asp Leu Leu Pro Ser Glu Ala Asn Val Thr
65                  70                  75                  80 acc ctc agg cca cca gtg gcc tcc cca atc gac atg gcc ttc tcc gtg     288
Thr Leu Arg Pro Pro Val Ala Ser Pro Ile Asp Met Ala Phe Ser Val
                85                  90                  95 gtg gtg ggc ctc ggc tcc ggc aag ggc agg cac gac cac aac ctc aag     336
Val Val Gly Leu Gly Ser Gly Lys Gly Arg His Asp His Asn Leu Lys
                100                 105                 110 ctc gac gcc tcc ggc tcc ctc atg tgg ctc caa tgc aag cca tgc aac     384
Leu Asp Ala Ser Gly Ser Leu Met Trp Leu Gln Cys Lys Pro Cys Asn
            115                 120                 125 cca aag caa cca caa agg ggc cca ctc ttc gac cca aag gcc tcc tcc     432
Pro Lys Gln Pro Gln Arg Gly Pro Leu Phe Asp Pro Lys Ala Ser Ser
        130                 135                 140 acc ttc caa caa gtg gcc ggc acc tcc caa atc tgc cac cca cca tac     480
Thr Phe Gln Gln Val Ala Gly Thr Ser Gln Ile Cys His Pro Pro Tyr
145                 150                 155                 160 cca atg gag cca gcc ggc caa caa tgc gcc ttc cac ctc tcc ggc gag     528
Pro Met Glu Pro Ala Gly Gln Gln Cys Ala Phe His Leu Ser Gly Glu
                165                 170                 175

| | | |
|---|---|---|
| cac ggc atg tcc gtc cac ggc ttc gtg gcc ctc gag aac ctc acc atg<br>His Gly Met Ser Val His Gly Phe Val Ala Leu Glu Asn Leu Thr Met<br>        180                          185                      190 | | 576 |
| ggc cca gag tcc atg aag gag ttc gtg ttc ggc tgc gcc cac tcc gcc<br>Gly Pro Glu Ser Met Lys Glu Phe Val Phe Gly Cys Ala His Ser Ala<br>     195                       200                      205 | | 624 |
| gag cac ttc aac tcc caa agg acc ttc gcc ggc gtg gcc gcc atg ggc<br>Glu His Phe Asn Ser Gln Arg Thr Phe Ala Gly Val Ala Ala Met Gly<br>210                       215                      220 | | 672 |
| aag atg cca acc tcc ctc gtg atg caa gtg gcc gcc agg ggc caa acc<br>Lys Met Pro Thr Ser Leu Val Met Gln Val Ala Ala Arg Gly Gln Thr<br>225                      230                      235                      240 | | 720 |
| caa ttc tcc tac tgc ctc ttc tcc ggc ggc gcc tcc agg cac ggc ttc<br>Gln Phe Ser Tyr Cys Leu Phe Ser Gly Gly Ala Ser Arg His Gly Phe<br>                      245                      250                      255 | | 768 |
| ctc agg ttc ggc gcc gac gtg cca agg agg cca ggc ctc agg acc acc<br>Leu Arg Phe Gly Ala Asp Val Pro Arg Arg Pro Gly Leu Arg Thr Thr<br>         260                       265                      270 | | 816 |
| aag atc ctc cca gcc ctc gac gcc cac gag tcc caa tac tac gtg tcc<br>Lys Ile Leu Pro Ala Leu Asp Ala His Glu Ser Gln Tyr Tyr Val Ser<br>275                       280                      285 | | 864 |
| ctc gtg ggc atc tcc ctc gac gcc aag agg ctc acc ggc atc agg cca<br>Leu Val Gly Ile Ser Leu Asp Ala Lys Arg Leu Thr Gly Ile Arg Pro<br>         290                       295                      300 | | 912 |
| gag atg ttc gcc agg agg agg ggc ggc caa ggc ggc tgc gtg atc gac<br>Glu Met Phe Ala Arg Arg Arg Gly Gly Gln Gly Gly Cys Val Ile Asp<br>305                      310                      315                      320 | | 960 |
| cca ggc acc cca ctc acc gtg ctc gcc agg gag gcc tac agg gtg gtg<br>Pro Gly Thr Pro Leu Thr Val Leu Ala Arg Glu Ala Tyr Arg Val Val<br>                      325                      330                      335 | | 1008 |
| gag gag gcc atg tgg tcc gac ctc caa agg aac agg gcc gag agg gtg<br>Glu Glu Ala Met Trp Ser Asp Leu Gln Arg Asn Arg Ala Glu Arg Val<br>                  340                      345                      350 | | 1056 |
| caa agg caa ggc tac ggc ctc tgc gtg agg aag acc gcc gag atc aag<br>Gln Arg Gln Gly Tyr Gly Leu Cys Val Arg Lys Thr Ala Glu Ile Lys<br>     355                       360                      365 | | 1104 |
| agg cac ctc caa tcc ctc tcc ttc cac ttc gcc gag gag acc gcc agg<br>Arg His Leu Gln Ser Leu Ser Phe His Phe Ala Glu Glu Thr Ala Arg<br>370                      375                      380 | | 1152 |
| ctc gtg gtg aag cca gag caa ctc ttc acc gtg gtg gag tcc aag ctc<br>Leu Val Val Lys Pro Glu Gln Leu Phe Thr Val Val Glu Ser Lys Leu<br>385                      390                      395                      400 | | 1200 |
| cac ggc gcc gcc ctc tgc ctc gcc atg tcc cca ggc gag agg acc gtg<br>His Gly Ala Ala Leu Cys Leu Ala Met Ser Pro Gly Glu Arg Thr Val<br>                      405                      410                      415 | | 1248 |
| atc ggc gcc ctc caa caa gtg gac acc agg ttc gtg tac gac ctc aag<br>Ile Gly Ala Leu Gln Gln Val Asp Thr Arg Phe Val Tyr Asp Leu Lys<br>                  420                      425                      430 | | 1296 |
| gac gcc aag ctc tcc ttc gcc tcc gag cca tgc tcc caa gac acc gcc<br>Asp Ala Lys Leu Ser Phe Ala Ser Glu Pro Cys Ser Gln Asp Thr Ala<br>435                      440                      445 | | 1344 |
| ggc gtg gac<br>Gly Val Asp<br>450 | | 1353 |

```
<210> SEQ ID NO 10
<211> LENGTH: 451
<212> TYPE: PRT
<213> ORGANISM: Triticum aestivum

<400> SEQUENCE: 10
```

-continued

```
Met Ala Met Ala Ile Lys Asn Thr Leu Gln Cys Val Phe Leu Met
1               5                  10                 15

Ala Leu Ile Met Thr His Leu Ile Pro Pro Ala Gly Ala Asp Ala Gly
            20                  25                 30

Ser Pro Lys Val Ala Met Ala Ser Ser Gly Ala Gly Ser Ser Phe Arg
            35                  40                 45

Leu Val Ala His His Asp Tyr Ala Leu Arg Asp Asp Gly Phe Leu Gln
            50                  55                 60

Val Gln Ser Arg Leu Asp Asp Leu Leu Pro Ser Glu Ala Asn Val Thr
65                  70                  75                 80

Thr Leu Arg Pro Pro Val Ala Ser Pro Ile Asp Met Ala Phe Ser Val
                85                  90                 95

Val Val Gly Leu Gly Ser Gly Lys Gly Arg His Asp His Asn Leu Lys
                100                 105                110

Leu Asp Ala Ser Gly Ser Leu Met Trp Leu Gln Cys Lys Pro Cys Asn
            115                 120                 125

Pro Lys Gln Pro Gln Arg Gly Pro Leu Phe Asp Pro Lys Ala Ser Ser
    130                 135                 140

Thr Phe Gln Gln Val Ala Gly Thr Ser Gln Ile Cys His Pro Pro Tyr
145                 150                 155                160

Pro Met Glu Pro Ala Gly Gln Gln Cys Ala Phe His Leu Ser Gly Glu
                165                 170                 175

His Gly Met Ser Val His Gly Phe Val Ala Leu Glu Asn Leu Thr Met
            180                 185                 190

Gly Pro Glu Ser Met Lys Glu Phe Val Phe Gly Cys Ala His Ser Ala
                195                 200                 205

Glu His Phe Asn Ser Gln Arg Thr Phe Ala Gly Val Ala Ala Met Gly
    210                 215                 220

Lys Met Pro Thr Ser Leu Val Met Gln Val Ala Ala Arg Gly Gln Thr
225                 230                 235                240

Gln Phe Ser Tyr Cys Leu Phe Ser Gly Gly Ala Ser Arg His Gly Phe
                245                 250                 255

Leu Arg Phe Gly Ala Asp Val Pro Arg Arg Pro Gly Leu Arg Thr Thr
                260                 265                 270

Lys Ile Leu Pro Ala Leu Asp Ala His Glu Ser Gln Tyr Tyr Val Ser
            275                 280                 285

Leu Val Gly Ile Ser Leu Asp Ala Lys Arg Leu Thr Gly Ile Arg Pro
    290                 295                 300

Glu Met Phe Ala Arg Arg Gly Gly Gln Gly Gly Cys Val Ile Asp
305                 310                 315                320

Pro Gly Thr Pro Leu Thr Val Leu Ala Arg Glu Ala Tyr Arg Val Val
                325                 330                 335

Glu Glu Ala Met Trp Ser Asp Leu Gln Arg Asn Arg Ala Glu Arg Val
            340                 345                 350

Gln Arg Gln Gly Tyr Gly Leu Cys Val Arg Lys Thr Ala Glu Ile Lys
    355                 360                 365

Arg His Leu Gln Ser Leu Ser Phe His Phe Ala Glu Glu Thr Ala Arg
    370                 375                 380

Leu Val Val Lys Pro Glu Gln Leu Phe Thr Val Val Glu Ser Lys Leu
385                 390                 395                400

His Gly Ala Ala Leu Cys Leu Ala Met Ser Pro Gly Glu Arg Thr Val
                405                 410                 415
```

```
Ile Gly Ala Leu Gln Gln Val Asp Thr Arg Phe Val Tyr Asp Leu Lys
            420                 425                 430

Asp Ala Lys Leu Ser Phe Ala Ser Glu Pro Cys Ser Gln Asp Thr Ala
            435                 440                 445

Gly Val Asp
    450

<210> SEQ ID NO 11
<211> LENGTH: 1338
<212> TYPE: DNA
<213> ORGANISM: Triticum urartu
<220> FEATURE:
<221> NAME/KEY: CDS
<222> LOCATION: (1)..(1338)
<223> OTHER INFORMATION: TuNep-1 gene encoding TuNEP1 aspartic protease

<400> SEQUENCE: 11 atg ggc atc aag aac acc ctc caa tgc gtg gtg ttc ctc atg gcc ctc      48
Met Gly Ile Lys Asn Thr Leu Gln Cys Val Val Phe Leu Met Ala Leu
1               5                   10                  15 atc atg acc cac ctc atc cca cca gcc gac gcc gac gcc ggc tcc cca      96
Ile Met Thr His Leu Ile Pro Pro Ala Asp Ala Asp Ala Gly Ser Pro
            20                  25                  30 aag gtg gtg atg gcc tcc tcc ggc gcc ggc tcc tcc ttc agg ctc gtg     144
Lys Val Val Met Ala Ser Ser Gly Ala Gly Ser Ser Phe Arg Leu Val
        35                  40                  45 gcc cac cac gac tac gcc ctc agg gac gac ggc ttc ctc caa gtg caa     192
Ala His His Asp Tyr Ala Leu Arg Asp Asp Gly Phe Leu Gln Val Gln
    50                  55                  60 tcc agg ctc gac gac ctc ctc cca tcc gag gcc aac gtg acc acc ctc     240
Ser Arg Leu Asp Asp Leu Leu Pro Ser Glu Ala Asn Val Thr Thr Leu
65                  70                  75                  80 agg cca cca atg gcc tcc cca atc gac atg gcc ttc tcc gtg gtg gtg     288
Arg Pro Pro Met Ala Ser Pro Ile Asp Met Ala Phe Ser Val Val Val
                85                  90                  95 ggc ctc ggc tcc ggc aag ggc agg cac gac tac aac ctc aag ctc gac     336
Gly Leu Gly Ser Gly Lys Gly Arg His Asp Tyr Asn Leu Lys Leu Asp
            100                 105                 110 gcc tcc ggc tcc ctc gtg tgg ctc caa tgc aag cca tgc aac cca aag     384
Ala Ser Gly Ser Leu Val Trp Leu Gln Cys Lys Pro Cys Asn Pro Lys
        115                 120                 125 caa cca caa agg ggc cca ctc ttc gac cca aag gcc tcc tcc acc ttc     432
Gln Pro Gln Arg Gly Pro Leu Phe Asp Pro Lys Ala Ser Ser Thr Phe
    130                 135                 140 caa caa gtg gcc ggc acc tcc caa atc tgc cac cca cca tac cca atg     480
Gln Gln Val Ala Gly Thr Ser Gln Ile Cys His Pro Pro Tyr Pro Met
145                 150                 155                 160 gag cca gcc ggc caa caa tgc tcc ttc cac ctc tcc ggc gag cac ggc     528
Glu Pro Ala Gly Gln Gln Cys Ser Phe His Leu Ser Gly Glu His Gly
                165                 170                 175 atg tcc gtg cac ggc ttc gtg gcc ctc gag aac ctc acc atg ggc cca     576
Met Ser Val His Gly Phe Val Ala Leu Glu Asn Leu Thr Met Gly Pro
            180                 185                 190 gag tcc atg aag gag ctc gtg ttc ggc tgc gcc cac tcc acc gag cac     624
Glu Ser Met Lys Glu Leu Val Phe Gly Cys Ala His Ser Thr Glu His
        195                 200                 205 ttc aac tcc caa agg acc ttc gcc ggc gtg gcc gcc atg ggc aag atg     672
Phe Asn Ser Gln Arg Thr Phe Ala Gly Val Ala Ala Met Gly Lys Met
    210                 215                 220 cca acc tcc ctc gtg atg caa gtg gcc gcc agg ggc caa acc caa ttc     720
Pro Thr Ser Leu Val Met Gln Val Ala Ala Arg Gly Gln Thr Gln Phe
```

-continued

| | | | |
|---|---|---|---|
| 225 | 230 | 235 | 240 | tcc tac tgc ctc ttc tcc ggc gcc tcc agg cac ggc ttc ctc agg    768
Ser Tyr Cys Leu Phe Ser Gly Ala Ser Arg His Gly Phe Leu Arg
                245                 250                 255 ttc ggc gcc gac gtg cca agg agg cca ggc ctc agg acc acc aag atc    816
Phe Gly Ala Asp Val Pro Arg Arg Pro Gly Leu Arg Thr Thr Lys Ile
            260                 265                 270 ctc cca gcc ctc gac gcc cac gag tcc caa tac tac gtg tcc ctc gtg    864
Leu Pro Ala Leu Asp Ala His Glu Ser Gln Tyr Tyr Val Ser Leu Val
                275                 280                 285 ggc atc tcc ctc gac gcc aag agg ctc acc ggc gtg agg cca gag atg    912
Gly Ile Ser Leu Asp Ala Lys Arg Leu Thr Gly Val Arg Pro Glu Met
        290                 295                 300 ttc gcc agg agg cac ggc ggc caa ggc ggc tgc gtg atc gac cca ggc    960
Phe Ala Arg Arg His Gly Gly Gln Gly Gly Cys Val Ile Asp Pro Gly
305                 310                 315                 320 acc cca ctc acc gtg ctc gtg agg gag gcc tac agg gtg gtg gag gag   1008
Thr Pro Leu Thr Val Leu Val Arg Glu Ala Tyr Arg Val Val Glu Glu
                325                 330                 335 gcc gtg tgg tcc gac ctc agg agg aac agg gcc gag agg atg caa agg   1056
Ala Val Trp Ser Asp Leu Arg Arg Asn Arg Ala Glu Arg Met Gln Arg
            340                 345                 350 caa ggc tac ggc ctc tgc gtg agg aag acc gtg gag atc aag agg cac   1104
Gln Gly Tyr Gly Leu Cys Val Arg Lys Thr Val Glu Ile Lys Arg His
                355                 360                 365 ctc caa tcc ctc tcc ttc cac ttc gcc gag gag acc gcc agg ctc gtg   1152
Leu Gln Ser Leu Ser Phe His Phe Ala Glu Glu Thr Ala Arg Leu Val
        370                 375                 380 gtg aag cca gag caa ctc ttc acc gtg gtg gag tcc aag ctc cac ggc   1200
Val Lys Pro Glu Gln Leu Phe Thr Val Val Glu Ser Lys Leu His Gly
385                 390                 395                 400 gcc gcc ctc tgc ctc gcc atg atc cca ggc gag agg acc gtg atc ggc   1248
Ala Ala Leu Cys Leu Ala Met Ile Pro Gly Glu Arg Thr Val Ile Gly
                405                 410                 415 gcc ctc caa caa gtg gac acc agg ttc gtg tac gac ctc aag gac gcc   1296
Ala Leu Gln Gln Val Asp Thr Arg Phe Val Tyr Asp Leu Lys Asp Ala
            420                 425                 430 aag ctc tcc ttc gtg tcc gag cca tgc tcc caa gac acc gcc              1338
Lys Leu Ser Phe Val Ser Glu Pro Cys Ser Gln Asp Thr Ala
                435                 440                 445

<210> SEQ ID NO 12
<211> LENGTH: 446
<212> TYPE: PRT
<213> ORGANISM: Triticum urartu

<400> SEQUENCE: 12

Met Gly Ile Lys Asn Thr Leu Gln Cys Val Val Phe Leu Met Ala Leu
1               5                   10                  15

Ile Met Thr His Leu Ile Pro Pro Ala Asp Ala Asp Ala Gly Ser Pro
            20                  25                  30

Lys Val Val Met Ala Ser Ser Gly Ala Gly Ser Ser Phe Arg Leu Val
        35                  40                  45

Ala His His Asp Tyr Ala Leu Arg Asp Asp Gly Phe Leu Gln Val Gln
    50                  55                  60

Ser Arg Leu Asp Asp Leu Leu Pro Ser Glu Ala Asn Val Thr Thr Leu
65                  70                  75                  80

Arg Pro Pro Met Ala Ser Pro Ile Asp Met Ala Phe Ser Val Val Val
                85                  90                  95

Gly Leu Gly Ser Gly Lys Gly Arg His Asp Tyr Asn Leu Lys Leu Asp
                100                 105                 110

Ala Ser Gly Ser Leu Val Trp Leu Gln Cys Lys Pro Cys Asn Pro Lys
            115                 120                 125

Gln Pro Gln Arg Gly Pro Leu Phe Asp Pro Lys Ala Ser Ser Thr Phe
        130                 135                 140

Gln Gln Val Ala Gly Thr Ser Gln Ile Cys His Pro Pro Tyr Pro Met
145                 150                 155                 160

Glu Pro Ala Gly Gln Gln Cys Ser Phe His Leu Ser Gly Glu His Gly
                165                 170                 175

Met Ser Val His Gly Phe Val Ala Leu Glu Asn Leu Thr Met Gly Pro
            180                 185                 190

Glu Ser Met Lys Glu Leu Val Phe Gly Cys Ala His Ser Thr Glu His
        195                 200                 205

Phe Asn Ser Gln Arg Thr Phe Ala Gly Val Ala Met Gly Lys Met
210                 215                 220

Pro Thr Ser Leu Val Met Gln Val Ala Ala Arg Gly Gln Thr Gln Phe
225                 230                 235                 240

Ser Tyr Cys Leu Phe Ser Gly Gly Ala Ser Arg His Gly Phe Leu Arg
                245                 250                 255

Phe Gly Ala Asp Val Pro Arg Arg Pro Gly Leu Arg Thr Thr Lys Ile
            260                 265                 270

Leu Pro Ala Leu Asp Ala His Glu Ser Gln Tyr Tyr Val Ser Leu Val
        275                 280                 285

Gly Ile Ser Leu Asp Ala Lys Arg Leu Thr Gly Val Arg Pro Glu Met
290                 295                 300

Phe Ala Arg Arg His Gly Gly Gln Gly Gly Cys Val Ile Asp Pro Gly
305                 310                 315                 320

Thr Pro Leu Thr Val Leu Val Arg Glu Ala Tyr Arg Val Val Glu Glu
                325                 330                 335

Ala Val Trp Ser Asp Leu Arg Arg Asn Arg Ala Glu Arg Met Gln Arg
            340                 345                 350

Gln Gly Tyr Gly Leu Cys Val Arg Lys Thr Val Glu Ile Lys Arg His
        355                 360                 365

Leu Gln Ser Leu Ser Phe His Phe Ala Glu Glu Thr Ala Arg Leu Val
370                 375                 380

Val Lys Pro Glu Gln Leu Phe Thr Val Val Glu Ser Lys Leu His Gly
385                 390                 395                 400

Ala Ala Leu Cys Leu Ala Met Ile Pro Gly Glu Arg Thr Val Ile Gly
                405                 410                 415

Ala Leu Gln Gln Val Asp Thr Arg Phe Val Tyr Asp Leu Lys Asp Ala
            420                 425                 430

Lys Leu Ser Phe Val Ser Glu Pro Cys Ser Gln Asp Thr Ala
        435                 440                 445

<210> SEQ ID NO 13
<211> LENGTH: 63
<212> TYPE: DNA
<213> ORGANISM: Hordeum vulgare
<220> FEATURE:
<221> NAME/KEY: CDS
<222> LOCATION: (1)..(63)
<223> OTHER INFORMATION: Nucleotide sequence encoding a D-hordein signal
      peptide

<400> SEQUENCE: 13

-continued

```
atg gct aag cgg ctg gtc ctc ttt gtg gcg gta atc gtc gcc ctc gtg     48
Met Ala Lys Arg Leu Val Leu Phe Val Ala Val Ile Val Ala Leu Val
1               5                   10                  15 gct ctc acc acc gct                                                 63
Ala Leu Thr Thr Ala
            20

<210> SEQ ID NO 14
<211> LENGTH: 21
<212> TYPE: PRT
<213> ORGANISM: Hordeum vulgare

<400> SEQUENCE: 14

Met Ala Lys Arg Leu Val Leu Phe Val Ala Val Ile Val Ala Leu Val
1               5                   10                  15

Ala Leu Thr Thr Ala
            20

<210> SEQ ID NO 15
<211> LENGTH: 60
<212> TYPE: DNA
<213> ORGANISM: Hordeum vulgare
<220> FEATURE:
<221> NAME/KEY: CDS
<222> LOCATION: (1)..(60)
<223> OTHER INFORMATION: Nucleotide sequence encoding a C-hordein signal
      peptide

<400> SEQUENCE: 15 atg aag acc ttc ctc acc ttc gtg ctc ctc gcc atg gtg atg tcc atc     48
Met Lys Thr Phe Leu Thr Phe Val Leu Leu Ala Met Val Met Ser Ile
1               5                   10                  15 gtg acc acc gcc                                                     60
Val Thr Thr Ala
            20

<210> SEQ ID NO 16
<211> LENGTH: 20
<212> TYPE: PRT
<213> ORGANISM: Hordeum vulgare

<400> SEQUENCE: 16

Met Lys Thr Phe Leu Thr Phe Val Leu Leu Ala Met Val Met Ser Ile
1               5                   10                  15

Val Thr Thr Ala
            20

<210> SEQ ID NO 17
<211> LENGTH: 57
<212> TYPE: DNA
<213> ORGANISM: Hordeum vulgare
<220> FEATURE:
<221> NAME/KEY: CDS
<222> LOCATION: (1)..(57)
<223> OTHER INFORMATION: Nucleotide sequence encoding a B-hordein signal
      peptide

<400> SEQUENCE: 17 atg aag acc ttc ctc gtg ttc gcc ctc ctc gtg atc gcc gcc acc tcc     48
Met Lys Thr Phe Leu Val Phe Ala Leu Leu Val Ile Ala Ala Thr Ser
1               5                   10                  15 acc atc gcc                                                         57
Thr Ile Ala
```

-continued

```
<210> SEQ ID NO 18
<211> LENGTH: 19
<212> TYPE: PRT
<213> ORGANISM: Hordeum vulgare

<400> SEQUENCE: 18

Met Lys Thr Phe Leu Val Phe Ala Leu Leu Val Ile Ala Ala Thr Ser
1               5                   10                  15

Thr Ile Ala

<210> SEQ ID NO 19
<211> LENGTH: 63
<212> TYPE: DNA
<213> ORGANISM: Triticum aestivum
<220> FEATURE:
<221> NAME/KEY: CDS
<222> LOCATION: (1)..(63)
<223> OTHER INFORMATION: Nucleotide sequence encoding a wheat glutenin
      signal peptide

<400> SEQUENCE: 19 atg gcc aag agg ctc gtg ctc ttc gcc gcc gtg gtg atc gcc ctc gtg      48
Met Ala Lys Arg Leu Val Leu Phe Ala Ala Val Val Ile Ala Leu Val
1               5                   10                  15 gcc ctc acc acc gcc                                                   63
Ala Leu Thr Thr Ala
            20

<210> SEQ ID NO 20
<211> LENGTH: 21
<212> TYPE: PRT
<213> ORGANISM: Triticum aestivum

<400> SEQUENCE: 20

Met Ala Lys Arg Leu Val Leu Phe Ala Ala Val Val Ile Ala Leu Val
1               5                   10                  15

Ala Leu Thr Thr Ala
            20

<210> SEQ ID NO 21
<211> LENGTH: 51
<212> TYPE: DNA
<213> ORGANISM: Triticum aestivum
<220> FEATURE:
<221> NAME/KEY: CDS
<222> LOCATION: (1)..(51)
<223> OTHER INFORMATION: Nucleotide sequence encoding a wheat alpha
      gliadin signal peptide

<400> SEQUENCE: 21 atg aag acc ttc ctc atc ctc gcc ctc gtg gcc acc acc gcc acc acc      48
Met Lys Thr Phe Leu Ile Leu Ala Leu Val Ala Thr Thr Ala Thr Thr
1               5                   10                  15 gcc                                                                   51
Ala

<210> SEQ ID NO 22
<211> LENGTH: 17
<212> TYPE: PRT
<213> ORGANISM: Triticum aestivum

<400> SEQUENCE: 22

Met Lys Thr Phe Leu Ile Leu Ala Leu Val Ala Thr Thr Ala Thr Thr
1               5                   10                  15

Ala
```

<210> SEQ ID NO 23
<211> LENGTH: 87
<212> TYPE: DNA
<213> ORGANISM: Hordeum vulgare
<220> FEATURE:
<221> NAME/KEY: CDS
<222> LOCATION: (1)..(87)
<223> OTHER INFORMATION: Nucleotide sequence encoding a HvNEP1 signal
      peptide

<400> SEQUENCE: 23

```
atg gcc atg gcc atc atg aac acc ctc cag tgc atc ctc ttc ctc atg       48
Met Ala Met Ala Ile Met Asn Thr Leu Gln Cys Ile Leu Phe Leu Met
1               5                   10                  15 gcc ctc atc atg acc cac cag atc ccg cgc gcc acc gcc                    87
Ala Leu Ile Met Thr His Gln Ile Pro Arg Ala Thr Ala
                20                  25
```

<210> SEQ ID NO 24
<211> LENGTH: 29
<212> TYPE: PRT
<213> ORGANISM: Hordeum vulgare

<400> SEQUENCE: 24

Met Ala Met Ala Ile Met Asn Thr Leu Gln Cys Ile Leu Phe Leu Met
1               5                   10                  15

Ala Leu Ile Met Thr His Gln Ile Pro Arg Ala Thr Ala
                20                  25

<210> SEQ ID NO 25
<211> LENGTH: 435
<212> TYPE: DNA
<213> ORGANISM: Hordeum vulgare
<220> FEATURE:
<221> NAME/KEY: promoter
<222> LOCATION: (1)..(434)
<223> OTHER INFORMATION: Promoter for D-hordein gene

<400> SEQUENCE: 25

```
cttcgagtgc ccgccgattt gccagcaatg gctaacagac acatattctg ccaaaacccc       60
agaacaataa tcacttctcg tagatgaaga gaacagacca agatacaaac gtccacgctt      120
cagcaaacag taccccagaa ctaggattaa gccgattacg cggctttagc agaccgtcca      180
aaaaaactgt tttgcaaagc tccaattcct ccttgcttat ccaatttctt ttgtgttggc      240
aaactgcact tgtccaaccg attttgttct tcccgtgttt cttcttaggc taactaacac      300
agccgtgcac atagccatgg tccggaatct tcacctcgtc cctataaaag cccagccaat      360
ctccacaatc tcatcatcac cgagaacacc gagaaccaca aaactagaga tcaattcatt      420
gacagtccac cgaga                                                      435
```

<210> SEQ ID NO 26
<211> LENGTH: 431
<212> TYPE: DNA
<213> ORGANISM: Hordeum vulgare
<220> FEATURE:
<221> NAME/KEY: promoter
<222> LOCATION: (1)..(431)
<223> OTHER INFORMATION: Promoter for C-hordein gene

<400> SEQUENCE: 26

```
aagcttacaa acttaatccc actcaagcta tgcctatctc gatatgacta cataaagtag       60
agcatcacaa actaaattcc aaaaagaggc aaaatctgga ttaatgtgtg tagtgtaaag      120
```

```
tgaaaaaatg agtcatcatt cattatcaag catgccttac aacgagacga tatgtgcaac      180
aaaaagcaac tatgatgagc aatccaaaat cacacaagta aagtagtact accaaataca      240
acataccaaa cgattagttg aataatctta ggagtacttt ttcaaaaaga aagggcaagg      300
atgaaattat accataccat gacagctata aataaacatg caccatcatg gttgccctcc      360
atcatccaaa ctgcacacac caagatcaga acatcaatt ccaagaaagc aatagtaacc       420
acaaatccaa c                                                           431

<210> SEQ ID NO 27
<211> LENGTH: 440
<212> TYPE: DNA
<213> ORGANISM: Hordeum vulgare
<220> FEATURE:
<221> NAME/KEY: promoter
<222> LOCATION: (1)..(440)
<223> OTHER INFORMATION: Promoter for B-hordein gene

<400> SEQUENCE: 27
gtccacatgt aaagctttaa caacccacac attgattgca acttagtcct acacaagttt       60
tccattcttg tttcaggcta acaacctata caaggttcca aaatcatgca aaagtgatgc      120
taggttgata atgtgtgaca tgtaaagtga ataaggtgag tcatgcatac caaacctcgg      180
gatttctata ctttgtgtat gatcatatgc acaactaaaa ggcaactttg attatcaatt      240
gaaaagtacc gcttgtagct tgtgcaacct aacacaatgt ccaaaaatcc atttgcaaaa      300
gcatccaaac acaattgtta aagctgttca aacaaacaaa gaagagatga agcctggcta      360
ctataaatag gcaggtagta tagagatcta cacaagcaca agcatcaaaa ccaagaaaca      420
ctagttaaca ccaatccact                                                 440

<210> SEQ ID NO 28
<211> LENGTH: 1922
<212> TYPE: DNA
<213> ORGANISM: Triticum aestivum
<220> FEATURE:
<221> NAME/KEY: promoter
<222> LOCATION: (1)..(1922)
<223> OTHER INFORMATION: Promoter for wheat glutenin gene

<400> SEQUENCE: 28
aaggtggcat tggaggattg aggatgtttg tgttttttct tgtggggatg tctgcatttg       60
ttgttgaggt ggattatgac aatctatctt ttgcccattt tattatttgt tcaacatttt      120
atttgcttcc atggctatct attttttgttg ccgatacaat gaataaggtt aataaagcat     180
aatttagcaa ccacaaaatg tgtattagga gtcagggccg ggccggcaaa ctcagggccc      240
tatgccaaaa ctctaacaat gagcctacca ttagaagaac gtccggcaaa gagatgcact      300
gcaacatatg accaaaacgt catccatgat cgagtacaat ttcttagtgc cttttcatc      360 aaagttatat ttgaaacatt ttagaaaatt tgtcttaaat ttttttcccat ggcgtttcga     420 tcaaaaaaat gccttaaaac ctacctatat aaaggcaata agggaaaaca cttcaggata      480
ccttcgaatc taaggtgtct ttctttagat ggtatgctaa actgttcttc atggcgcctc      540
aaatcatcat tctgcaagta aagactaaaa ataacgctaa atatgagtt aaaggtttac      600 aaacgacgag cggaaaagga gtcttatata attccagtag catttattcc attttgcttc     660
acatagaaaa tgtagctgag gtggtcgatg tttattttga ctcgcgtgag gtcgccggtt      720
cgatctcaga agcaacgctg gaatatccca tatagattta ttttcaggc tgagtgatgc      780
```

| | |
|---|---|
| tcgggtacct ccagcgtatg ggctgaaatt cgccccccct gcaaatcatg ggccctgtga | 840 |
| cgttcgcacg ggttgcacat gccttggccc gggcctacta ggagtgtacc tggattatgt | 900 |
| tggacgacgg gagatgaaag ggatgtatta attaacaaag ataatgaagc ttaattttct | 960 |
| tatatgttgt taatattgac aagaaacaag ctgctaactc aaagttacgg ttacatagtc | 1020 |
| gcaaccttt atatctaaat aatatctctc tctcaacatg caaacatgcc acctcagcat | 1080 |
| gtagcatgca tggaaaattg tccacttcaa catgcaacca tgcatcaaaa tttccatttt | 1140 |
| actaggctat ttatttgata aaatttcaca aatatacaat aatcaaacac aatagatcat | 1200 |
| atgtgttttc agttttggtt ctcacattat tactccaaat ataaatgttt cgtataacca | 1260 |
| aatttcattc aaatatactg caaaacattt ccgtgaaaac atgtggggta catctagtta | 1320 |
| taaggaaata ttagtgatgt cctgcaagtg ataaggccaa ggagagaaga agtgcaccat | 1380 |
| ctacagaggc cagggaaaga caatggacat gcagagaggc ggggggcgggg aagaaacaca | 1440 |
| tggagatcat agaagaacat aagaggttaa acataggagg aggatataat ggacaattaa | 1500 |
| atccacatta cctgaactca tttgggaagt ggaaaaatcc cctattctgg tgtaaatcaa | 1560 |
| actaattgac gcgagttttc tctgaagatt ctatgttaat tttagacatg aatgaccaaa | 1620 |
| ggtttcagtt agttgagttt tgtcatcgaa aggtgtttac ataagtccaa aaattctacc | 1680 |
| agcttttggt acggcgcgtc atagaacaga taaatgttgt gagtcattgg atagatatta | 1740 |
| tgagtcatag catggatttg tgttgcctgg aaatctaact atgacaagaa acaaaacata | 1800 |
| aatgggcttt tgaaagatga tttatcaact taccttatcc atgcaagcta ccttccacta | 1860 |
| gtcgacatgc ttagaagctt ttagtgaccg cagatttgca aaagcaatgg ctaacagaca | 1920 |
| cc | 1922 |

<210> SEQ ID NO 29
<211> LENGTH: 593
<212> TYPE: DNA
<213> ORGANISM: Triticum aestivum
<220> FEATURE:
<221> NAME/KEY: promoter
<222> LOCATION: (1)..(593)
<223> OTHER INFORMATION: Promoter for wheat alpha-gliadin gene

<400> SEQUENCE: 29

| | |
|---|---|
| aagcttgtct agttacagta acaacttgtg gaacattaca aaatttatgt ttgctagtaa | 60 |
| cttctagaac actacaacac ttgacatgta taaggaattt gatgagtcat ggcctactaa | 120 |
| agcaagttat attactactc ttatctatct taacaggtca cacaagatta caaactaagt | 180 |
| tctgtatcag ccatgcttat ctagtttatg cataacaatt tgcagaacat tacaaactta | 240 |
| gtttcggaaa ataggcaat ctagattagt gtttgagcta taaagtgaat aagatgagtc | 300 |
| atgcgtgtta tcacacctct ttggtggtgg aatgatagtg caacaacatg aaacttcagt | 360 |
| gactagtcca agaatacaca tgtaagtagt gccaccaaac acaacatacc aaattatgat | 420 |
| tttgggaagc atccaagcac tttccagaca agaaaatgcc aattgtgaaa gagatcatac | 480 |
| catgggaact ataaaagcc ttgtagcatg atcatcatcc ttcctcaccc atcattctca | 540 |
| taagtagagc gcatcattca agccaagcaa gcagtggtca atacaaatcc acc | 593 |

<210> SEQ ID NO 30
<211> LENGTH: 217
<212> TYPE: DNA
<213> ORGANISM: Cauliflower mosaic virus
<220> FEATURE:
<221> NAME/KEY: terminator -continued

```
<222> LOCATION: (1)..(217)
<223> OTHER INFORMATION: Nucleotide sequence of CaMV 35S terminator
<400> SEQUENCE: 30
ctagagtccg caaaaatcac cagtctctct ctacaaatct atctctctct atttttctcc 60
agaataatgt gtgagtagtt cccagataag ggaattaggg ttcttatagg gtttcgctca 120
tgtgttgagc atataagaaa cccttagtat gtatttgtat ttgtaaaata cttctatcaa 180
taaaatttct aattcctaaa accaaaatcc agtgacc 217

<210> SEQ ID NO 31
<211> LENGTH: 128
<212> TYPE: DNA
<213> ORGANISM: Agrobacterium tumefaciens
<220> FEATURE:
<221> NAME/KEY: terminator
<222> LOCATION: (1)..(128)
<223> OTHER INFORMATION: Nucleotide sequence of Agrobacterium terminator
<400> SEQUENCE: 31
gaatcctgtt gccggtcttg cgatgattat catataattt ctgttgggtt acgttaagca 60
tgtaataatt aacatgtaat gcatgacgtt atttatgaga tgggttttta tgattagagt 120
cccgcaat 128

<210> SEQ ID NO 32
<211> LENGTH: 1789
<212> TYPE: DNA
<213> ORGANISM: Fusarium graminearium
<220> FEATURE:
<221> NAME/KEY: mRNA
<222> LOCATION: (1)..(1789)
<223> OTHER INFORMATION: mRNA transcript TRI4 encoding trichodiene
oxygenase
<400> SEQUENCE: 32
gtttctttta caggtctatc aaagacttga gctttagaag atgattgacc aagattggat 60
caagagcttg ctcaacatcc ccgtcagcca tgttgctggg attttcgcag catcgactgt 120
tatctacttc ctctcttcct gcttttacaa cctgtacttg cacccactga gaaagatccc 180
gggaccaaag ctcgctgcca ttggacccta ccttgagttc taccatgaag tcatccggga 240
tggccaatat ctctgggaga tctccaagat gcacgataaa tacggcccca tcgtccgagt 300
aaacgcccgc gaagttcaca tcagggattc atcctactac actaccatct atactgctgg 360
ttctcgcaag accaacaagg accccgccac tgtcggtgct tttgacgttc cctccgccac 420
tgccgccact gtcgatcatg accatcatcg ttctcgtcgc ggctacctga acccttactt 480
ctcgaagcga accatcacca acctcgagcc tttcatccat gagcgtgtta ccaagctttt 540
gactcgattc caacagcatc tggacgacga ccaggtcctc agtcttgatg gtgctttttg 600
tgctttgacc gccgatgtca tcactaatcg attctatggc aagcacaacg actatctcag 660
tcttcccgac ttccactttg tcgttcgcga cggattcttg ggtcttacca agatctacca 720
tcttgcacgc ttcctccctg gtctggtcac cattctgaag cgcctccctt actcttgtat 780
ccgcatgatc gcaccttctg tgtgtgatct tctccagatg cgagatgaga ttcaggaccg 840
cggtggtgag gagttcctgt ctaacaaatc tcatgaggcc aagtcatcca tccttttcgg 900
tgcccttgca gactcgcaca tcccctctca tgaacgaacc gtggagcgaa tgctcgatga 960
gggtaccgtt atcctgtttg ctggtactga gactacttca aggacactgg ccattaccgt 1020
attatacctc ttgacccatc cagaatgttt gaaaaagctc cgagaggagt tgaacagcct 1080
```

```
cccacctgtc aaggacggcc agtattctct cgctacccta gagaatctcc cttacctgaa    1140
cggtgtcatc catgagggat tccgtcttgc ttttggtccc atttctcgct cgggacgtgt    1200
ggctactcag gagaacttga agtacaagga gcatgtcatc cctaaaggaa ctcccatttc    1260
tcagtccacc tatttcatgc acaccgatcc caagaatttc cccgagcccg aaaagttcaa    1320
gcctgagcga tggatcgagg cacaacagaa gggtatccct ctcaagaagt acatcaccaa    1380
cttctctcag ggttctagac agtgcatcgg atacactatg gcctttgctg agatgtacct    1440
cgcccttcct cgcattgcgc gagcttacga cattgagctt tatgacacca ccaaggccga    1500
cattgacatg actcacgccc gtattgttgg ctaccccaag gcaattccag caagaagga     1560 acaccttggc gaagttcgag tcaaggttct caaggctttg taaggcgcat ctgacaaact    1620
gtctcaatat cttactggat aactcactgt atcggcatcg aatcctgttc cttttgttca    1680
gtccattttt ggtatgcaag gatggaaggt catagtagcg acatctgaac gtaaaataaa    1740
ttgtacccta tttagacgct cgtcaattta aacactattc atctcaggc                1789
```

<210> SEQ ID NO 33
<211> LENGTH: 1309
<212> TYPE: DNA
<213> ORGANISM: Fusarium graminearium
<220> FEATURE:
<221> NAME/KEY: mRNA
<222> LOCATION: (1)..(1309)
<223> OTHER INFORMATION: mRNA transcript TRI5 encoding trichodiene
      synthase <400> SEQUENCE: 33

```
ttattgaata actgttacca gtacaacctt gccatcatgg aaaactttcc caccgagtat     60
tttctcaaca ctagcgtgcg ccttctcgag tatattcgat accgagacag caattacacc    120
cgagaggagc gcatcgagaa tttgcactat gcttacaaca aggctgccca ccactttgct    180
cagcctcgcc aacagcagat gctcaaggta gaccctaagc gactacaggc ttccctccaa    240
acaatcgttg gcatggttgt atacagctgg gcaaaggtgt ccaaagagtg catggcggat    300
ctatctattc actacaccta tactctcgtt ttggatgaca gcagcgatga tccccatcct    360
gccatgttga actattttga cgaccttcaa gccggacgag agcaggccca tccatggtgg    420
gcacttgtca cgagcacttt tcccaacgtc cttcgccatt ttggaccttt ctgctcattg    480
aaccttatcc gtagcactat ggactttttt gagggatgtt ggattgagca gtacaacttt    540
ggaggattcc caggatctga tgactaccct caattccttc gtcgtatgaa tggtttgggt    600
cattgtgttg gggcttctct atggcccaag gacctgtttg atgagcggaa gcatttcctt    660
gaaatcacgt cagccgttgc tcagatggag aactggatgg tttgggtcaa tgatctcatg    720
tcattctaca aggaattcga cgatgagcgt gaccaaatca gtctggtcaa gaactttgtc    780
acctgccatg agatcactct ggatgaagct ttggagaagc tcacccagga aaccctacac    840
tcgtctaagc agatggttgc tgtcttctcg gacaaggacc ctcaggtgat ggacacgatt    900
gagtgtttca tgcatggcta cgtcacgtgg cacttgtgcg acgctcgata ccgcctccat    960
gagatttatg aaaggtcaa ggatcaggat acagaggacg ccaagaagtt ctgcaagttc    1020
tttgagcagg cggccaatgt cggcgccgtt gcaccctcgg agtgggctta tccacaagtt    1080
gcacaactgg caaacgttcg ggccaaggac gatgtgaagg aggctcagaa gcccatccta    1140
agttcaattg agctagtgga gtaaccgaag gcgagtttgg aagtatgttt tgcgggtacg    1200
gatactcgtt tggagaatgg tggtctgtta taatgattac aaatagttcg gtcgtgtttt    1260
```
gttagaatga acagttgaac aaggataatt acttcggaat aggcagttg         1309

<210> SEQ ID NO 34
<211> LENGTH: 20
<212> TYPE: DNA
<213> ORGANISM: Hordeum vulgare
<220> FEATURE:
<221> NAME/KEY: primer_bind
<222> LOCATION: (1)..(20)
<223> OTHER INFORMATION: Fw Primer for HvNEP-1 transgene detection

<400> SEQUENCE: 34
gcacttgtcc aaccgatttt                                         20

<210> SEQ ID NO 35
<211> LENGTH: 20
<212> TYPE: DNA
<213> ORGANISM: Hordeum vulgare
<220> FEATURE:
<221> NAME/KEY: primer_bind
<222> LOCATION: (1)..(20)
<223> OTHER INFORMATION: Rv Primer for HvNEP-1 transgene detection

<400> SEQUENCE: 35
cattgcctct ggccccatgg                                         20

<210> SEQ ID NO 36
<211> LENGTH: 508
<212> TYPE: PRT
<213> ORGANISM: Hordeum vulgare
<220> FEATURE:
<221> NAME/KEY: PEPTIDE
<222> LOCATION: (1)..(508)
<223> OTHER INFORMATION: H. vulgare phytepsin

<400> SEQUENCE: 36

Met Gly Thr Arg Gly Leu Ala Leu Ala Leu Leu Ala Ala Val Leu Leu
1               5                   10                  15

Leu Gln Thr Val Leu Pro Ala Ala Ser Glu Ala Glu Gly Leu Val Arg
            20                  25                  30

Ile Ala Leu Lys Lys Arg Pro Ile Asp Arg Asn Ser Arg Val Ala Thr
        35                  40                  45

Gly Leu Ser Gly Gly Glu Glu Gln Pro Leu Leu Ser Gly Ala Asn Pro
    50                  55                  60

Leu Arg Ser Glu Glu Glu Gly Asp Ile Val Ala Leu Lys Asn Tyr Met
65                  70                  75                  80

Asn Ala Gln Tyr Phe Gly Glu Ile Gly Val Gly Thr Pro Pro Gln Lys
                85                  90                  95

Phe Thr Val Ile Phe Asp Thr Gly Ser Ser Asn Leu Trp Val Pro Ser
            100                 105                 110

Ala Lys Cys Tyr Phe Ser Ile Ala Cys Tyr Leu His Ser Arg Tyr Lys
        115                 120                 125

Ala Gly Ala Ser Ser Thr Tyr Lys Lys Asn Gly Lys Pro Ala Ala Ile
    130                 135                 140

Gln Tyr Gly Thr Gly Ser Ile Ala Gly Tyr Phe Ser Glu Asp Ser Val
145                 150                 155                 160

Thr Val Gly Asp Leu Val Val Lys Asp Gln Glu Phe Ile Glu Ala Thr
                165                 170                 175

Lys Glu Pro Gly Ile Thr Phe Leu Val Ala Lys Phe Asp Gly Ile Leu
            180                 185                 190

```
Gly Leu Gly Phe Lys Glu Ile Ser Val Gly Lys Ala Val Pro Val Trp
            195                 200                 205

Tyr Lys Met Ile Glu Gln Gly Leu Val Ser Asp Pro Val Phe Ser Phe
210                 215                 220

Trp Leu Asn Arg His Val Asp Glu Gly Glu Gly Glu Ile Ile Phe
225                 230                 235                 240

Gly Gly Met Asp Pro Lys His Tyr Val Gly Glu His Thr Tyr Val Pro
                245                 250                 255

Val Thr Gln Lys Gly Tyr Trp Gln Phe Asp Met Gly Asp Val Leu Val
            260                 265                 270

Gly Gly Lys Ser Thr Gly Phe Cys Ala Gly Cys Ala Ala Ile Ala
        275                 280                 285

Asp Ser Gly Thr Ser Leu Leu Ala Gly Pro Thr Ala Ile Ile Thr Glu
290                 295                 300

Ile Asn Glu Lys Ile Gly Ala Ala Gly Val Val Ser Gln Glu Cys Lys
305                 310                 315                 320

Thr Ile Val Ser Gln Tyr Gly Gln Gln Ile Leu Asp Leu Leu Ala
                325                 330                 335

Glu Thr Gln Pro Lys Lys Ile Cys Ser Gln Val Gly Leu Cys Thr Phe
            340                 345                 350

Asp Gly Thr Arg Gly Val Ser Ala Gly Ile Arg Ser Val Val Asp Asp
355                 360                 365

Glu Pro Val Lys Ser Asn Gly Leu Arg Ala Asp Pro Met Cys Ser Ala
            370                 375                 380

Cys Glu Met Ala Val Val Trp Met Gln Asn Gln Leu Ala Gln Asn Lys
385                 390                 395                 400

Thr Gln Asp Leu Ile Leu Asp Tyr Val Asn Gln Leu Cys Asn Arg Leu
                405                 410                 415

Pro Ser Pro Met Gly Glu Ser Ala Val Asp Cys Gly Ser Leu Gly Ser
            420                 425                 430

Met Pro Asp Ile Glu Phe Thr Ile Gly Gly Lys Lys Phe Ala Leu Lys
            435                 440                 445

Pro Glu Glu Tyr Ile Leu Lys Val Gly Glu Gly Ala Ala Ala Gln Cys
450                 455                 460

Ile Ser Gly Phe Thr Ala Met Asp Ile Pro Pro Arg Gly Pro Leu
465                 470                 475                 480

Trp Ile Leu Gly Asp Val Phe Met Gly Pro Tyr His Thr Val Phe Asp
                485                 490                 495

Tyr Gly Lys Leu Arg Ile Gly Phe Ala Lys Ala Ala
            500                 505

<210> SEQ ID NO 37
<211> LENGTH: 437
<212> TYPE: PRT
<213> ORGANISM: Nepenthes mirabilis
<220> FEATURE:
<221> NAME/KEY: PEPTIDE
<222> LOCATION: (1)..(437)
<223> OTHER INFORMATION: NmNEP-1 aspartic endoprotease

<400> SEQUENCE: 37

Met Ala Ser Ser Leu Tyr Ser Phe Leu Leu Ala Leu Ser Ile Val Tyr
1               5                   10                  15

Ile Phe Val Ala Pro Thr His Ser Thr Ser Arg Thr Ala Leu Asn His
            20                  25                  30

His His Glu Pro Lys Val Ala Gly Phe Gln Ile Met Leu Glu His Val
```

```
                    35                  40                  45
Asp Ser Gly Lys Asn Leu Thr Lys Phe Glu Leu Leu Glu Arg Ala Val
 50                  55                  60

Glu Arg Gly Ser Arg Arg Leu Gln Arg Leu Glu Ala Met Leu Asn Gly
 65                  70                  75                  80

Pro Ser Gly Val Glu Thr Pro Val Tyr Ala Gly Asp Gly Glu Tyr Leu
                     85                  90                  95

Met Asn Leu Ser Ile Gly Thr Pro Ala Gln Pro Phe Ser Ala Ile Met
                    100                 105                 110

Asp Thr Gly Ser Asp Leu Ile Trp Thr Gln Cys Gln Pro Cys Thr Gln
                115                 120                 125

Cys Phe Asn Gln Ser Thr Pro Ile Phe Asn Pro Gln Gly Ser Ser Ser
            130                 135                 140

Phe Ser Thr Leu Pro Cys Ser Ser Gln Leu Cys Gln Ala Leu Gln Ser
145                 150                 155                 160

Pro Thr Cys Ser Asn Asn Ser Cys Gln Tyr Thr Tyr Gly Tyr Gly Asp
                    165                 170                 175

Gly Ser Glu Thr Gln Gly Ser Met Gly Thr Glu Thr Leu Thr Phe Gly
                180                 185                 190

Ser Val Ser Ile Pro Asn Ile Thr Phe Gly Cys Gly Glu Asn Asn Gln
            195                 200                 205

Gly Phe Gly Gln Gly Asn Gly Ala Gly Leu Val Gly Met Gly Arg Gly
210                 215                 220

Pro Leu Ser Leu Pro Ser Gln Leu Asp Val Thr Lys Phe Ser Tyr Cys
225                 230                 235                 240

Met Thr Pro Ile Gly Ser Ser Thr Ser Ser Thr Leu Leu Gly Ser
                    245                 250                 255

Leu Ala Asn Ser Val Thr Ala Gly Ser Pro Asn Thr Thr Leu Ile Glu
                260                 265                 270

Ser Ser Gln Ile Pro Thr Phe Tyr Tyr Ile Thr Leu Asn Gly Leu Ser
            275                 280                 285

Val Gly Ser Thr Pro Leu Pro Ile Asp Pro Ser Val Phe Lys Leu Asn
290                 295                 300

Ser Asn Asn Gly Thr Gly Gly Ile Ile Ile Asp Ser Gly Thr Thr Leu
305                 310                 315                 320

Thr Tyr Phe Ala Asp Asn Ala Tyr Gln Ala Val Arg Gln Ala Phe Ile
                    325                 330                 335

Ser Gln Met Asn Leu Ser Val Val Asn Gly Ser Ser Ser Gly Phe Asp
                340                 345                 350

Leu Cys Phe Gln Met Pro Ser Asp Gln Ser Asn Leu Gln Ile Pro Thr
            355                 360                 365

Phe Val Met His Phe Asp Gly Gly Asp Leu Val Leu Pro Ser Glu Asn
370                 375                 380

Tyr Phe Ile Ser Pro Ser Asn Gly Leu Ile Cys Leu Ala Met Gly Ser
385                 390                 395                 400

Ser Ser Gln Gly Met Ser Ile Phe Gly Asn Ile Gln Gln Asn Leu
                    405                 410                 415

Leu Val Val Tyr Asp Thr Gly Asn Ser Val Val Ser Phe Leu Phe Ala
                420                 425                 430

Gln Cys Gly Ala Ser
            435

<210> SEQ ID NO 38
```

-continued

```
<211> LENGTH: 456
<212> TYPE: PRT
<213> ORGANISM: Hordeum vulgare
<220> FEATURE:
<221> NAME/KEY: PEPTIDE
<222> LOCATION: (1)..(456)
<223> OTHER INFORMATION: Hv aspartic endoprotease

<400> SEQUENCE: 38

Met Ala Gly Ser His Arg Glu Gly Ser Lys Asp Arg Ser Gly Arg Lys
1               5                   10                  15

Leu Leu Leu Val Leu Leu Cys Gly Tyr Tyr Ser Gly Val Ala Phe Ala
            20                  25                  30

Ala Asp Asp Ala Arg Thr Tyr Lys Val Leu Ala Val Gly Ser Leu Lys
        35                  40                  45

Ala Glu Val Val Cys Ser Val Thr Pro Ala Ser Ser Gly Thr Thr
    50                  55                  60

Val Pro Leu Asn His Arg Tyr Gly Pro Cys Ser Pro Ala Pro Ser Ala
65                  70                  75                  80

Lys Val Pro Thr Ile Leu Glu Leu Leu Glu His Asp Gln Leu Arg Ala
                85                  90                  95

Lys Tyr Ile Gln Arg Lys Leu Ser Gly Thr Asp Gly Leu Gln Pro Leu
            100                 105                 110

Asp Leu Thr Val Pro Thr Thr Leu Gly Ser Ala Leu Asp Thr Met Glu
        115                 120                 125

Tyr Val Ile Thr Val Gly Ile Gly Ser Pro Ala Val Thr Gln Thr Met
    130                 135                 140

Met Ile Asp Thr Gly Ser Asp Val Ser Trp Val Arg Cys Asn Ser Thr
145                 150                 155                 160

Asp Gly Leu Thr Leu Phe Asp Pro Ser Lys Ser Thr Thr Tyr Ala Pro
                165                 170                 175

Phe Ser Cys Ser Ser Ala Ala Cys Ala Gln Leu Gly Asn Asn Gly Asp
            180                 185                 190

Gly Cys Ser Asn Ser Gly Cys Gln Tyr Arg Val Gln Tyr Gly Asp Gly
        195                 200                 205

Ser Asn Thr Thr Gly Thr Tyr Ser Ser Asp Thr Leu Ala Leu Ser Ala
    210                 215                 220

Ser Asp Thr Val Thr Asp Phe His Phe Gly Cys Ser His His Glu Glu
225                 230                 235                 240

Asp Phe Asp Gly Glu Lys Ile Asp Gly Leu Met Gly Leu Gly Gly Asp
                245                 250                 255

Ala Gln Ser Leu Val Ser Gln Thr Ala Ala Thr Tyr Gly Lys Ser Phe
            260                 265                 270

Ser Tyr Cys Leu Pro Pro Thr Asn Arg Thr Ser Gly Phe Leu Thr Phe
        275                 280                 285

Gly Ala Pro Asn Gly Thr Ser Gly Gly Phe Val Thr Thr Pro Met Leu
    290                 295                 300

Arg Trp Pro Lys Ala Pro Thr Leu Tyr Gly Val Leu Leu Gln Asp Ile
305                 310                 315                 320

Ser Val Gly Gly Thr Pro Leu Gly Ile Gln Pro Ser Val Leu Ser Asn
                325                 330                 335

Gly Ser Val Met Asp Ser Gly Thr Val Ile Thr Trp Leu Pro Arg Arg
            340                 345                 350

Ala Tyr Ser Ala Leu Ser Ser Ala Phe Arg Ser Ser Met Thr Arg Leu
        355                 360                 365
```

```
Arg His Gln Arg Ala Ala Pro Leu Gly Ile Leu Asp Thr Cys Tyr Asp
    370                 375                 380

Phe Thr Gly Leu Val Asn Val Ser Ile Pro Ala Val Ser Leu Val Leu
385                 390                 395                 400

Asp Gly Gly Ala Val Val Asp Leu Asp Gly Asn Gly Ile Met Ile Gln
                405                 410                 415

Asp Cys Leu Ala Phe Ala Ala Thr Ser Gly Asp Ser Ile Ile Gly Asn
                    420                 425                 430

Val Gln Gln Arg Thr Phe Glu Val Leu His Asp Val Gly Gln Gly Val
            435                 440                 445

Phe Gly Phe Arg Ser Gly Ala Cys
    450                 455

<210> SEQ ID NO 39
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(6)
<223> OTHER INFORMATION: SEKDEL tag

<400> SEQUENCE: 39

Ser Glu Lys Asp Glu Leu
1               5

<210> SEQ ID NO 40
<211> LENGTH: 2500
<212> TYPE: DNA
<213> ORGANISM: Hordeum vulgare
<220> FEATURE:
<221> NAME/KEY: promoter
<222> LOCATION: (1)..(2500)
<223> OTHER INFORMATION: Hordeum vulgare promoter for HvNEP1 gene

<400> SEQUENCE: 40
ctacagcatc atatgtagtg aagtcgggtg tgctttcctc gatgctagat tgtgagaact      60
cagtggcatg ttctttagag gaagtgtgaa tgctttcttc catccttgat tgtgagaaat     120
cagtggcatc ttttgatact ggcacaagtt gtagaggact agagacacac tgctgctgat     180
tttatctgaa gcaacagctc cagcatcact gactgtatct tttgatagcg cttgtagatg     240
aatcggttca agtattacca taatctacgt tgcgcaaagc tgtgggcctg ccaggggcat     300
cttgatcttt caatacgctg accacctcta caggcataag tacagtacca tctgcattac     360
tgaaagtcag agctactgtg tcttcattgc tctctagctt tgtctgatgt tgcaaatttt     420
gtgacaactt ctctctagct tccaaaatct gtgccaagta aaaaaaagga tataagaaat     480
tcaccaccaa aaaaaggtaa taccaccaac ttctctattg tgcaaccatt aacattttaa     540
gcattgacct cagtcaataa atttatttat caagcaagaa tatgaacact aaaatatctt     600
aaactactac tcattccgtc ccaaaataag tgtcttgagc ttagtacaac tttatactag     660
agctagtata tagttcagac acttatttg agacggagga agtattacac attagtttga     720
aaatcagcac ttttagttt cattgtgaaa agacaatgtt ccaatatttg tacagcccgt     780
ttagtaattt agtatgctag caaaaatttc caaatgggta aatttagaag ccaaaccaag     840
tgttggcatc gcaaagtttg tggctagtca agttttggca tcgcaaatgt tggtagcaaa     900
caaagaagac tcgtagtgac acaaccctca ctgtcatgca catcaacatg atgttcaata     960
```

```
acatctacat caaagtcttc tccatgatat atccaacaag tatatgtact ttccatgcca    1020
tactcaatat gtgcgtgttc gcaacggtct gatgcttgta catatgatta agatgttttt    1080
cttttacatg atcagagcat ttaatcatcc tcgttgattt tctcttgaat gaagttcata    1140
aattctttga cacattagat gtagatataa ttaaaattcg ttcattaatt tggaaaagtt    1200
tgcgaatttt aaataattac atggcacacg ggataaccag aagaaaacac ggcgagacca    1260
aataaaagtt tacacgaatc ttggagtgat taatcgtgtg gtacatgact agatgtgca    1320 atacttaaat ctcatctaga tgtagctttg gaaaaggaat acactatcta tcggtctttt    1380
tttataaagg acgtttttat taactcataa cataggatca aaaggataca ataatgaca    1440 gggttacgac ccgtgggaac gacaaaacga aggaaacccc actccaaaac gtttgagggt    1500
gggctgcccc ctgggccagc tggcggcagg cggcccgtct tgccgtcatg ctgctggccg    1560
gcccgtccag ctggccccga cagcagccgg tgggtcagcg cccgtcccat ccgcatttgg    1620
aaaaattgtt agtgtaccta aaagtgatc acgaatttt aaagaattca cgcatttgaa    1680
aaacattcac aaaataaaaa aagttcatga tcctgaataa aaagttcata gatttgaaaa    1740
gaatttgcga atttgaaaaa agttcatgaa tttgaaaaca gttcgtgaat atgaaaaaca    1800
tttacacatt ttaaaaaggt tcatgaactt gaataaaaag gtcaaggatt tgaaaaaagt    1860
ttgcgcattt gaaaaatatt catgatttaa aaaaaacgtt catgcatttg aaaaacattc    1920
tcgaattcga aaaaaaatca ggaacatgaa tgaaaagttc acggaataga aaaatgtttg    1980
cacatttaaa aatgctcatg aatttggaaa aaagtcacag atatgaaaaa tgttcgtgaa    2040
tttgaaaaaa attcatgaac ttgaatgaaa agtttacaga actgaaaaac gtccatgaat    2100 tcgaaaagt tcgcaaattt ttgaaaagta gaggacacgc gggacaacaa aaaaacacac    2160
tgcaaacgat taatcgcgta gtacatgact taaatgtgta atacttaaat ctcatgtaga    2220
tgtatcttag caaaaggaat gcaatactat atattgtcta cacatcctta agctgttata    2280
gtgacatcaa atatgatcta gacatcctta agcacatctt taagctgatg tactaggtca    2340
aatagtgcca tggtgatcac tgccatatct ccaattcgag cttcagtagc ccaaagatat    2400
gcaaattaag tcagatcaga gtggtggtag atgtgctata taaacgtgat gagtatattc    2460
ctccatccaa ggccacatcc cacacataat tagcacatca                          2500

<210> SEQ ID NO 41
<211> LENGTH: 787
<212> TYPE: DNA
<213> ORGANISM: Hordeum vulgare
<220> FEATURE:
<221> NAME/KEY: promoter
<222> LOCATION: (1)..(787)
<223> OTHER INFORMATION: Hordeum vulgare promoter for HvLTP1 gene

<400> SEQUENCE: 41
gagctccaag gcatcaccaa gcttctatga cgccaaaaca tccaagaaag atatgtacta      60
ggataccaag cacccaagag taaacggagg aagtataata taaggccctg tttgataaca     120
aagtagtaaa aaaactaaag tattaaaaac tgcagtaatt ttacgtgtag atagaaaata     180
ccatggtttt aatataataa tatttttgc agtattcaca atgtagagaa actgtttgat     240
tacgccacat attactgcag tttagatcga gcaagtacac gggaagaaga taacgacgtc     300
ccaccccttc ttttcgcctt ctctgttttt taaaagagg tctggggtta gttttttcaa     360
tactgcagtt ttaaaatcac aattcttaga ggcaaccaaa cacctcattg taaataaaac     420
tatgataatc tccaaaactg cagtattcta aaaatactac aaaaattctt tgttatcaaa     480
```

| cagggcctaa ggagttaaaa aaatttagcc gtaactgaga ctcggcgagg caccagcagc | 540 |
| tagcagtcat caacacttga tggttggcaa aggcgagtcg acgtgtcgcg gggctcggcc | 600 |
| tgagcgggag atacaatctg ttctccagta accccgtcga tttggcccgc cgactaaagc | 660 |
| atccaggcat ctctcgctcg aaccccctatt taagcccctc cattcctccc aacattctcc | 720 |
| acacctccac gagttgctca tcactagcta gtacgttgta ctgttagcta cagattaaga | 780 |
| agtgatc | 787 |

<210> SEQ ID NO 42
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(4)
<223> OTHER INFORMATION: KDEL tag peptide

<400> SEQUENCE: 42

Lys Asp Glu Leu
1

<210> SEQ ID NO 43
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: PEPTIDE
<222> LOCATION: (1)..(4)
<223> OTHER INFORMATION: HDEL-tag peptide

<400> SEQUENCE: 43

His Asp Glu Leu
1

<210> SEQ ID NO 44
<211> LENGTH: 1898
<212> TYPE: DNA
<213> ORGANISM: Zea mays
<220> FEATURE:
<221> NAME/KEY: CDS
<222> LOCATION: (422)..(1783)
<223> OTHER INFORMATION: ZmNEP-1 gene encoding ZmNEP-1 having protein
      ID: XP_008668084.1

<400> SEQUENCE: 44

| cttttttatt tctccatctc catgctccga tgccgctgat gatcttgcca acagaggtgg | 60 |
| aaaattgcag tcaatggata cctgcacggc ggttctattc tgtagaacgt tcttctgatt | 120 |
| atgctgctgc tgcttgctca aaaaagtgcc taacaattat ccaacaacga ccccagccag | 180 |
| gcccacgttg aatttagtag aagcatgttt gaacccttat tgcccgcacg ccgaacaaag | 240 |
| aggtcaccta accacttaaa aattcagcgc ccatacaacc gtaggcgcca tcttcttggc | 300 |
| gtgagcgcga caacaatgct agcgagcgct gcagactgtt tcatctcttc caggcaactc | 360 |
| accagctgag actgagaccg gcacaagatg gcggctctga ccagccagcc accatagctc | 420 |

```
c atg tcg tcg tcg acc tca caa atg gcg tcg ctc gcc gtg ctc gtc ttc    469
  Met Ser Ser Ser Thr Ser Gln Met Ala Ser Leu Ala Val Leu Val Phe
  1               5                  10                 15 ctg gtg gtc tgc gca acg ctt gcg tcc ggt gcc gcc agc gtc cgc gtt    517
```

-continued

```
                Leu Val Val Cys Ala Thr Leu Ala Ser Gly Ala Ala Ser Val Arg Val
                             20                  25                  30 ggg ctc acg cgc atc cac tcc gac ccg gac acc acc gcg ccc cag ttc         565
Gly Leu Thr Arg Ile His Ser Asp Pro Asp Thr Thr Ala Pro Gln Phe
            35                  40                  45 gtg cgc gac gcg ctg cgc cgc gac atg cac cgg cag cgg tcc cga tcg         613
Val Arg Asp Ala Leu Arg Arg Asp Met His Arg Gln Arg Ser Arg Ser
 50                  55                  60 ttc ggc cgc gac cgc gac cgc gag ctc gcg gag tcc gac ggg cgc acc         661
Phe Gly Arg Asp Arg Asp Arg Glu Leu Ala Glu Ser Asp Gly Arg Thr
 65                  70                  75                  80 acg gtg tcc gcg cgc acc cgc aag gac ctg ccc aac ggc ggg gag tac         709
Thr Val Ser Ala Arg Thr Arg Lys Asp Leu Pro Asn Gly Gly Glu Tyr
                 85                  90                  95 ctc atg acg ctg gcc atc ggc acg ccg ccg ctg ccg tac gcg gcc gtc         757
Leu Met Thr Leu Ala Ile Gly Thr Pro Pro Leu Pro Tyr Ala Ala Val
            100                 105                 110 gcc gac acg ggc agc gac ctc atc tgg acg cag tgc gcg ccc tgc ggc         805
Ala Asp Thr Gly Ser Asp Leu Ile Trp Thr Gln Cys Ala Pro Cys Gly
        115                 120                 125 acc cag tgc ttc gag cag ccg gcg ccg ctg tac aac cca gcg agc tcg         853
Thr Gln Cys Phe Glu Gln Pro Ala Pro Leu Tyr Asn Pro Ala Ser Ser
    130                 135                 140 acc acg ttc agc gtg ctc ccg tgc aac agc tcc ctg agc atg tgc gcg         901
Thr Thr Phe Ser Val Leu Pro Cys Asn Ser Ser Leu Ser Met Cys Ala
145                 150                 155                 160 ggg gcg ctg gcg ggg gcc gcg ccg ccc ggg tgc gcc tgc atg tac              949
Gly Ala Leu Ala Gly Ala Ala Pro Pro Gly Cys Ala Cys Met Tyr
                165                 170                 175 aac cag acg tac ggc acc ggg tgg acg gcg ggc gtg cag ggc tcc gag         997
Asn Gln Thr Tyr Gly Thr Gly Trp Thr Ala Gly Val Gln Gly Ser Glu
            180                 185                 190 acc ttc acc ttc ggc tcg tcc gcc gcc gac cag gcc cgc gtc ccc ggc        1045
Thr Phe Thr Phe Gly Ser Ser Ala Ala Asp Gln Ala Arg Val Pro Gly
        195                 200                 205 gtc gcc ttc ggc tgc agc aac gcc agc agc agc gac tgg aac ggc tcg        1093
Val Ala Phe Gly Cys Ser Asn Ala Ser Ser Ser Asp Trp Asn Gly Ser
    210                 215                 220 gcg ggg ctg gtg ggg ctg ggc agg ggc agc ctg tcg ctc gtc tcg cag        1141
Ala Gly Leu Val Gly Leu Gly Arg Gly Ser Leu Ser Leu Val Ser Gln
225                 230                 235                 240 ctc ggc gcc ggc agg ttc tcc tac tgc ctg acg ccg ttc cag gac acc        1189
Leu Gly Ala Gly Arg Phe Ser Tyr Cys Leu Thr Pro Phe Gln Asp Thr
                245                 250                 255 aac agc acc agc acc ctc ctc ctc ggc ccg tcg gcg gcg ctc aac ggc        1237
Asn Ser Thr Ser Thr Leu Leu Leu Gly Pro Ser Ala Ala Leu Asn Gly
            260                 265                 270 acc ggc gtc cgc tcc acg ccg ttc gtc gct agc ccg gcc agg gcg ccc        1285
Thr Gly Val Arg Ser Thr Pro Phe Val Ala Ser Pro Ala Arg Ala Pro
        275                 280                 285 atg agc acc tac tac tac ctc aac ctg acg ggc ata tcc ctg ggc gcg        1333
Met Ser Thr Tyr Tyr Tyr Leu Asn Leu Thr Gly Ile Ser Leu Gly Ala
    290                 295                 300 aag gcg ctg ccc atc tct ccc ggc gca ttc tcc ctc aag ccc gac ggc        1381
Lys Ala Leu Pro Ile Ser Pro Gly Ala Phe Ser Leu Lys Pro Asp Gly
305                 310                 315                 320 acg ggc ggc ctc atc atc gac tcc ggc acg acc atc acc tcg ctg gcc        1429
Thr Gly Gly Leu Ile Ile Asp Ser Gly Thr Thr Ile Thr Ser Leu Ala
                325                 330                 335
```

-continued

```
aac gcg gcg tac cag cag gtc cgc gcc gcg gta aag tcc ctg gtc acg    1477
Asn Ala Ala Tyr Gln Gln Val Arg Ala Ala Val Lys Ser Leu Val Thr
            340                 345                 350 acg ctg cca acg gtc gac ggg tcg gac tcc acg ggg ctc gac ctg tgc    1525
Thr Leu Pro Thr Val Asp Gly Ser Asp Ser Thr Gly Leu Asp Leu Cys
    355                 360                 365 ttc gcg ctg ccg gcc ccg acg tcg gcg ccg ccg gcc gtg ctg ccg agc    1573
Phe Ala Leu Pro Ala Pro Thr Ser Ala Pro Pro Ala Val Leu Pro Ser
370                 375                 380 atg acg ctc cac ttc gac ggc gcc gac atg gtg ctc ccc gcg gac agc    1621
Met Thr Leu His Phe Asp Gly Ala Asp Met Val Leu Pro Ala Asp Ser
385                 390                 395                 400 tac atg atc tcg ggg tcc ggc gtg tgg tgc ctg gcc atg cgg aac cag    1669
Tyr Met Ile Ser Gly Ser Gly Val Trp Cys Leu Ala Met Arg Asn Gln
            405                 410                 415 acg gac ggc gcg atg agc acg ttc ggg aac tac cag cag cag aac atg    1717
Thr Asp Gly Ala Met Ser Thr Phe Gly Asn Tyr Gln Gln Gln Asn Met
        420                 425                 430 cac atc ctc tac gac gtc cgg gag gag acg ctg tcg ttc gct ccg gcc    1765
His Ile Leu Tyr Asp Val Arg Glu Glu Thr Leu Ser Phe Ala Pro Ala
    435                 440                 445 aag tgc agc act ctt tga cgatgcgata gttgtacata tgtatatgtg           1813
Lys Cys Ser Thr Leu
    450 tgcatatata ggattcatga ttttttttgt atacagtgga ttgttaaccg aacacactaa  1873 ttaattccat tattgttgac tgcta                                        1898

<210> SEQ ID NO 45
<211> LENGTH: 453
<212> TYPE: PRT
<213> ORGANISM: Zea mays

<400> SEQUENCE: 45

Met Ser Ser Ser Ser Gln Met Ala Ser Leu Ala Val Leu Val Phe
1               5                   10                  15

Leu Val Val Cys Ala Thr Leu Ala Ser Gly Ala Ala Ser Val Arg Val
            20                  25                  30

Gly Leu Thr Arg Ile His Ser Asp Pro Asp Thr Thr Ala Pro Gln Phe
        35                  40                  45

Val Arg Asp Ala Leu Arg Arg Asp Met His Arg Gln Arg Ser Arg Ser
    50                  55                  60

Phe Gly Arg Asp Arg Asp Arg Glu Leu Ala Glu Ser Asp Gly Arg Thr
65                  70                  75                  80

Thr Val Ser Ala Arg Thr Arg Lys Asp Leu Pro Asn Gly Gly Glu Tyr
            85                  90                  95

Leu Met Thr Leu Ala Ile Gly Thr Pro Pro Leu Pro Tyr Ala Ala Val
            100                 105                 110

Ala Asp Thr Gly Ser Asp Leu Ile Trp Thr Gln Cys Ala Pro Cys Gly
        115                 120                 125

Thr Gln Cys Phe Glu Gln Pro Ala Pro Leu Tyr Asn Pro Ala Ser Ser
    130                 135                 140

Thr Thr Phe Ser Val Leu Pro Cys Asn Ser Ser Leu Ser Met Cys Ala
145                 150                 155                 160

Gly Ala Leu Ala Gly Ala Ala Pro Pro Gly Cys Ala Cys Met Tyr
            165                 170                 175

Asn Gln Thr Tyr Gly Thr Gly Trp Thr Ala Gly Val Gln Gly Ser Glu
        180                 185                 190
```

```
Thr Phe Thr Phe Gly Ser Ser Ala Ala Asp Gln Ala Arg Val Pro Gly
        195                 200                 205

Val Ala Phe Gly Cys Ser Asn Ala Ser Ser Ser Asp Trp Asn Gly Ser
    210                 215                 220

Ala Gly Leu Val Gly Leu Gly Arg Gly Ser Leu Ser Leu Val Ser Gln
225                 230                 235                 240

Leu Gly Ala Gly Arg Phe Ser Tyr Cys Leu Thr Pro Phe Gln Asp Thr
                245                 250                 255

Asn Ser Thr Ser Thr Leu Leu Leu Gly Pro Ser Ala Ala Leu Asn Gly
            260                 265                 270

Thr Gly Val Arg Ser Thr Pro Phe Val Ala Ser Pro Ala Arg Ala Pro
        275                 280                 285

Met Ser Thr Tyr Tyr Leu Asn Leu Thr Gly Ile Ser Leu Gly Ala
    290                 295                 300

Lys Ala Leu Pro Ile Ser Pro Gly Ala Phe Ser Leu Lys Pro Asp Gly
305                 310                 315                 320

Thr Gly Gly Leu Ile Ile Asp Ser Gly Thr Thr Ile Thr Ser Leu Ala
                325                 330                 335

Asn Ala Ala Tyr Gln Gln Val Arg Ala Ala Val Lys Ser Leu Val Thr
            340                 345                 350

Thr Leu Pro Thr Val Asp Gly Ser Asp Ser Thr Gly Leu Asp Leu Cys
        355                 360                 365

Phe Ala Leu Pro Ala Pro Thr Ser Ala Pro Pro Ala Val Leu Pro Ser
    370                 375                 380

Met Thr Leu His Phe Asp Gly Ala Asp Met Val Leu Pro Ala Asp Ser
385                 390                 395                 400

Tyr Met Ile Ser Gly Ser Gly Val Trp Cys Leu Ala Met Arg Asn Gln
                405                 410                 415

Thr Asp Gly Ala Met Ser Thr Phe Gly Asn Tyr Gln Gln Gln Asn Met
            420                 425                 430

His Ile Leu Tyr Asp Val Arg Glu Glu Thr Leu Ser Phe Ala Pro Ala
        435                 440                 445

Lys Cys Ser Thr Leu
    450

<210> SEQ ID NO 46
<211> LENGTH: 1943
<212> TYPE: DNA
<213> ORGANISM: Glycine max
<220> FEATURE:
<221> NAME/KEY: CDS
<222> LOCATION: (426)..(1787)
<223> OTHER INFORMATION: GmNEP-1 gene encoding GmNEP-1 with protein ID:
      XP_003523200.1

<400> SEQUENCE: 46
attgccttag atacgttttg caacaaataa taaatctttt accaacctca acgcaagact      60
cggtacttaa ttgttgcgac actacgctga taccttaacc tccattcatc atcaaacaca    120
cgacgtttct ctgttcacac caaaacaaaa cttctctctc tctgtctccc cttttgtttt    180
tttccttcaa agaaaaattt gacaagccaa aactccccct cttgcttctt cccttaatcc    240
tctccaccac attcgaaggg aacgttacaa aaaaatctcc attttttctc aagttaatca    300
agtaagataa gatcattccc ctctatcaac aaacctttat tcttatatat acattcccac    360
aattcccatc actcattcat tccactttat ataatttccc ctccactcca cattgtgcac    420
```

```
ccttc atg gtc atg gca aaa cta aaa cac cct tca tct ttt gtc aca ttg        470
      Met Val Met Ala Lys Leu Lys His Pro Ser Ser Phe Val Thr Leu
       1               5              10                 15 gtg gca ctt ctt cta gca gtg tct ctt ttc gtt gct cca aca tcc tca          518
Val Ala Leu Leu Leu Ala Val Ser Leu Phe Val Ala Pro Thr Ser Ser
             20                 25                 30 aca tcc aga aaa act att ctc aag cac cac cct tac cca aca aaa ggg          566
Thr Ser Arg Lys Thr Ile Leu Lys His His Pro Tyr Pro Thr Lys Gly
             35                 40                 45 ttc cga gtc atg ctt cgc cac gtt gat tcg ggt aaa aat tta acc aaa          614
Phe Arg Val Met Leu Arg His Val Asp Ser Gly Lys Asn Leu Thr Lys
             50                 55                 60 cta gag cgt gtc caa cac ggg atc aag cgt ggg aag agt agg ctt cag          662
Leu Glu Arg Val Gln His Gly Ile Lys Arg Gly Lys Ser Arg Leu Gln
 65              70                 75 agg ctt aat gca atg gtg ttg gca gca tca aca cta gat tct gaa gat          710
Arg Leu Asn Ala Met Val Leu Ala Ala Ser Thr Leu Asp Ser Glu Asp
 80              85                 90                 95 caa tta gaa gcc cct att cat gca ggg aat gga gaa tat tta atg gag          758
Gln Leu Glu Ala Pro Ile His Ala Gly Asn Gly Glu Tyr Leu Met Glu
                100                105                110 tta gcc att gga acc cca cca gtg tct tac cct gcg gtt ttg gac act          806
Leu Ala Ile Gly Thr Pro Pro Val Ser Tyr Pro Ala Val Leu Asp Thr
                115                120                125 ggc agt gac ctt att tgg aca cag tgc aag cct tgc acg cag tgt tat          854
Gly Ser Asp Leu Ile Trp Thr Gln Cys Lys Pro Cys Thr Gln Cys Tyr
            130                135                140 aaa caa cca aca ccc att ttt gat ccc aag aag tcc tct tct ttt tcc          902
Lys Gln Pro Thr Pro Ile Phe Asp Pro Lys Lys Ser Ser Ser Phe Ser
145                150                155 aag gtt tca tgt ggt agc agc ttg tgc agt gct gtg cct tct tca aca          950
Lys Val Ser Cys Gly Ser Ser Leu Cys Ser Ala Val Pro Ser Ser Thr
160                165                170                175 tgc agt gat ggg tgt gag tat gtt tat tca tac ggt gac tat tca atg         998
Cys Ser Asp Gly Cys Glu Tyr Val Tyr Ser Tyr Gly Asp Tyr Ser Met
                180                185                190 aca caa ggc gtt ttg gcc act gag act ttc act ttt ggg aag tct aag        1046
Thr Gln Gly Val Leu Ala Thr Glu Thr Phe Thr Phe Gly Lys Ser Lys
                195                200                205 aac aaa gtt tcg gtt cac aac att ggt ttt ggt tgt ggg gag gac aat        1094
Asn Lys Val Ser Val His Asn Ile Gly Phe Gly Cys Gly Glu Asp Asn
            210                215                220 gaa ggt gat gga ttt gaa caa gct tca ggg ttg gtt ggt ctt gga cgt        1142
Glu Gly Asp Gly Phe Glu Gln Ala Ser Gly Leu Val Gly Leu Gly Arg
225                230                235 ggt cct ttg tcc ttg gtt tct caa ctc aag gaa ccg aga ttt tct tat        1190
Gly Pro Leu Ser Leu Val Ser Gln Leu Lys Glu Pro Arg Phe Ser Tyr
240                245                250                255 tgt ttg acc cca atg gat gac aca aaa gaa agt att ttg ttg ttg ggg        1238
Cys Leu Thr Pro Met Asp Asp Thr Lys Glu Ser Ile Leu Leu Leu Gly
                260                265                270 tct ttg ggt aaa gtg aaa gat gca aaa gaa gtg gtg aca aca cct ctt        1286
Ser Leu Gly Lys Val Lys Asp Ala Lys Glu Val Val Thr Thr Pro Leu
            275                280                285 ctc aaa aac cct ttg caa cct tct ttt tac tat ctt tct ctt gaa ggc        1334
Leu Lys Asn Pro Leu Gln Pro Ser Phe Tyr Tyr Leu Ser Leu Glu Gly
            290                295                300 atc tct gtt ggg gac act cga ttg tcc att gag aag tcc act ttt gaa        1382
Ile Ser Val Gly Asp Thr Arg Leu Ser Ile Glu Lys Ser Thr Phe Glu
305                310                315
```

```
gtg ggg gat gat ggg aat ggt ggt gtg atc ata gac tct ggc acc aca    1430
Val Gly Asp Asp Gly Asn Gly Gly Val Ile Ile Asp Ser Gly Thr Thr
320             325                 330                 335 atc acc tac att gaa caa aag gcc ttt gag gca ctc aaa aaa gag ttc    1478
Ile Thr Tyr Ile Glu Gln Lys Ala Phe Glu Ala Leu Lys Lys Glu Phe
                340                 345                 350 att tct caa acc aaa ctt cct ttg gac aaa act agc tca aca ggg ttg    1526
Ile Ser Gln Thr Lys Leu Pro Leu Asp Lys Thr Ser Ser Thr Gly Leu
            355                 360                 365 gat ctt tgc ttc tct ctg cca tca ggg tca aca caa gtg gag att cca    1574
Asp Leu Cys Phe Ser Leu Pro Ser Gly Ser Thr Gln Val Glu Ile Pro
        370                 375                 380 aag att gtt ttc cat ttc aag ggt ggg gat ttg gag ctt cct gct gag    1622
Lys Ile Val Phe His Phe Lys Gly Gly Asp Leu Glu Leu Pro Ala Glu
    385                 390                 395 aac tac atg att ggt gac tcc aat ttg ggt gtg gct tgt tta gcc atg    1670
Asn Tyr Met Ile Gly Asp Ser Asn Leu Gly Val Ala Cys Leu Ala Met
400             405                 410                 415 ggt gct tct agt gga atg tct ata ttc gga aat gtt caa cag cag aac    1718
Gly Ala Ser Ser Gly Met Ser Ile Phe Gly Asn Val Gln Gln Gln Asn
                420                 425                 430 att ttg gtg aat cat gat ctt gaa aag gag acc att tct ttt gtt cct    1766
Ile Leu Val Asn His Asp Leu Glu Lys Glu Thr Ile Ser Phe Val Pro
            435                 440                 445 acg tcg tgt gat cag ctg tga gtgtgtgata ttcactatat gtttttattg       1817
Thr Ser Cys Asp Gln Leu
        450 ctttgtttgt ttgatgatgt tctgttgccg aactcgtatt gctatgattg aatctcttag  1877 ttgttgcaat aatatgaaca ttttattctc tgtccaattc aaatggatca gcacattaat  1937 agaaca                                                             1943

<210> SEQ ID NO 47
<211> LENGTH: 453
<212> TYPE: PRT
<213> ORGANISM: Glycine max

<400> SEQUENCE: 47

Met Val Met Ala Lys Leu Lys His Pro Ser Ser Phe Val Thr Leu Val
1               5                   10                  15

Ala Leu Leu Leu Ala Val Ser Leu Phe Val Ala Pro Thr Ser Ser Thr
                20                  25                  30

Ser Arg Lys Thr Ile Leu Lys His His Pro Tyr Pro Thr Lys Gly Phe
            35                  40                  45

Arg Val Met Leu Arg His Val Asp Ser Gly Lys Asn Leu Thr Lys Leu
        50                  55                  60

Glu Arg Val Gln His Gly Ile Lys Arg Gly Lys Ser Arg Leu Gln Arg
65                  70                  75                  80

Leu Asn Ala Met Val Leu Ala Ser Thr Leu Asp Ser Glu Asp Gln
                85                  90                  95

Leu Glu Ala Pro Ile His Ala Gly Asn Gly Glu Tyr Leu Met Glu Leu
            100                 105                 110

Ala Ile Gly Thr Pro Pro Val Ser Tyr Pro Ala Val Leu Asp Thr Gly
        115                 120                 125

Ser Asp Leu Ile Trp Thr Gln Cys Lys Pro Cys Thr Gln Cys Tyr Lys
    130                 135                 140

Gln Pro Thr Pro Ile Phe Asp Pro Lys Lys Ser Ser Ser Phe Ser Lys
```

```
                145                 150                 155                 160
Val Ser Cys Gly Ser Ser Leu Cys Ser Ala Val Pro Ser Ser Thr Cys
                    165                 170                 175

Ser Asp Gly Cys Glu Tyr Val Tyr Ser Tyr Gly Asp Tyr Ser Met Thr
                180                 185                 190

Gln Gly Val Leu Ala Thr Glu Thr Phe Thr Phe Gly Lys Ser Lys Asn
            195                 200                 205

Lys Val Ser Val His Asn Ile Gly Phe Gly Cys Gly Glu Asp Asn Glu
        210                 215                 220

Gly Asp Gly Phe Glu Gln Ala Ser Gly Leu Val Gly Leu Gly Arg Gly
225                 230                 235                 240

Pro Leu Ser Leu Val Ser Gln Leu Lys Glu Pro Arg Phe Ser Tyr Cys
                245                 250                 255

Leu Thr Pro Met Asp Asp Thr Lys Glu Ser Ile Leu Leu Leu Gly Ser
                260                 265                 270

Leu Gly Lys Val Lys Asp Ala Lys Glu Val Val Thr Thr Pro Leu Leu
            275                 280                 285

Lys Asn Pro Leu Gln Pro Ser Phe Tyr Tyr Leu Ser Leu Glu Gly Ile
        290                 295                 300

Ser Val Gly Asp Thr Arg Leu Ser Ile Glu Lys Ser Thr Phe Glu Val
305                 310                 315                 320

Gly Asp Asp Gly Asn Gly Gly Val Ile Ile Asp Ser Gly Thr Thr Ile
                325                 330                 335

Thr Tyr Ile Glu Gln Lys Ala Phe Glu Ala Leu Lys Lys Glu Phe Ile
                340                 345                 350

Ser Gln Thr Lys Leu Pro Leu Asp Lys Thr Ser Ser Thr Gly Leu Asp
            355                 360                 365

Leu Cys Phe Ser Leu Pro Ser Gly Ser Thr Gln Val Glu Ile Pro Lys
        370                 375                 380

Ile Val Phe His Phe Lys Gly Gly Asp Leu Glu Leu Pro Ala Glu Asn
385                 390                 395                 400

Tyr Met Ile Gly Asp Ser Asn Leu Gly Val Ala Cys Leu Ala Met Gly
                405                 410                 415

Ala Ser Ser Gly Met Ser Ile Phe Gly Asn Val Gln Gln Asn Ile
                420                 425                 430

Leu Val Asn His Asp Leu Glu Lys Glu Thr Ile Ser Phe Val Pro Thr
            435                 440                 445

Ser Cys Asp Gln Leu
        450

<210> SEQ ID NO 48
<211> LENGTH: 1383
<212> TYPE: DNA
<213> ORGANISM: Gossypium hirsutum
<220> FEATURE:
<221> NAME/KEY: CDS
<222> LOCATION: (1)..(1383)
<223> OTHER INFORMATION: GhNEP-1 gene encoding GhNEP-1 with protein ID:
      XP_016704203.1

<400> SEQUENCE: 48 atg tct tta tcc ctt cgt ttt ctc agc gct aaa ctg ttc tta tgc ctc    48
Met Ser Leu Ser Leu Arg Phe Leu Ser Ala Lys Leu Phe Leu Cys Leu
1               5                   10                  15 tgt tta aca tta ttt caa cac cat gtc acg ttt tct gct tcg aat cct    96
Cys Leu Thr Leu Phe Gln His His Val Thr Phe Ser Ala Ser Asn Pro
            20                  25                  30
```

```
act ggt cta acc cta agg gct gtc ctg gat gat tct cca aac tct cct      144
Thr Gly Leu Thr Leu Arg Ala Val Leu Asp Asp Ser Pro Asn Ser Pro
        35                  40                  45 tta tac ctt att gaa aac atg act ata gct gaa aga atc gaa aga ttt      192
Leu Tyr Leu Ile Glu Asn Met Thr Ile Ala Glu Arg Ile Glu Arg Phe
50                  55                  60 atc caa gtt acc aat gct aaa gac aat tat ttg aat ctt aat gca agg      240
Ile Gln Val Thr Asn Ala Lys Asp Asn Tyr Leu Asn Leu Asn Ala Arg
65                  70                  75                  80 gta ggc cct gat aat tct aat tct cta tct cga gta gta atg gct cga      288
Val Gly Pro Asp Asn Ser Asn Ser Leu Ser Arg Val Val Met Ala Arg
                85                  90                  95 gat ggt tta ttt tat tca gta tgg ctt cta ata gga agc caa ggc caa      336
Asp Gly Leu Phe Tyr Ser Val Trp Leu Leu Ile Gly Ser Gln Gly Gln
            100                 105                 110 gaa gtg aag ctg ttg atg gac aca ggc ggt ggt cta aca tgg acg cag      384
Glu Val Lys Leu Leu Met Asp Thr Gly Gly Gly Leu Thr Trp Thr Gln
        115                 120                 125 tgt cag cct tgc cta aat tgt ttc cca cag aat ctt cca att tat gat      432
Cys Gln Pro Cys Leu Asn Cys Phe Pro Gln Asn Leu Pro Ile Tyr Asp
    130                 135                 140 tct aga act tcc act act tac tcc act ctt tct tgt gac cat cct ctc      480
Ser Arg Thr Ser Thr Thr Tyr Ser Thr Leu Ser Cys Asp His Pro Leu
145                 150                 155                 160 tgc caa gtc gag ggt agc ctt tat act tgt gtc gat gac tta tgt atc      528
Cys Gln Val Glu Gly Ser Leu Tyr Thr Cys Val Asp Asp Leu Cys Ile
                165                 170                 175 ttc gtt cat aat tat cat ggc ggc ctc tac act acg ggg gtc gca tcc      576
Phe Val His Asn Tyr His Gly Gly Leu Tyr Thr Thr Gly Val Ala Ser
            180                 185                 190 ctg gaa aca ttc tat ttc cct atg gac cca tct act gct cta act ttc      624
Leu Glu Thr Phe Tyr Phe Pro Met Asp Pro Ser Thr Ala Leu Thr Phe
        195                 200                 205 aat aat ctg gtc ttc ggt tgc tct cgg gat agt cgt aac gtt gtt ttt      672
Asn Asn Leu Val Phe Gly Cys Ser Arg Asp Ser Arg Asn Val Val Phe
    210                 215                 220 cag gac acc gaa ctt tca ggg atc ttt gga atg aac atg atg ccg gat      720
Gln Asp Thr Glu Leu Ser Gly Ile Phe Gly Met Asn Met Met Pro Asp
225                 230                 235                 240 tca ttg atg agt cag ctt tct agt ttt act aac ttt cga ttc tcc tac      768
Ser Leu Met Ser Gln Leu Ser Ser Phe Thr Asn Phe Arg Phe Ser Tyr
                245                 250                 255 tgt ttg gtc cca ttt cct gat tta ata cct cat aca ctt gtt cta agg      816
Cys Leu Val Pro Phe Pro Asp Leu Ile Pro His Thr Leu Val Leu Arg
            260                 265                 270 ttc gga gat gac att cca ctg ttg cct cca gaa cgt gtt aaa aca acg      864
Phe Gly Asp Asp Ile Pro Leu Leu Pro Pro Glu Arg Val Lys Thr Thr
        275                 280                 285 atg ttc gtg cac gca cct tac ctc tat aat tac tac gtg aac ctg gtg      912
Met Phe Val His Ala Pro Tyr Leu Tyr Asn Tyr Tyr Val Asn Leu Val
    290                 295                 300 aca atc agt ttt cta aat gat cgt cta gga ttt cct cca tct caa ttt      960
Thr Ile Ser Phe Leu Asn Asp Arg Leu Gly Phe Pro Pro Ser Gln Phe
305                 310                 315                 320 cag ctg agg gaa gac gga tta ggt ggt tgc ttc gtt gac tct gga tat     1008
Gln Leu Arg Glu Asp Gly Leu Gly Gly Cys Phe Val Asp Ser Gly Tyr
                325                 330                 335 ttg ctc acc gca atc gaa gac aac tat gtt gga ggg gtg aat gca tat     1056
Leu Leu Thr Ala Ile Glu Asp Asn Tyr Val Gly Gly Val Asn Ala Tyr
```

```
                    340                 345                 350
gat gta cta atg gat ctg ttt aca gct tat tat gag agc aac aat ctt    1104
Asp Val Leu Met Asp Leu Phe Thr Ala Tyr Tyr Glu Ser Asn Asn Leu
            355                 360                 365 aga aga aca acg gat ccg tca gga ctt gac atg tgt ttt gaa cgt cca    1152
Arg Arg Thr Thr Asp Pro Ser Gly Leu Asp Met Cys Phe Glu Arg Pro
370                 375                 380 aat gat ttt aat aat ttt gca aat cta aca ttc cat ttt gat ggt gaa    1200
Asn Asp Phe Asn Asn Phe Ala Asn Leu Thr Phe His Phe Asp Gly Glu
385                 390                 395                 400 gcc gat tac ttc gtt cct cca cag cat ttg cat atc ttc caa caa gat    1248
Ala Asp Tyr Phe Val Pro Pro Gln His Leu His Ile Phe Gln Gln Asp
            405                 410                 415 cac ttc tgc gta gca ata aca agg gga aga tac gca act gtg ctt gga    1296
His Phe Cys Val Ala Ile Thr Arg Gly Arg Tyr Ala Thr Val Leu Gly
            420                 425                 430 gca tgg cag caa caa aat aaa cgt atg ctt tat gat gta ggg ctt ggt    1344
Ala Trp Gln Gln Gln Asn Lys Arg Met Leu Tyr Asp Val Gly Leu Gly
            435                 440                 445 aga ctc caa ttt gct gat gaa aac tgt gcg aat gat taa                1383
Arg Leu Gln Phe Ala Asp Glu Asn Cys Ala Asn Asp
450                 455                 460

<210> SEQ ID NO 49
<211> LENGTH: 460
<212> TYPE: PRT
<213> ORGANISM: Gossypium hirsutum

<400> SEQUENCE: 49

Met Ser Leu Ser Leu Arg Phe Leu Ser Ala Lys Leu Phe Leu Cys Leu
1               5                   10                  15

Cys Leu Thr Leu Phe Gln His His Val Thr Phe Ser Ala Ser Asn Pro
                20                  25                  30

Thr Gly Leu Thr Leu Arg Ala Val Leu Asp Asp Ser Pro Asn Ser Pro
            35                  40                  45

Leu Tyr Leu Ile Glu Asn Met Thr Ile Ala Glu Arg Ile Glu Arg Phe
        50                  55                  60

Ile Gln Val Thr Asn Ala Lys Asp Asn Tyr Leu Asn Leu Asn Ala Arg
65                  70                  75                  80

Val Gly Pro Asp Asn Ser Asn Ser Leu Ser Arg Val Val Met Ala Arg
                85                  90                  95

Asp Gly Leu Phe Tyr Ser Val Trp Leu Leu Ile Gly Ser Gln Gly Gln
            100                 105                 110

Glu Val Lys Leu Leu Met Asp Thr Gly Gly Gly Leu Thr Trp Thr Gln
        115                 120                 125

Cys Gln Pro Cys Leu Asn Cys Phe Pro Gln Asn Leu Pro Ile Tyr Asp
130                 135                 140

Ser Arg Thr Ser Thr Thr Tyr Ser Thr Leu Ser Cys Asp His Pro Leu
145                 150                 155                 160

Cys Gln Val Glu Gly Ser Leu Tyr Thr Cys Val Asp Asp Leu Cys Ile
                165                 170                 175

Phe Val His Asn Tyr His Gly Gly Leu Tyr Thr Thr Gly Val Ala Ser
            180                 185                 190

Leu Glu Thr Phe Tyr Phe Pro Met Asp Pro Ser Thr Ala Leu Thr Phe
        195                 200                 205

Asn Asn Leu Val Phe Gly Cys Ser Arg Asp Ser Arg Asn Val Val Phe
210                 215                 220
```

Gln Asp Thr Glu Leu Ser Gly Ile Phe Gly Met Asn Met Met Pro Asp
225                 230                 235                 240

Ser Leu Met Ser Gln Leu Ser Ser Phe Thr Asn Phe Arg Phe Ser Tyr
            245                 250                 255

Cys Leu Val Pro Phe Pro Asp Leu Ile Pro His Thr Leu Val Leu Arg
        260                 265                 270

Phe Gly Asp Asp Ile Pro Leu Leu Pro Pro Glu Arg Val Lys Thr Thr
    275                 280                 285

Met Phe Val His Ala Pro Tyr Leu Tyr Asn Tyr Tyr Val Asn Leu Val
290                 295                 300

Thr Ile Ser Phe Leu Asn Asp Arg Leu Gly Phe Pro Pro Ser Gln Phe
305                 310                 315                 320

Gln Leu Arg Glu Asp Gly Leu Gly Gly Cys Phe Val Asp Ser Gly Tyr
            325                 330                 335

Leu Leu Thr Ala Ile Glu Asp Asn Tyr Val Gly Val Asn Ala Tyr
        340                 345                 350

Asp Val Leu Met Asp Leu Phe Thr Ala Tyr Tyr Glu Ser Asn Asn Leu
    355                 360                 365

Arg Arg Thr Thr Asp Pro Ser Gly Leu Asp Met Cys Phe Glu Arg Pro
370                 375                 380

Asn Asp Phe Asn Asn Phe Ala Asn Leu Thr Phe His Phe Asp Gly Glu
385                 390                 395                 400

Ala Asp Tyr Phe Val Pro Pro Gln His Leu His Ile Phe Gln Gln Asp
            405                 410                 415

His Phe Cys Val Ala Ile Thr Arg Gly Arg Tyr Ala Thr Val Leu Gly
        420                 425                 430

Ala Trp Gln Gln Gln Asn Lys Arg Met Leu Tyr Asp Val Gly Leu Gly
    435                 440                 445

Arg Leu Gln Phe Ala Asp Glu Asn Cys Ala Asn Asp
    450                 455                 460

<210> SEQ ID NO 50
<211> LENGTH: 251
<212> TYPE: DNA
<213> ORGANISM: Zea mays
<220> FEATURE:
<221> NAME/KEY: promoter
<222> LOCATION: (1)..(251)
<223> OTHER INFORMATION: a-Zein gene promoter

<400> SEQUENCE: 50
gcattacaaa gttagcttca caagcgtatg aattcattga caacccttga catgtaaagt      60
tgattcatat gtataagaaa gcttaatgat ctatctgtac atccaaatcc atgtactatg     120
tttccacgtc atgcaacgca acattccaaa accatggatc atctataaat ggctagctcc     180
cacatatgaa ctagtctcta tcatcatcca atccagatca gcaaagcggc agtgcgtaga     240
gaggatcgtc g                                                          251

<210> SEQ ID NO 51
<211> LENGTH: 2335
<212> TYPE: DNA
<213> ORGANISM: Oryza sativa
<220> FEATURE:
<221> NAME/KEY: promoter
<222> LOCATION: (1)..(2335)
<223> OTHER INFORMATION: glutelin GluB-1 promoter

<400> SEQUENCE: 51

-continued

```
acagattctt gctaccaaca acttcacaaa gtagtagtca accaaaacta tgctaaggaa      60
tcacctcact tccgcccatg accgtgagca cgactgttca aacagtttgt taatctctac     120
aaagaaggta cactttacct acacaacgcc actaacctga gttacccagc ccatgcaaaa     180
tagccacgtc ttgtgactta agggatttcg cgacaaggca tttcgaaagc ccacacaagg     240 acacctatg  aaaactggag gggtcccaca gaccaacaac aagttaggtc ccaaaccatg     300
ttgtgccagg aaaaatccaa ggggtcctcc ccaacaccac cccgacaaat ccacttgtcc     360
attggcatca agatttgcct gacctagcta attactcagc caggcatgtc acaattcacc     420
catgtggtca cacatgttag gttggagaaa ttctaaagga aaggaatcgg tccatatgag     480
caagaccgag aaaccatacc accagtactt ctaccgaaat acgagtttag taaactcatt     540
tgttttcaag gcacccgacc caggtgtgtc gggttttcca gggattttgt aaacccaagt     600
tttacccata gttgatcatt caaattttga ggagggtcat tggtatccgt acctgagggc     660
acgaatactg agacctagca ttgtagtcga ccaaggagga taatgcagca attgtaggtg     720
gggcctgttg gttatattgc aaactgcggc caacatttca tgtgtaattt agagatgtgc     780
attttgagaa atgaaatact tagttttcaaa ttatgggctc aaataatgaa aggtgaccta     840
ccttgcttga tatcttgagc ttcttcctcg tattccgcgc actaggagat cttctggctc     900
cgaagctaca cgtggaacga gataactcaa caaaacgacc aaggaaaagc tcgtattagt     960
gagtactaag tgtgccactg aatagatctc gattttgag  gaattttaga agttgaacag    1020
agtcaatcga acagacagtt gaagagatat ggattttcta agattaattg attctctgta    1080
taaagaaaaa aagtattatt gaattaaatg gaaaagaaa  aaggaaaaag gggatggctt    1140 ctgcttttg  ggctgaaggc ggcgtgtggc cagcgtgctg cgtgcggaca gcgagcgaac    1200
acacgacgga gcagctacga cgaacggggg accgagtgga ccggacgagg atgtggccta    1260
ggacgagtgc acaaggctag tggactcggt ccccgcgcgg tatcccgagt ggtccactgt    1320
ctgcaaacac gattcacata gagcgggcag acgcgggagc cgtcctaggt gcaccggaag    1380
caaatccgtc gcctgggtgg atttgagtga cacggcccac gtgtagcctc acagctctcc    1440
gtggtcagat gtgtaaaatt atcataatat gtgttttca aatagttaaa taatatatat     1500
aggcaagtta tatgggtcaa taagcagtaa aaaggcttat gacatggtaa aattacttac    1560
accaatatgc cttactgtct gatatatttt acatgacaac aaagttacaa gtacgtcatt    1620
taaaaataca agttacttat caattgtagt gtatcaagta aatgacaaca aacctacaaa    1680
tttgctattt tgaaggaaca cttaaaaaaa tcaataggca agttatatag tcaataaact    1740
gcaagaaggc ttatgacatg gaaaaattac atacaccaat atgctttatt gtccggtata    1800
ttttacaaga caacaaagtt ataagtatgt catttaaaaa tacaagttac ttatcaattg    1860
tcaagtaaat gaaacaaac  ctacaaattt gttattttga aggaacacct aaattatcaa    1920
atatagcttg ctacgcaaaa tgacaacatg cttacaagtt attatcatct taaagttaga    1980
ctcatcttct caagcataag agctttatgg tgcaaaaaca aatataatga caaggcaaag    2040
atacatacat attaagagta tggacagaca tttctttaac aaactccatt tgtattactc    2100
caaaagcacc agaagtttgt catggctgag tcatgaaatg tatagttcaa tcttgcaaag    2160
ttgcctttcc ttttgtactg tgttttaaca ctacaagcca tatattgtct gtacgtgcaa    2220
caaactatat caccatgtat cccaagatgc ttttttattg ctatataaac tagcttggtc    2280
tgtctttgaa ctcacatcaa ttagcttaag tttccataag caagtacaaa tagct         2335
```

<210> SEQ ID NO 52
<211> LENGTH: 1381
<212> TYPE: DNA
<213> ORGANISM: Glycine max
<220> FEATURE:
<221> NAME/KEY: promoter
<222> LOCATION: (1)..(1381)
<223> OTHER INFORMATION: G. max b-conglycinin promoter

<400> SEQUENCE: 52

| | | | | | |
|---|---|---|---|---|---|
| agtgcttgga | tttggaccag | acttgaattt | taatttaatg | atattataat | atgtgaatat | 60 |
| atttttgaga | caattgtaaa | tttcagataa | aaaaataatg | taattaaaat | tgtaataact | 120 |
| atatcgtata | cttaattaat | tattaaatgt | gacaaaaaag | atatacatca | aaacttaatg | 180 |
| tttcatgact | ttttttttaat | gtgtgtccta | aatagaaatt | aaaaataaaa | attattatat | 240 |
| ccaaatgaaa | aaaacattta | atacgtatta | tttaagaaat | aacaatatat | ttatatttta | 300 |
| atatgtattc | acatgtaaat | ttaaaaacaa | aaacaaaatt | tctcttttat | tgattaatta | 360 |
| aaataattt | ataactacat | ttattttcta | ttattatcaa | ttttcttctg | ttttttttatt | 420 |
| tggcatatat | acctagacaa | gtcaaaaaat | gactattctt | taataatcaa | tcattattct | 480 |
| tacatattgg | ttttcgaact | acgagttatg | aagtgttcca | attgcacctt | agtgtttttg | 540 |
| ataggccttc | cccatttgcc | gctcattaat | taatttgata | acagccgtac | cccgatcaaa | 600 |
| ttactttatg | cttcttccca | tcgtaaatta | tatgcatgtc | gggttctttt | aatcttggta | 660 |
| ctctcgaatt | ggccaccaca | accactgact | agtctcttgg | atcatgagaa | aaagccaaag | 720 |
| aacaaaaaag | acaacataaa | gagtatcctt | tgcaaaaaaa | atgtctaaag | ttcataaaat | 780 |
| acaagcaaaa | acgcaatcac | acacagtgga | cccaaaagcc | atgcacaaca | acacgtactc | 840 |
| accaaggtgc | aatcgtgctg | cccaaaaaca | ttcaccaact | caatccatga | tgagcccaca | 900 |
| catttgttgt | ttgtaaccaa | atctcaaacg | cggtgttctc | tttggaaagc | aaccatatca | 960 |
| gcatatcaca | ctatctagtc | tcttggatca | tgcatgcgca | accaaaagac | aacacataaa | 1020 |
| gtatcctttc | gaaagcaatg | tccaagtcca | tcaaataaaa | ttgagacaaa | atgcaacctc | 1080 |
| accccacttc | actatccatg | gctgatcaag | atcgccgcgt | ccatgtaggt | ctaaatgcca | 1140 |
| tgcacatcaa | cacgtactca | acatgcagcc | caaattgctc | accatcgctc | aacacatttc | 1200 |
| ttgttaattt | ctaagtacac | tgcctatgcg | actctaactc | gatcacaacc | atcttccgtc | 1260 |
| acatcaattt | tgttcaattc | aacacccgtc | aacttgcatg | ccaccccatg | catgcaagtt | 1320 |
| aacaagagct | atatctcttc | tatgactata | aatacccgca | atctcggtcc | aggttttcat | 1380 |
| c | | | | | | 1381 |

<210> SEQ ID NO 53
<211> LENGTH: 1650
<212> TYPE: DNA
<213> ORGANISM: Glycine max
<220> FEATURE:
<221> NAME/KEY: promoter
<222> LOCATION: (1)..(1650)
<223> OTHER INFORMATION: G.max soyAP1 promoter

<400> SEQUENCE: 53

| | | | | | |
|---|---|---|---|---|---|
| agtggagtag | caaaggacga | gaggtagggg | tgtagggaaa | ttgccaacag | ggtagttttg | 60 |
| ggagtaagaa | ttttgggagt | gataatagca | accctcaagt | aagtccttta | gcagaccaaa | 120 |
| cactaaaaat | acaaacgaat | aaacatctaa | tgggccttag | actcaggctt | aaattgaaga | 180 |
| accatacatg | tcagtgtcac | cctgcaaaaa | aggtgagaac | tgagaactat | tacaaaattg | 240 |

```
ttatatgact gcatgctgag atttattaaa ttcttaaccg accttaaaac tcttatgtaa    300
atgtgttttt tcagcgtgat ttttttatt ttcaatttat tttaatattc taaaaatcat    360
caagttctat gattactttt ttttaatatc aaatattaaa tttattgatg aaaggaaaat    420
tcaattgaat ccctttaaac atagtttgga atatccttaa aaacatgatt tgtgaagatt    480
ggaagataat ttaacaaaaa gtataaatgt ataataggaa atgaaggtgt aactgtgtaa    540
gtgaagacaa gcataaaaga gaaatgagga gagggaggtg aggtgtcgcg tgctaaggaa    600
gccaagtggt gcagatgctg gcatcgtttt ctagttttaa gggattctgt tgcaaacccc    660
actcgctacg tatctgcatg catgatgcat atgcatatgc atggtctcag ggtaaaccgt    720 tccttttct tcattcatct ttaccaaccc atcctttcat atctacggcc aagatcacgt    780
agaaatggac ggtgatgatt gaagattgc accgccaagt ttatttgttg ttttagggga    840
atttggcctg cgttgcgttc ttattaggcg agaagaaagg aataaagggg aaggaaggtg    900
tgacactact gtcatactgc actgcttaca acttttttct ctttctctca attcaattgc    960
cttctcccct gcgaatctct tctccacgta tcggtaaacc tattcctcta accccccattc   1020 tcattctttc atcgcatttt actttattca tcttaaacag ccctcagtct ctcatctgtt   1080
ttcctaaccg cgtttcattt tttatttatt ttgtttttat gcgcagattg tccctgcaaa   1140
ttgcacttta taatataaat aatcgctttt tattttctgt ttatgtcagg cgaattcaat   1200 ttttttttctt ttgcttccct tgtttcggtg gataacaaaa aaaaaataaa atctattatc   1260
gaggtctctt tttcaaattg cacggatgcg tcgatttttt ttcgataaaa aaaaatccat   1320
atcggtatga tcgaacacat gatatttttt ttcgttcgta taccattcgg tgattttttt   1380
ttataatttt tcacaactca attttcttgt tttgtttgca ttggttttg tggaatagac    1440 tattttttg actgaaatgg tggaatagac tatagagatt agaagaactg acacaagatt   1500
ttgaaatgtc tcgtttttt ttcacgtccc cataataata tatttagcat tttcacttgt   1560
tagttaaagc ccacatcccc taatttagag taattattta tgtgctaaca attgcaatta   1620
aagtttattt atttggatga ataggagaac                                   1650
```

<210> SEQ ID NO 54
<211> LENGTH: 1138
<212> TYPE: DNA
<213> ORGANISM: Gossypium hirsutum
<220> FEATURE:
<221> NAME/KEY: promoter
<222> LOCATION: (1)..(1138)
<223> OTHER INFORMATION: G. hirsutum a-globulin A promoter

<400> SEQUENCE: 54

```
ctattttcat cctatttaga aatccaagtt gacacctaaa atttagttgg actgccatgt     60
aggattatcg ttagagagat aacggagctt aacggtagag tgatcacttt gtaacaaaat    120
aataacaaaa gtgactaaag tgtaacattt caaacataaa tgattaaaat ataacctgag    180
gcaaacaaaa atgactattt ttatagatta ccctaaaatt aaagagtcat ggccctagcc    240
cctcgcctac ttgtttgttt ttaataaact aacatagtat aatatattgt taggattata    300
taaaattatt aataaatagt ataattaatt taaaattat gaaaataaa ttaccatatt    360 tcttaaatac gtggcacctt atgttggatt ggactgtata acttatatac tattatctat    420
attgaatcca aatccttact tttaagcgtt tttagtgaaa catttatttt tccattctta    480
ttatataaat ttatataatg atataatatg taatacttag ataatattat tgaaaagaa    540
```

| | |
|---|---|
| taaaaatacc tcaaactttg aaaggactaa tttgtatgag catcaaacgt acaggatacc | 600 |
| aaaagtatac atatctgaat tgttcatat ctcctgcaac tcatagatca tcaccatgca | 660 |
| catgtgtaca cttgacttgt cctctatcaa ctcaacccct aactcagtga atcgggacat | 720 |
| ctctgtctca ctttaaaacc cttcccagtt tcaacactct ttgaattcaa ctgagttcac | 780 |
| atacaacaca acacagtcca tcatctttct gctgttaaag catcatcatt tcgcccttc | 840 |
| cagttacaga tgcaacatga ccccccctgc aacaaagttt gtccgaacct tgctagtacc | 900 |
| atgtgaaggg atgtggcatc tcgatatcta cccaccacta tacaaaaaaa aaaaaagag | 960 |
| acaatatttc gtcttcttta atttgcacac tcgtcatctt gcatgtcaat gtcttcaaca | 1020 |
| cgttgatgaa gatttgcatg caaaaatatc accttccaca gctccacctt ctataaatac | 1080 |
| attaccactc tttgctatta ccatcacaca gtaacaaaat acagagctta tcgtaatc | 1138 |

<210> SEQ ID NO 55
<211> LENGTH: 1227
<212> TYPE: DNA
<213> ORGANISM: Gossypium hirsutum
<220> FEATURE:
<221> NAME/KEY: promoter
<222> LOCATION: (1)..(1227)
<223> OTHER INFORMATION: G. hirsutum storage protein (Gh- sp) promoter

<400> SEQUENCE: 55

| | |
|---|---|
| caatcaagat tttcagaacc aggtcgatag ttgaattagt tatgttattg gtccgactag | 60 |
| tttgattaaa aattattaaa aattcataaa ataagaatag aaaaatcgct ctaatcaagt | 120 |
| tttttagttc gacaagtacc aattcatgga tcaacctgct taacctcttg ttttggacaa | 180 |
| tacctcaacc gcttcttgat ccaatcggtt cggatcacta aaatacccct agaaggagat | 240 |
| gaggctaagc agagcgaaaa taactttcca cgagacgaga atggaaacta ttgtatttaa | 300 |
| atattttgat tggattcaac aatcaatatt ttgtaaaggt aagtatttcc ataaactatt | 360 |
| taagaataat gattcttcat gtgcagaacg cggcggtact atttttcaaga tacaatacat | 420 |
| tactcgacgg aacaattcgt attgcagtac caattatttt aaactgaatg aaatttagaa | 480 |
| acacacaaga aaaaataat ataattataa aagtatcatt gtcttggaac tcagttctat | 540 |
| attaattctc atttttggtg tttatatata gaatactaag aggtactgct tctttgaaaa | 600 |
| gacacaacat tttccttaga aaaaattatg aatagttata tatatttacg taaagacacc | 660 |
| tctcttttaat tacattttc tttctttcct attatatata ttataaataa tataaaactt | 720 |
| taatactata tattttattt gaattacctt tataatatat aatataaatt atttatatgt | 780 |
| tatatattat atacaacaat tattagtaag ttaagattga atcagaaaaa atattacgag | 840 |
| tcaaatagtt ttttactttg ttttataata aaaagtaat taaataaat ttagccccaa | 900 |
| taaaaaaat taaatctact ctttaggtga aatttttaat taattagtcc ctgaggtaag | 960 |
| ctttcggctg ctaagctatg aaattgtcat tatgtataac ttttatgcaa gtgtccctca | 1020 |
| cctctcggac acctccctcc ttcacaaaac agcgaggtgt acgctcacgt gtcaatgttg | 1080 |
| ggttacgtgt taaggctcca acattccgat ccaccggtca atcccctctg tgtactctgt | 1140 |
| gtacataagc tgtgcccat atacaaacac caacggagct caacaaagta tctgtacggt | 1200 |
| accgcattat attttttattg acccaag | 1227 |